(12) United States Patent
Pozuelo Rubio et al.

(10) Patent No.: US 12,419,967 B2
(45) Date of Patent: *Sep. 23, 2025

(54) POLYINOSINIC—POLYCYTIDYLIC ACID COMPOSITIONS AND METHODS OF MAKING SAME

(71) Applicant: HIGHLIGHT THERAPEUTICS, S.L., Valencia (ES)

(72) Inventors: Mercedes Pozuelo Rubio, Valencia (ES); Marisol Quintero Ortiz, Valencia (ES); Ana Villanueva Garcia, Valencia (ES)

(73) Assignee: HIGHLIGHT THERAPEUTICS, S.L., Valencia (ES)

( * ) Notice: Subject to any disclaimer, the term of this patent is extended or adjusted under 35 U.S.C. 154(b) by 229 days.

This patent is subject to a terminal disclaimer.

(21) Appl. No.: 17/989,526

(22) Filed: Nov. 17, 2022

(65) Prior Publication Data

US 2023/0116048 A1    Apr. 13, 2023

Related U.S. Application Data

(60) Continuation of application No. 17/095,059, filed on Nov. 11, 2020, now Pat. No. 11,896,606, which is a continuation of application No. 16/724,519, filed on Dec. 23, 2019, now Pat. No. 10,869,881, which is a division of application No. 15/753,328, filed as application No. PCT/EP2016/078078 on Nov. 17, 2016, now Pat. No. 10,568,971.

(30) Foreign Application Priority Data

Nov. 17, 2015    (EP) .................................... 15194864

(51) Int. Cl.

| | | |
|---|---|---|
| *A61K 47/69* | (2017.01) | |
| *A61K 9/00* | (2006.01) | |
| *A61K 9/08* | (2006.01) | |
| *A61K 9/19* | (2006.01) | |
| *A61K 31/15* | (2006.01) | |
| *A61K 31/713* | (2006.01) | |
| *A61K 31/74* | (2006.01) | |
| *A61K 47/26* | (2006.01) | |
| *A61K 47/50* | (2017.01) | |
| *C07K 16/28* | (2006.01) | |

(52) U.S. Cl.
CPC ........ *A61K 47/6935* (2017.08); *A61K 9/0019* (2013.01); *A61K 9/08* (2013.01); *A61K 9/19* (2013.01); *A61K 31/15* (2013.01); *A61K 31/713* (2013.01); *A61K 31/74* (2013.01); *A61K 47/26* (2013.01); *A61K 47/50* (2017.08); *C07K 16/2818* (2013.01); *C07K 16/2827* (2013.01)

(58) Field of Classification Search
CPC .. A61K 31/713; A61K 31/74; A61K 31/7115; A61K 47/69
USPC ..................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 10,653,768 B2 | 5/2020 | Mutzke et al. | |
| 10,849,921 B2 * | 12/2020 | Quintero Ortiz | ...... A61K 31/74 |
| 10,869,881 B2 * | 12/2020 | Pozuelo Rubio | ....... A61P 35/00 |
| 11,883,424 B2 * | 1/2024 | Quintero Ortiz | ...... A61K 45/06 |
| 11,896,606 B2 * | 2/2024 | Pozuelo Rubio | .. A61K 39/3955 |
| 2009/0117306 A1 | 5/2009 | Miyata et al. | |
| 2011/0003883 A1 | 1/2011 | Lee et al. | |
| 2019/0185859 A1 | 6/2019 | Fotin-Mleczek et al. | |
| 2020/0246451 A1 | 8/2020 | Mutzke et al. | |

FOREIGN PATENT DOCUMENTS

| | | |
|---|---|---|
| CN | 102988303 | 3/2013 |
| CN | 103599071 | 2/2014 |
| WO | WO 2004/045491 | 6/2004 |
| WO | WO 2005/102278 | 11/2005 |
| WO | WO 2008/057696 | 5/2008 |
| WO | WO 2011/003883 A1 | 1/2011 |
| WO | WO 2011/003883 | 11/2011 |
| WO | WO 2013/040552 | 3/2013 |
| WO | WO 2013/063019 | 5/2013 |
| WO | WO 2013/087083 | 6/2013 |
| WO | WO 2013/087083 A1 | 6/2013 |
| WO | WO 2013/164380 | 11/2013 |
| WO | WO 2014/057432 | 4/2014 |
| WO | WO 2014/165296 | 10/2014 |
| WO | WO 2015/067632 | 5/2015 |

(Continued)

OTHER PUBLICATIONS

U.S. Appl. No. 17/988,625 (Year: 2022).*

(Continued)

*Primary Examiner* — Jane J Zara
(74) *Attorney, Agent, or Firm* — Stacey J. Farmer; Grund IP Group

(57) ABSTRACT

The present invention relates to compositions comprising polyinosinic (poly(I)) and polycytidylic acid poly(C) molecules, or a salt and/or solvate thereof, comprising double-stranded polyribonucleotides formed by the respective single-stranded poly(I) and poly(C) molecules and methods of making same. The present invention further relates to compositions wherein the disclosed respective poly(I) and poly(C) single-stranded molecules are annealed to thereby form double-stranded poly(I:C) molecules.

16 Claims, 10 Drawing Sheets

(56) References Cited

FOREIGN PATENT DOCUMENTS

| WO | WO 2015/173824 | 11/2015 |
|---|---|---|
| WO | WO 2015/173824 A1 | 11/2015 |

OTHER PUBLICATIONS

U.S. Appl. No. 18/349,989 (Year: 2023).*

Hafner A et al., "Particulate formulations for the delivery of poly (I: C) as vaccine adjuvant". Advanced Drug Delivery Rev. 2013; 65 (10): 1386-1399.

Schaffert D et al., "Poly (I: C)-mediated tumor growth suppression in EGF-receptor overexpressing tumors using EGF-polyethylene glycol-linear polyethylenimine as carrier". Pharm. Res. 2011; 28 (4): 731-741.

Kabilova T et al., "Immunotherapy of hepatocellular carcinoma with small double-stranded RNA". BMC Cancer. 2014; 14: 338.

Kübler K et al ., "Immunogenic cell death of human ovarian cancer cells induced by cytosolic poly(I:C) leads to myeloid cell maturation and activates NK cells". Eur. J. Immunol. 2011; 41 (10): 3028-39.

Palchetti S et al., "Structural characterization of cationic liposome/ poly(I:C) complexes showing high ability in eliminating prostate cancer cells". RSC Adv. 2013; 3 (46): 24597-24604.

Saheki A et al., "Influence of preparation method on polynucleotide conformation and pharmacological activity of lipoplex". Int. J. Pharm. 2011; 406 (1-2): 117-21.

Chen L et al., "Codelivery of zoledronic acid and doublestranded RNA from core-shell nanoparticles". INt. J. Nanomed. 2013; 8: 137-145.

McBain S et al., "Polyethyleneimine functionalized iron oxide nanoparticles as agents for DNA delivery and transfection". J. Mater. Chem. 2007; 17 (24): 2561-2565.

Cobaleda-Siles M et al., "An Iron Oxide Nanocarrier for dsRNA to Target Lymph Nodes and Strongly Activate Cells of the Immune System". Small. 2014; 10 (24): 5054-67.

Kurosaki T et al., "Ternary complexes of pDNA, polyethylenimine, and γ-polyglutamic acid for gene delivery systems". Biomaterials. 2009; 30 (14): 2846-2853.

Turin-Moleavin I et al., "Dynamic constitutional frameworks (DCFs) as nanovectors for cellular delivery of DNA.". Org. & Biomol. Chem. 2015; 13: 9005-9011.

Bilensoy E, "Cationic nanoparticles for cancer therapy". Expert Opin. Drug Deliv. 2010; 7 (7): 795-809.

Germershaus O and Nultsch K, "Localized, non-viral delivery of nucleic acids: Opportunities, challenges and current strategies". Asi. J. Pharm. Sci. 2015; 10 (3): 159-175.

Islam M et al., "Major degradable polycations as carriers for DNA and siRNA". Journal of Controlled Release 2014; 193: 75-89.

Shabani M et al., "Optimization of Gene Transfection in Murine Myeloma Cell Lines using Different Transfection Reagents". Avicenna J. Med. Biotech. 2010; 2 (3): 123-130.

Pozuelo-Rubio M et al., "BO-110, a dsRNA-Based Anticancer Agent". Nano-Oncologicals in Adv. De. Sci. Tech. 2014, Springer, pp. 453-470.

Tormo D et al., "Targeted Activation of Innate Immunity for Therapeutic Induction of Autophagy and Apoptosis in Melanoma Cells". Cancer Cell. 2009; 16 (2): 103-114.

Bhoopathi P et al., "Pancreatic Cancer-Specific Cell Death Induced In Vivo by Cytoplasmic-Delivered Polyinosine-Polycytidylic Acid". Cancer Res. 2014; 74 (21): 6224-35.

Garcia-Pascual C and Gomez R., "Administration of compound BO-110 reduces neoangiogenesis and cellular proliferation and increases apoptosis in a heterologous mice model of enfometriosis". J. Endometr. 2013; 5 (suppl. 1): S13 (SP-04).

Le U et al., "Tumor chemo-immunotherapy using gemcitabine and a synthetic dsRNA". Canc. Biol. Ther. 2008; 7 (3): 440-447.

Le U et al., "Localized irradiation of tumors prior to synthetic dsRNA therapy enhanced the resultant anti-tumor activity". Radiother. Oncol. 2009; 90 (2): 273-279.

Taura M et al., "TLR3 induction by anticancer drugs potentiates poly I:C—induced tumor cell apoptosis". Cancer Sci. 2013; 101 (70: 1610-7.

Matijevic T et al., "Antitumor Activity from the Combined Application of Poly(I:C) and Chemotherapeutics in Human Metastatic Pharyngeal Cell Lines". Chemotherapy 2011; 57: 460-7.

Levitzki A, "Targeting the immune system to fight cancer using chemical receptor homing vectors carrying polyinosine/cytosine (PolyIC)". Front. Oncol. 2012; 2: 4.

Yoshino H and Kashiwakura I, "Beneficial Effects Of Ionizing Radiation To Enhance Anti-Cancer Effects Of RIG-Like Receptor Stimulus". Blood 2013; 122:4721.

Zhou Y et al., "TLR3 activation efficiency by high or low molecular mass poly I:C". Innate Immun. 2013; 19 (2): 184-192.

Ammi R et al., "Poly(I:C) as cancer vaccine adjuvant: Knocking on the door of medical breakthroughs". Pharmacol. Ther. 2015; 146:1 20-31.

Nagato T and Celis E, "A novel combinatorial cancer immunotherapy". Oncoimmunology 2014; 3 (5): e28440.

Zhang Y et al., "Phosphorothioate modification of the TLR9 ligand CpG ODN inhibits poly (I: C)-induced apoptosis of hepatocellular carcinoma by entry blockade". Cancer Lett. 2014; 355: 76-84.

Ohashi T et al., "Dichloroacetate improves immune dysfunction caused by tumor-secreted lactic acid and increases antitumor immunoreactivity". Int. J. Cancer. 2013; 133 (5): 1107-18.

Chiba Y et al., "IL-27 Enhances the Expression of TRAIL and TLR3 in Human Melanomas and Inhibits Their Tumor Growth in Cooperation with a TLR3 Agonist Poly(I:C) Partly in a TRAIL-Dependent Manner". PLoSOne 2013; 8: e76159.

Ho V et al., "TLR3 agonist and Sorafenib combinatorial therapy promotes immune activation and controls hepatocellular carcinoma progression". Oncotarget 2015; 6 (29): 27252-27266.

Gupta S et al., "Poly (I:C) enhances the anti-tumor activity of canine parvovirus NS1 protein by inducing a potent anti-tumor immune response". Tumor Biol. 2016; 37 (9): 12089-12102.

Szabo A et al., "Temporally designed treatment of melanoma cells by ATRA and polyI: C results in enhanced chemokine and IFNβ secretion controlled differently by TLR3 and MDA5". Melanoma Res. 2012; 22 (5): 351-361.

Yu L et al., "Polyinosinic—polycytidylic acid inhibits the differentiation of mouse preadipocytes through pattern recognition receptor— mediated secretion of tumor necrosis factor—α ". Immunol. Cell Biol. 2016; 94 (9): 875-885.

Cho K et al., "Poly I:C primes the suppressive function of human palatine tonsil-derived MSCs against Th17 differentiation by increasing PD-L1 expression". Immunobiology 2016; 222 (2): 394-398.

Vega-Letter A et al., "Differential TLR activation of murine mesenchymal stem cells generates distinct immunomodulatory effects in EAE". Stem Cell Res. & Ther. 2016; 7: 150.

Perrot I et al., "TLR3 and Rig-Like Receptor on Myeloid Dendritic Cells and Rig-Like Receptor on Human NK Cells Are Both Mandatory for Production of IFN-γ in Response to Double-Stranded RNA". J. Immunol. 2010; 185 (4): 2080-2088.

Bald T et al., "Immune Cell-Poor Melanomas Benefit from PD-1 Blockade after Targeted Type I IFN Activation". Cancer Discov. 2014; 4: 674-87.

Amos SM et al., "Adoptive immunotherapy combined with intratumoral TLR agonist delivery eradicates established melanoma in mice". Cancer Immunol. Immunother. 2011; 60 (5): 671-83.

Sajadian A et al., "Comparing the effect of Toll-like receptor agonist adjuvants on the efficiency of a DNA vaccine". Arch. Virol. 2014; 159 (8): 1951-1960.

Fujimura T et al., "Inhibitory effect of the polyinosinic—polycytidylic acid/cationic liposome on the progression of murine B16F10 melanoma". Eur. J. Immunol. 2006; 36 (12): 3371-80.

Storz U, "Intellectual property protection". MAbs. 2011; 3 (3): 310-7.

Keir M et al., "PD-1 and Its Ligands in Tolerance and Immunity". Annu. rev. Immunol. 2008; 26: 677-704.

Galluzzi L et al., "Classification of current anticancer immunotherapies". Oncotarget 2014; 5 (24): 12472-508.

Vacchelli E et al., "Trial Watch Toll-like receptor agonists for cancer therapy". Oncoimmunology 2013; 2 (8): e25396, e23510, e25595.

(56) References Cited

OTHER PUBLICATIONS

Van Der Jeught K et al., "Targeting the tumor microenvironment to enhance antitumor immune responses". Oncotarget 2015; 6 (3): 1359-81.
Ewel C et al., "Polyinosinic-Polycytidylic Acid Complexed with Poly-l-lysine and Carboxymethylcellulose in Combination with Interleukin 2 in Patients with Cancer: Clinical and Immunological Effects". Cancer Res. 1992; 52 (11): 3005-10.
Sanchez-Paulete AR et al., "Cancer Immunotherapy with Immunomodulatory Anti-CD137 and Anti-PD-1 Monoclonal Antibodies Requires BATF3-Dependent Dendritic Cells". Cancer Discov. 2015; pii: CD-15-0510.
Duewell P et al., "Targeted activation of melanoma differentiation-associated protein 5 (MDA5) for immunotherapy of pancreatic carcinoma". OncoImmunol. 2015; 4 (10): e1029698.
David Schaffert et al: "Poly(I:C)-Mediated Tumor Growth Suppression in EGF-Receptor Overexpressing Tumors Using EGF-Polyethylene Glycol-Linear Polyethylenimine as Carrier", Pharmaceutical Research, vol. 28, No. 4, Apr. 1, 2011 (Apr. 1, 2011).
Kurosaki T et al: "Ternary complexes of 1-25 pDNA, polyethylenimine, and gamma-polyglutamic acid for gene delivery systems", Biomaterials, Elsevier Science Publishers BV., Barking, GB, vol. 30, No. 14, May 1, 2009 (May 1, 2009).

\* cited by examiner

FIG. 3A
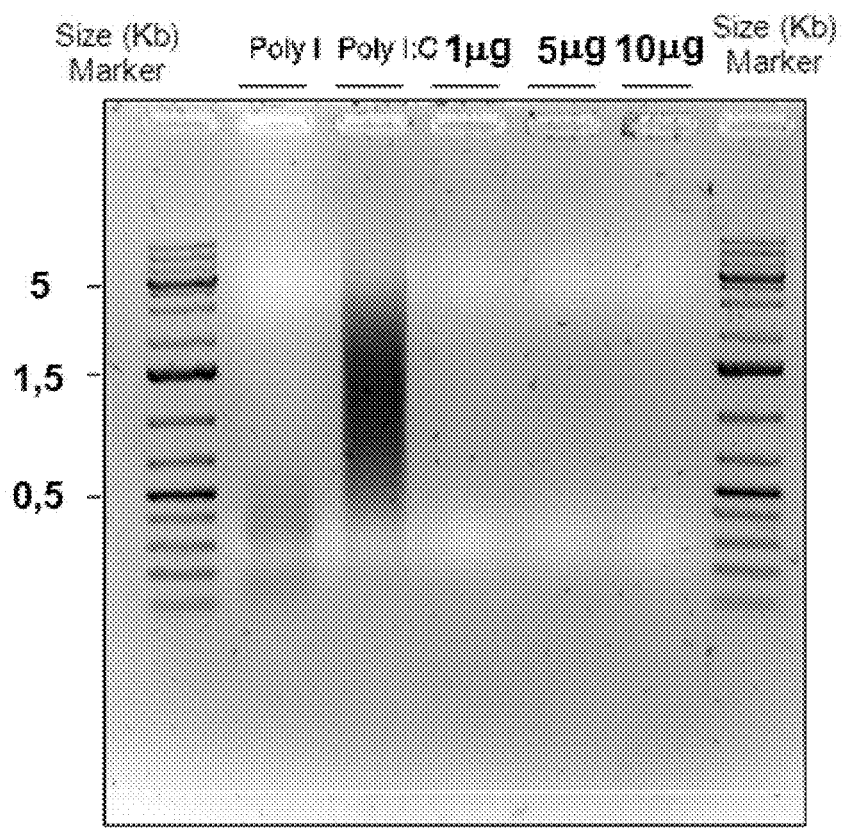
FIG. 3B
FIG. 3C
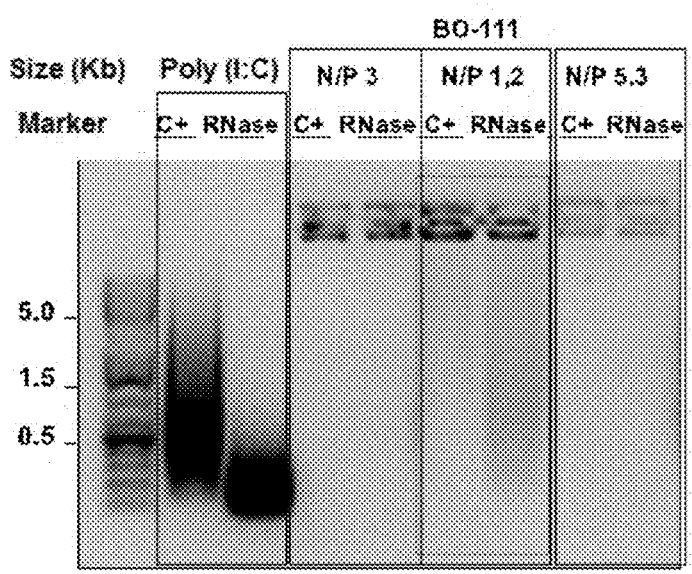

POLYINOSINIC—POLYCYTIDYLIC ACID COMPOSITIONS AND METHODS OF MAKING SAME

CROSS-REFERENCE TO RELATED APPLICATIONS

This application is a continuation application from co-pending U.S. application Ser. No. 17/095,059, filed on Nov. 11, 2020, which is a continuation of U.S. application Ser. No. 16/724,519, filed on Dec. 23, 2019 now U.S. Pat. No. 10,869,881 issued on Dec. 22, 2020, which is a divisional application from U.S. application Ser. No. 15/753,328, filed on Feb. 18, 2018 now U.S. Pat. No. 10,568,971 issued on Feb. 25, 2020, which claims the benefit of International Patent Application PCT/EP2016/078078, filed Nov. 17, 2016, published as International Patent Publication WO 2017/085228 on May 26, 2017, which claims the benefit of European Patent Application EP 15194864.3, filed on Nov. 17, 2015, the contents of each are hereby incorporated by reference.

FIELD OF THE INVENTION

The present invention relates to the field of polyinosinic (poly(I))-polycytidylic acid poly(C) compositions.

BACKGROUND OF THE INVENTION

The use of synthetic analogs of double-stranded RNA (dsRNA) that mimic viral dsRNA has been explored in recent years for specifically activating the immune system against tumors with the scope of inhibiting cancer cell growth and inducing cancer cell apoptosis. In particular, double-stranded polyinosinic-polycytidylic acid (named as poly(I:C) or pIC) has been characterized as a type of dsRNA with various effects of therapeutic interest against various cancers (such as melanoma, hepatoma, colon, gastric, and oral carcinoma, cervical cancer, breast cancer, ovarian cancer, urinary tract tumors, lung and prostate cancer) and their metastasis, in manners that may be dependent or independent from immune system activation, natural killer- and/or dendritic cell-mediated activities, and/or changes of tumor gene expression and microenvironment (Hafner A et al., 2013).

Unfortunately, these initial preclinical evidences are poorly or not confirmed in clinical studies with naked poly(I:C) molecules that revealed its low stability, poor homogeneity, unpredictable pharmacokinetics, and limited antitumoral effects due to a variety of mechanisms, such as poor cellular uptake or degradation by cytosolic RNases (Hafner A et al., 2013). Indeed, in order to achieve an effective therapeutic or prophylactic effect, poly(I:C) molecules may need to be re-dissolved immediately prior or shortly before use, may be available in formulations at low concentrations, and/or are frequently administered (e.g. every 2 hours).

During the last few years, there has been significant progress in formulating poly(I:C) molecules with immunomodulatory and/or therapeutic properties. Various methods of preparing and formulating poly(I:C) molecules as powder and/or integrated within polymer-based microparticles with or without targeting moieties and additional chemical linkers have been disclosed (CN103599071; CN102988303; WO2004045491; WO2008057696; WO2013164380; WO2015067632, WO2014057432; WO2014165296; Schaffert D et al., 2011; WO2015173824, Kabilova T et al., 2014; Kübler K et al., 2011; Palchetti S et al., 2013; Saheki A et al., 2011). Poly(I:C) molecules have been formulated with carrier polymers and in formats compatible for nasal administration (WO2013164380), stabilized with polylysine and carboxymethylcellulose (WO2005102278), encapsulated within cationic lipid-coated calcium phosphate nanoparticles, liposomes, or other vesicular structures (Chen L et al., 2013; US2009117306; US2011003883, or together with single stranded RNA and with cationic peptides like protamine (WO2013087083). Alternatively, poly(I:C) molecules have also been immobilized on solid particles and carriers such as iron oxide nanoparticles, with or without agents that would help targeting poly(I:C) molecules to specific cells or tissues (McBain S et al., 2007; Cobaleda-Siles M et al., 2014).

Some publications further disclose various ternary or quaternary complexes in the sub-micrometer range that are formed by polymers, poly(I:C) and/or double stranded DNA, with or without other components and gene-specific (Kurosaki T et al., 2009.; WO2013040552; WO2013063019; Tutin-Moeavin I et al., 2015). However, these approaches have the objective of providing agents that essentially administer DNA to the cells, while maintaining their viability, and not the selective killing of cancer cells.

The pitfalls that are limiting the clinical development of poly(I:C) molecules as a drug and its compliancy with regulatory requirements could be overcome by producing structurally complex anticancer complexes comprising poly (I:C) molecules together with drug delivery systems for cancer therapy that are often based on cationic polymers such as chitosan, polyethyleneimine (PEI), poly-L-lysine, polymethacrylates, imidazole- or cyclodextrin-containing polymers, poly(beta-amino ester) s, and related dendrimers. These polymeric systems (also called as Polyplex) are structurally and functionally distinct from lipid-based systems (also called as Lipoplex) and hybrid systems (also called as Lipopolyplex) that are similarly used for the local or systemic delivering of nucleic acids (Bilensoy E, 2010; Germershaus O and Nultsch K, 2015). Among Polyplex, PEI is a cationic polymer of particular interest that can be modified at the level of linear/branched structure and size, chemical linkage, degradability, and derivatization (Islam M et al., 2014) and that, differently from lipoplex internalization by cells, is internalized both by clathrin-mediated and by caveolae mediated endocytosis (Shabani M et al., 2010).

This therapeutic approach involving the preparation and the administration of poly(I:C) molecules associated to PEI has been exemplified in the literature by the agent called BO-110 (Pozuelo-Rubio M et al., 2014; Tormo D et al., 2009; WO2011003883). This complex, also identified as $[pIC]^{PEI}$, not only engages a dual induction of autophagy and apoptosis in several cancer cell lines of melanoma and of other tumor types (such as gliomas or carcinomas) but also has no or limited effect on the viability of normal cells, such as melanocytes. BO-110 inhibits melanoma growth in animal models for demonstrating antitumoral and antimetastatic activity in vivo, even in severely immunocompromised mice. Moreover, a similar $[pIC]^{PEI}$-based agent stimulates the apoptosis in pancreatic ductal adenocarcinoma cells without affecting normal pancreatic epithelial cells and in vivo administration of $[pIC]^{PEI}$ inhibited tumor growth in tumor animal models (Bhoopathi P et al., 2014). A further effect of BO-110 administration is characterized in a model of endometriosis, wherein such agent reduces angiogenesis and cellular proliferation and increases apoptosis (Garcia-Pascual C and Gomez R, 2013).

Thus, BO-110 and similar [pIC]$^{PEI}$ agents that comprise double-stranded polyribonucleotides represent a novel anticancer strategy with a broad spectrum of action, due to the combined activation of autophagy and apoptosis, autonomously and selectively in tumor cells, while maintaining the viability of normal cells of different lineages. However, BO-110, as for other double-stranded polyribonucleotide-based agents that have demonstrated efficacy in various pre-clinical models when associated with carriers, still needs to be provided in formulations that are stable in different storage conditions, uniformly manufactured and sized.

Indeed, prior art does not provide appropriate teaching for solving issues related to the most effective combination of structural and biophysical criteria that allow the production of poly(I:C)-containing compositions for treatment of cancer. Regulatory agencies also require being strictly compliant to the specifications on reproducibility, storage, and uniformity of the size and concentration of poly(I:C)-containing particles that are included within compositions for use in humans. Thus, agents, compositions, and related processes providing double-stranded polyribonucleotide molecules, such as poly(I:C) molecules, at higher, and well-controlled, concentrations are still needed to allow their extensive pre-clinical and clinical development as a drug (in particular against cancer), while improving patient compliance and reducing the frequency of dosing double-stranded polyribonucleotide molecules with well-defined safety margin and therapeutic effects.

SUMMARY OF THE INVENTION

The present invention relates to a composition comprising particles wherein
- (i) each of said particles comprises a complex of at least one double-stranded polyribonucleotide, or a salt or solvate thereof, and at least one polyalkyleneimine, or a salt and/or solvate thereof;
- (ii) at least 95%, or at least 90%, of said particles has a diameter of less than or equal to 600 nm, preferably, less than or equal to 300 nm (for example, between 140 and 250 nm); and
- (iii) said particles have a z-average diameter of less than or equal to 200 nm, preferably less than or equal to 150 nm, in particular, as measured according to ISO 22412.

In a preferred embodiment, the present invention relates to an aqueous composition comprising particles wherein
- (i) each of said particles comprises a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
- (ii) at least 90% of said particles has a mono-modal diameter distribution below 300 nm;
- (iii) said particles have a z-average diameter of less than or equal to 150 nm, as measured according to ISO 22412; and
- (iv) said composition has a zeta potential equal or superior to 30 mV, according to ISO 13099.

The present invention also relates to an aqueous composition comprising particles as disclosed herein wherein:
- (i) each of said particles is formed by making a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
- (ii) at least 90% of said particles has a mono-modal diameter below 300 nm;
- (iii) said particles have a z-average diameter of less than or equal to 150 nm, as measured according to ISO 22412; and
- (iv) said composition has a zeta potential equal or superior to 30 mV, according to ISO 13099;

wherein said particles are formed at the ratio of the number of moles of nitrogen of said polyalkyleneimine to the number of moles of phosphorus of said double-stranded polyribonucleotide in said composition being equal to or greater than 2.5.

The present invention also relates to a composition obtainable by lyophilisation of the aqueous composition as disclosed herein.

In addition, the present invention relates to a composition, as disclosed herein, for use as a medicament.

Moreover, the present invention relates to a composition, as disclosed herein, for use in treatment of a cell growth disorder characterized by abnormal growth of human or animal cells.

Furthermore, the present invention relates to a process to manufacture the composition, as disclosed herein, which comprises:
- (i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
- (ii) independently filtering each solution through a filter having a pore diameter of less than or equal to 500 nm to form sterilized solutions;
- (iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and optionally
- (iv) filtering the resulting aqueous composition through a filter having a pore diameter of less than or equal to 600 nm to form a filtrate, or centrifuging the resulting aqueous composition at greater than or equal to 22480 m/s$^2$ to form a supernatant; and/or
- (v) lyophilising the resulting aqueous composition, filtrate or supernatant.

Preferably, the present invention also relates to a composition comprising particles wherein:
- (i) each of said particles comprises a complex of at least one double-stranded polyribonucleotide, or a salt or solvate thereof, and at least one polyalkyleneimine, or a salt and/or solvate thereof, wherein
  - (a) said double-stranded polyribonucleotide is polyinosinic-polycytidylic acid [poly(I:C)] or polyadenylic-polyuridylic acid [poly(A: U)], wherein at least 60% of said double-stranded polyribonucleotides have at least 850 base pairs, at least 70% of said double-stranded polyribonucleotides have between 400 and 5000 base pairs, and between 20% and 45% of said double-stranded polyribonucleotides have between 400 and 850 base pairs; and
   (b) said polyalkyleneimine comprises at least 95% polyethyleneimines, wherein the weight average molecular weight of said polyalkyleneimine is between 17 and 23 kDa and the polydispersity index is <1.5, and wherein the ratio of the number of moles of nitrogen of said polyalkyleneimine to the number of moles of phosphorus of said double-stranded polyribonucleotide in said composition is between 2.5 and 5.5;
 (ii) at least 99% of said particles has a diameter of less than or equal to 600 nm; and
 (iii) said particles have a z-average diameter of between 30 nm and 150 nm.

More preferably, the present invention also relates to an aqueous composition which comprises particles wherein:
 (i) each of said particles comprises a complex of at least one double-stranded polyribonucleotide, or a salt or solvate thereof, and at least one polyalkyleneimine, or a salt and/or solvate thereof, wherein
   (a) said double-stranded polyribonucleotide is polyinosinic-polycytidylic acid [poly(I:C)], wherein at least 60% of said poly(I:C) has at least 850 base pairs, at least 70% of said poly(I:C) has between 400 and 5000 base pairs, and between 20% and 45% of said poly(I:C) has between 400 and 850 base pairs; and
   (b) said polyalkyleneimine is polyethyleneimine (PEI), wherein the weight average molecular weight of said PEI is between 17.5 and 22.6 kDa and the polydispersity index is <1.5, and wherein the ratio of the number of moles of nitrogen of said polyalkyleneimine to the number of moles of phosphorus of said double-stranded polyribonucleotide in said composition is between 2.5 and 4.5;
 (ii) at least 99% of said particles has a diameter of less than or equal to 500 nm;
 (iii) said particles have a z-average diameter of between 60 nm and 130 nm; and
 (iv) said particles have a median diameter (D50%) of between 75 nm and 150 nm.

Further embodiments related to the preparation of such compositions in form of BO-11X formulations, their features, their analysis and their uses are provided in the Detailed Description and in the Examples below.

BRIEF DESCRIPTION OF THE DRAWINGS

FIG. 1A: Poly(I:C) molecules are associated with PEI to form BO-111 complexes according to the description of the 2-vial manufacturing processing in Example 1, and the resulting solution is either filtered using membrane with different pore sizes (and then using the flow-through solution for cell-based assays) or centrifuged at different speeds (and then using the supernatant for cell-based assays), generating distinct BO-111 preparations, each of them containing poly(I: C)-based complexes with a more homogeneous, lower size that is determined as Z-average (hydrodynamic diameter, expressed as d.nm). Qualitatively similar data were generated by testing cell death at 24 hours. Data on cell death are compared with sample not treated with BO-111. FIG. 1B: Dose-response activity of a BO-111 preparation that is obtained by filtering through 0.8 µm filter (hatched bars) when compared to the corresponding unfiltered BO-111 preparation (white bars). Since centrifugation or filtration causes some loss of poly(I:C) due to the sedimentation or retention of bigger complexes (respectively), the amount of poly(I:C) in each distinct BO-111 preparation was quantified by spectrophotometric analysis at wavelength of 260 nm, in order to compare correctly the effects of such preparation on cells by diluting accordingly the initial preparation at the appropriate concentration. Qualitatively similar data were generated by testing cell death at 12, 24, and 36 hours. Cell death is determined by Trypan Blue assay as described in the literature. Standard deviation is calculated using triplicate data for each condition of the same experiment.

FIG. 2A: Distinct BO-111 preparations were obtained by using commercial JetPEI preparations containing linear polymers having different molecular weight (expressed in kiloDalton; NT: control, not treated cells; such JetPEI preparations present a mono-modal distribution with polydispersity index that is inferior to 1.5, in particular comprised between 1.1 and 1.4). FIG. 2B: Distinct BO-111 preparations were obtained by modifying the ratio N/P (from 1.2 to 5.3) that is calculated as: µL PEI x 150 nM/µg poly(I:C)x3 nmol, wherein 150 nM refers to the concentration of nitrogen residues in PEI and 3 nmol refers to the number of nanomoles of anionic phosphate per 1 µg poly (I:C). The pharmacological effect of each combination is determined by comparing cell death percentages in both melanoma cells and melanocytes (control cells; NT: control, not treated cells). The same poly(I:C) preparation as described in FIG. 1A and FIG. 1B was used for all BO-111 preparations that are described in FIG. 2A and FIG. 2B but, instead of applying the "fast pipetting" method, poly(I:C) solution was quickly injected in the vial containing the PEI solution using a syringe, increasing the mixing speed (at least as it can be visually determined). Standard deviation is calculated using triplicate data from each condition of the same experiment.

FIG. 3A to FIG. 3C show an analysis of poly(I:C) molecules within BO-111 preparations by electrophoresis. FIG. 3A: Unlabelled preparations of initial poly(I) or poly (I:C) molecules are compared to increasing amounts of BO-111 preparations in agarose gel 0.8% (1 hour electrophoresis). The molecular size of poly(I:C) molecules is determined in comparison with size markers. FIG. 3B: Radiolabeled poly(I:C) molecules are compared to unlabeled poly(I:C) and to a BO-111 preparation including the same radiolabeled poly(I:C), using an agarose gel 1% (1-hour electrophoresis) that is exposed to a photographic film. The poly(I:C) molecules within the different BO-111 preparations that are not visible in panel (A) appear in panel (B) as being blocked within the well of agarose gel since they are associated to JetPEI forming particles that (due to their size and/or charge distribution) the electric field cannot displace across the agarose gel. FIG. 3C: Unlabelled poly (I:C) molecules are compared with distinct BO-111 preparations obtained by modifying the ratio N/P (1.2, 3 and 5.3; this value is calculated as in FIG. 2A and FIG. 2B) in agarose gel 0.8% (1-hour electrophoresis). Each sample is either untreated (C+) or treated with a specifically degrading enzyme (RNAse; Rnase A: 5 µg/mL over 30 minutes) prior to be loaded on the agarose gel, in order to evaluate the stability of poly(I:C) molecules in different BO-111 preparations. The poly(I:C) molecules appear insensitive to such enzyme when complexed with JetPEI at higher N/P ratios (greater than or equal to 3), and a smear of poly(I:C) molecules appears released when the N/P ratio is below 3. In panels (A) and (C), the molecular size of poly(I:C) molecules is determined in comparison with size marker.

FIG. 4A: Comparison of particle diameter distribution was performed using three different BO-111 batches obtained by using the same production process. FIG. 4B: Comparison of distinct BO-111 preparations when exposing (or not, sample indicated as CONTROL) to an incubation at room temperature in agitation for 30 minutes. FIG. 4C: Comparison of distinct BO-111 preparations when exposing (or not, sample indicated as CONTROL) to an incubation at 50° C. for a period of 30 minutes. FIG. 4D: Comparison of distinct BO-111 preparations, control manufacture as suggested in Example 1 and "Slow Mixing" sample, evaluated by triplicate profiles, that was obtained by the drop-by-drop approach using a reduced mixing speed. Particle size is evaluated considering particle diameter in nanometers (d.nm).

FIG. 5A: Flowchart summarizing main steps for manufacturing BO-112 compounds as a GMP-compliant, pharmaceutical preparation comprising poly(I:C) molecules, commercial JetPEI preparations, and glucose. FIG. 5B: Permeation Chromatograms for BO-112, JetPEI, and glucose samples that are analyzed using refractive index detection (RI). The BO-112 signal overlaps with the glucose signal, while the characteristic peak of free JetPEI at the Retention Volume of 13.75 mL disappeared, suggesting that all initial JetPEI was incorporated into BO-112.

FIG. 6A: The molecular size of different poly(I: C) preparations is determined in agarose gel using size markers. FIG. 6B: Size distribution of BO-112 complexes is compared to three poly(I:C)-containing commercial products (Poly-ICLC, LyoVec-HMW, and LyoVec-LMW; particle size is defined as in previous figures in nm).

FIG. 8C: Effect of different poly(I:C) formulations on signaling molecules of therapeutic interest. Interferon-beta (IFN-beta) expression was evaluated by RT-qPCR method in SK-MEL-103 cells that were exposed to BO-112, Poly-ICLC (or untreated, NT) for 8, 16 and 24 hours. BO-112 and Poly-ICLC formulations were used at a concentration providing a similar content of poly(I:C) molecules.

FIG. 10A: Timeline showing the schedule of treatment. All mice were injected sub-cutaneously with B16-F10 murine melanoma cells at day 0. After randomizing mice into five groups presenting tumors of similar average size (80-100 mm3) on day 7, animals were treated with BO-112 formulation (double circles) by injection straight into the tumor tissue (i.t. treatment) at 3 different concentrations in groups 2, 3, and 4 (G2, G3, G4) or, in the two remaining groups (G1 and G5), with vehicle only. On the following treatment days (10, 14, 17, 21 and 24) all groups but G1, received intraperitoneal (i.p.) administration of an anti-PD-L1 murine antibody (150 µg/dose) in addition to the intratumoral administration of BO-112 formulation at the same concentration of day 7. Survival was monitored daily, and mice were scored as dead upon finding them deceased, or when the tumor volume reached the maximum allowed size. Monitoring continued after last treatment until day 45, when the last mouse died and the experiment was terminated. FIG. 10B: Survival curve comparing the control groups G1 and G5 with the three groups in which BO-112 formulation was administered at the indicated three concentrations. When comparing the groups, there was a statistical difference (p<0.0001, Log-rank Mantel-Cox test) between the control groups and the test groups, with G4 showing the strongest increase of survival relative to vehicle or anti-PD-L1 alone.

DETAILED DESCRIPTION OF THE INVENTION

Figure 1A:
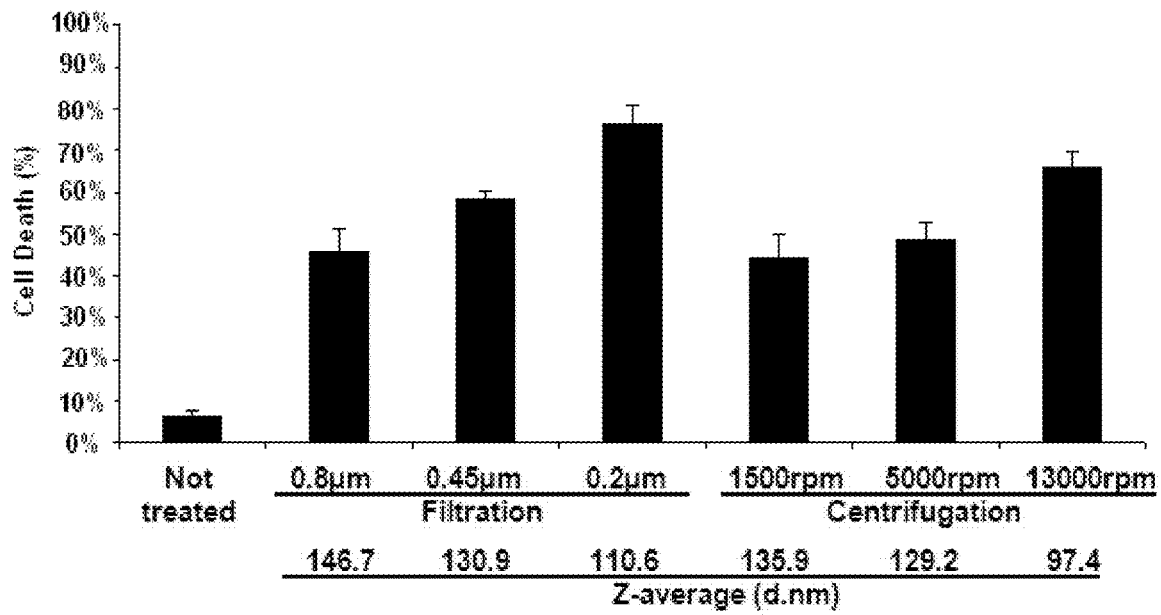
FIG. 1A and FIG. 1B show the functional activity of distinct BO-111 preparations following filtration or centrifugation by analyzing cell death in melanoma cells SK-Mel-103 after a 48-hour exposure.

The present invention relates to a composition comprising particles wherein:
(i) each of said particles comprises a complex of at least one double-stranded polyribonucleotide, or a salt or solvate thereof, and at least one polyalkyleneimine, or a salt and/or solvate thereof;
(ii) at least 95% of said particles has a diameter of less than or equal to 600 nm, preferably, less than or equal to 300 nm; and
(iii) said particles have a z-average diameter of less than or equal to 200 nm, preferably less than or equal to 150 nm, in particular, as measured according to ISO 22412.

In a preferred embodiment, the present invention relates to an aqueous composition comprising particles wherein
(i) each of said particles comprises a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
(ii) at least 90% of said particles has a mono-modal diameter distribution below 300 nm;
(iii) said particles have a z-average diameter of less than or equal to 150 nm, as measured according to ISO 22412; and
(iv) said composition has a zeta potential equal or superior to 30 mV, according to ISO 13099

The present invention also relates to an aqueous composition comprising particles as disclosed herein wherein:
(i) each of said particles is formed by making a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
(ii) at least 90% of said particles has a mono-modal diameter distribution below 300 nm;
(iii) said particles have a z-average diameter of less than or equal to 150 nm, as measured according to ISO 22412; and
(iv) said composition has a zeta potential equal or superior to 30 mV, according to ISO 13099;
wherein said particles are formed at the ratio of the number of moles of nitrogen of said polyalkyleneimine to the number of moles of phosphorus of said double-stranded polyribonucleotide in said composition being equal to or greater than 2.5.

The particles that are made of and formed by said complexes may present additional features, as per the disclosure below, such that in further embodiments said particles may comprise further components such as excipients like mannitol or glucose, or the absence of further elements, such as cancer-targeting functionality or other moieties and linkers. Additional features can be defined in further preferred embodiments when the particles are provided and analysed within the compositions [i.e. within the liquid (aqueous) or lyophilised formulations], such as when defined as having a mono-modal size distribution within specific ranges, for example, between 30 nm and 150 nm, or when the composition is characterised by the absence of single-stranded polyribonucleotide molecules (as established by a low or absent hyperchromic effect). Other features as defined in accordance to internationally established standards that are required for regulatory approval and/or Good Manufacturing Processes are disclosed in the following.

In a preferred embodiment of the composition of the present invention, at least 40% of the double-stranded polyribonucleotides comprised in said composition have at least 850 base pairs, and at least 50% of the double-stranded polyribonucleotides comprised in said particles have between 400 and 5000 base pairs. Moreover, the double-stranded polyribonucleotides that are comprised in the complexes may present specific ranges of lengths that are defined by their processes of preparation and/or according to the desired use. For example, at least 40%, 50%, 60%, or any other higher percentage of the double-stranded polyribonucleotides comprised in said particles may have at least 850 base pairs, and at least 50%, 60%, 70% or any other higher percentage of the double-stranded polyribonucleotides comprised in said particles may have between 400 and 5000 base pairs. Additional ranges that may define double-stranded polyribonucleotides that are comprised in said particles are:
(i) between 5% and 60% (and preferably between 10% and 30%) of double-stranded polyribonucleotides having less than 400 base pairs;
(ii) between 20% and 45% (or between 15% and 30%, but preferably between 20% and 30%) of double-stranded polyribonucleotides having between 400 and 850 base pairs;
(iii) between 20% and 70% (and preferably between 50% and 60%) of double-stranded polyribonucleotides having between 850 and 5000 base pairs; and/or
(iv) between 0% and 10% (and preferably 1% or less) of double-stranded polyribonucleotides having more than 5000 base pairs.

Thus, in more preferred embodiment of the composition of the present invention, at least 50% of the double-stranded polyribonucleotides comprised in said composition have at least 850 base pairs, and at least 60% of the double-stranded polyribonucleotides comprised in said composition have between 400 and 5000 base pairs. Yet more preferably, at least 60% of the double-stranded polyribonucleotides comprised in said composition have at least 850 base pairs, at least 70% of said double-stranded polyribonucleotides comprised in said composition have between 400 and 5000 base pairs, and between 20% and 45% of said double-stranded polyribonucleotides have between 400 and 850 base pairs. Even more preferably, at least 60% of the double-stranded polyribonucleotides comprised in said composition have at least 850 base pairs, at least 70% of said double-stranded polyribonucleotides comprised in said composition have between 400 and 5000 base pairs, between 20% and 30% of said double-stranded polyribonucleotides have between 400 and 850 base pairs, and between 10% and 30% of said double-stranded polyribonucleotides have less than 400 base pairs.

In one embodiment of the present invention, the double-stranded polyribonucleotide is preferably polyinosinic-polycytidylic acid [poly(I:C)] molecules or polyadenylic-polyuridylic acid [poly(A: U)] molecules. More preferably, the double-stranded polyribonucleotide is polyinosinic-polycytidylic acid [poly(I:C)] molecules. Said double-stranded polyribonucleotide molecules comprise strands of, for example, poly(I) and poly(A) that pair with poly(C) and poly(U), respectively, thus forming double-stranded polyribonucleotides, wherein each strand may comprise up to 5% of ribonucleotides different from the majority of ribonucleotides in said strand and/or comprise up to 5% mismatched base pairs, more preferably up to 1% of ribonucleotides different from the majority of ribonucleotides in said strand, and/or comprise up to 1% mismatched base pairs. Depending on the selected polyribonucleotide and/or the process for generating said complexes, a fraction of the polyribonucleotides comprised in the complex may also comprise single-stranded (i.e. non-paired) polyribonucleotides.

In a preferred embodiment, the content of free, single-stranded polyribonucleotide within these particles and the compositions is evaluated on the basis of the hyperchromicity (or hyperchromic effect). This effect is due to the increase of optical density (absorbance) of double stranded polynucleotides when this duplex structure is denatured. The UV (ultraviolet) absorption of polynucleotides is increased when the two single strands are being separated, either by heat or by addition of denaturant or by increasing the pH level. Hyperchromicity can therefore be used to check the structures of poly(I:C) or poly(A: U) molecules within the particles as temperature (or another condition) changes, thereby respectively determining the separation between poly(I) strands and poly(C) strands in poly(I:C) molecules or the separation between poly(A) strands and poly(U) strands in poly(A: U) molecules. Preferably, such content of single-stranded poly(I) molecules and poly(C) molecules or single-stranded poly(A) molecules and poly(U) molecules in the particles is as low as possible, as determined by measuring absorbance of light in the 260 nm wavelength region using standard equipment and protocols. For instance, this effect can be measured using a spectrophotometer and according to European Pharmacopoeia (2.2.25; Absorption spectrophotometry, ultraviolet and visible). In particular, the compositions disclosed herein exhibit less than a 20% increase in absorption at 260 nm between 20° C. and 80° C., preferably less than a 10%, more preferably less than a 5%, even more preferably, a less than 1% increase in absorption at 260 nm between 20° C. and 80° C. Alternatively, the compositions disclosed herein show a less than 0.2 increase in the transmittance between room temperature and 40° C., 50° C., 60° C., 70° C., 80° C. and 90° C. This value can be measured as the absorbance at 260 nm (A) or the transmittance (1/A) at room temperature and then calculating the difference with the respective value of absorbance or transmittance at the aforementioned higher temperatures.

In a preferred embodiment of the composition of the present invention, the polyalkyleneimine, or a salt and/or solvate thereof, is linear, branched and/or dendritic, more preferably said polyalkyleneimine is a linear polyalkyleneimine. In a more preferred embodiment, said polyalkyleneimineis a homo-polyalkyleneimine or hetero-polyalkyleneimine. The polycationic homo- or hetero-polymer preferably comprises a repeating unit formed by an amine group and at least a two carbon atom spacer, thus comprising homo-polyalkyleneimine or hetero-polyalkyleneimine polymers which are linear or branched and/or dendritic. Examples of polyalkyleneimines are polyethyleneimine, polypropyleneimine, polybutyleneimine and polypentyleneimine, mixed polymers of any of these homopolymers, or any commercially available or otherwise disclosed derivatives. This polyalkyleneimine polymer is preferably water-soluble. In a particularly preferred embodiment of the present invention, said polyalkyleneimine is a water-soluble, linear homo-polyalkyleneimine or hetero-polyalkyleneimine. In an even more preferred embodiment, said polyalkyleneimine comprises in particular a water-soluble linear homo-polyalkyleneimine, more preferably it comprises at least 75% linear polyethyleneimines, yet more preferably 95% linear polyethyleneimines. In a still more preferred embodiment of the composition of the present invention said polyalkyleneimine is polyethyleneimine (also known as PEI). Thus, in an especially preferred embodiment, said polyalkyleneimine is a linear polyethyleneimine.

In another preferred embodiment of the composition of the present invention, the weight average molecular weight of said polyalkyleneimine is between 17 and 23 kDa, still more preferably between 17.5 and 22.6 kDa, and has a molecular weight polydispersity index of <1.5. Said weight average molecular weight and said polydispersity index were determined for the polyalkyleneoxide precursor to said polyalkyleneimine according to ISO 16014:2012, preferably by Gel Permeation Chromatography (GPC) according to ISO 16014-2:2012. The polydispersity index is calculated as $M_w/M_n$ (weight average molecular weight/number average molecular weight) and is inferior to 1.5.

In another preferred embodiment of the composition of the present invention, the ratio of the number of moles of nitrogen of said polyalkyleneimine to the number of moles of phosphorus of said double-stranded polyribonucleotide in said composition is equal to or greater than 2.5, more preferably between 2.5 and 5.5, still more preferably between 2.5 and 4.5, furthermore preferably between 2.5 and 3.5. This ratio is particularly important when forming the particles within the composition and providing compositions having the desired effects and properties.

Thus, as mentioned above, the present invention relates to an aqueous composition comprising particles as disclosed herein wherein:
  (i) each of said particles is formed by making a complex of at least one double-stranded polyribonucleotide, or a salt or solvate thereof, and at least one linear polyalkyleneimine, or a salt and/or solvate thereof, wherein said double-stranded polyribonucleotide is polyinosinic-polycytidylic acid [poly(I:C)] and the average molecular weight of said linear polyalkyleneimine is between 17 and 23 kDa;
  (ii) at least 90% of said particles has a mono-modal diameter distribution below 300 nm;
  (iii) said particles have a z-average diameter of less than or equal to 150 nm, as measured according to ISO 22412; and
  (iv) said composition has a zeta potential equal or superior to 30 mV, according to ISO 13099;
wherein said particles are formed at the ratio of the number of moles of nitrogen of said polyalkyleneimine to the number of moles of phosphorus of said double-stranded polyribonucleotide in said composition being equal to or greater than 2.5, more preferably between 2.5 and 5.5, still more preferably between 2.5 and 4.5, furthermore preferably between 2.5 and 3.5. In a further preferred embodiment, said composition is formed by making a complex from at least 0.5 mg of polyinosinic-polycytidylic acid [poly(I:C)] per mL of the total (i.e. final) volume of said composition, more preferably from at least 2.0 mg of poly(I:C) per mL of the total volume of said composition. Thus, in a particularly preferred embodiment of the invention, the double-stranded polyribonucleotide is polyinosinic-polycytidylic acid [poly(I:C)] or polyadenylic-polyuridylic acid [poly(A: U)], wherein at least 60% of said double-stranded polyribonucleotides have at least 850 base pairs (bp), at least 70% of said double-stranded polyribonucleotides have between 400 and 5000 base pairs, and between 20% and 45% of said double-stranded polyribonucleotides have between 400 and 850 base pairs; and the polyalkyleneimine comprises at least 95% polyethyleneimines, wherein the weight average molecular weight of said polyalkyleneimine is between 17 and 23 kDa and the polydispersity index is <1.5, and wherein the ratio of the number of moles of nitrogen of said polyalkyleneimine to the number of moles of phosphorus of said double-stranded polyribonucleotide used in formation of said composition (i.e. the ratio of the number of moles of nitrogen of said polyalkyleneimine to the number of moles of phosphorus of said double-stranded polyribonucleotide used in formation of said particles) is between 2.5 and 5.5.

In an even more preferable particularly preferred embodiment of the invention, the double-stranded polyribonucleotide is polyinosinic-polycytidylic acid [poly(I:C)], wherein at least 60% of the poly(I:C) molecules have at least 850 base pairs, at least 70% of said poly(I:C) molecules have between 400 and 5000 base pairs, between 20% and 30% of said poly(I:C) molecules have between 400 and 850 base pairs, and between 10% and 30% of said poly(I:C) molecules have less than 400 base pairs; and the polyalkyleneimine is polyethyleneimine, wherein the weight average molecular weight of said polyalkyleneimine is between 17.5 and 22.6 kDa and the polydispersity index is <1.5 (such as between 0.1 and 0.6, as measured within the composition), and wherein the ratio of the number of moles of nitrogen of said polyethyleneimine to the number of moles of phosphorus of said poly(I:C) used in formation of said composition (i.e. the ratio of the number of moles of nitrogen of said polyalkyleneimine to the number of moles of phosphorus of said double-stranded polyribonucleotide used in formation of said particles) is between 2.5 and 4.5.

In the present invention, the z-average diameter and polydispersity index of the diameters of the particles comprised in the composition of the present invention are determined by Dynamic Light Scattering (DLS) techniques, based on the assumption that said particles are isotropic and spherically shaped. In particular, the z-average diameter (zeta-average diameter) refers to the intensity-weighted arithmetic average hydrodynamic diameter of said particles, as determined according to industrial standard ISO 22412:2008. In addition, industrial standard ISO 22412:2008 provides a measure of the particle diameter (size) distribution in the form of a polydispersity index and allows calculation of the percentiles (D values) known as D50% (the maximum particle diameter below which 50% of sample intensity falls, also known as the median diameter), D90% (the maximum particle diameter below which 90% of sample intensity falls), D95% (the maximum particle diameter below which 95% of sample intensity falls), and D99% (the maximum particle diameter below which 99% of sample intensity falls). Thus, based on the methodology presented in ISO 22412, it is possible to ascertain that at least 95% (D95) or preferably 90% (D90) of particles comprised in the composition of the present invention has a diameter of less than or equal to 600 nm, more preferably less than or equal to 300 nm, and that said particles have a z-average diameter of less than or equal to 200 nm, more preferably less than 150 nm.

In a preferred embodiment of the composition of the present invention, said particles have a mono-modal diameter distribution, in particular within the sub-micrometer range indicated above. Indeed, in one aspect the aqueous composition of the present invention comprises particles wherein at least 90% of said particles has a mono-modal diameter distribution below 300 nm, wherein said particles have a z-average diameter of less than or equal to 150 nm, as measured according to ISO 22412. Particles (or their aggregates) having a size superior to such values (e.g. in the micrometer range, such as above 10 µm) that may be still present (but, in any case below the limits indicated in European Pharmacopoeia) can be removed by filtration, at the end of manufacturing and/or just before administration (for example, through 0.8 micrometer filter). Thus, all or the large majority of particles comprised in this composition may present a mono-modal diameter distribution within the composition that, as shown in the Examples, is established during their preparation and can be maintained and adapted according to the desired use and/or storage.

In another preferred embodiment of the present invention at least 95% or 90% of said particles has a diameter of less than or equal to 600 nm (i.e. the maximum particle diameter below which 95% or 90% of sample intensity falls=D95% or D90%=600 nm), more preferably not exceeding the diameter of 500 nm, still more preferably not exceeding the diameter of 400 nm, and yet more preferably not exceeding the diameter of 300 nm. Within such limits, Even more preferably, at least 99% of said particles has a diameter of less than or equal to 600 nm, yet more preferably at least 99% of said particles has a diameter of less than or equal to 500 nm, much more preferably at least 99% of said particles has a diameter of less than or equal to 400 nm and yet more preferably not exceeding the diameter of 300 nm. On the other hand, in a preferred embodiment, said particles have a median diameter (D50%) between 75 and 150 nm, more preferably between 80 and 130 nm, and a D90% of between 140 and 250 nm, more preferably between 170 and 240 nm.

In another preferred embodiment of the present invention, said particles have a z-average diameter below 150 nm, and more preferably in ranges comprised between 30 nm and 150 nm (such as furthermore preferably between 50 nm and 150 nm, between 75 nm and 150 nm, between 50 nm and 100 nm, between 100 nm and 150 nm, or between 60 nm and 130 nm). More preferably, said particles of the aqueous composition of the present invention have a mono-modal diameter distribution between 30 nm and 150 nm.

Thus, in most particularly preferred embodiments: (i) at least 99% of particles comprised in the composition of the present invention have a diameter of less than or equal to 600 nm, whereby said particles have a z-average diameter of between 30 nm and 150 nm; and (ii) at least 99% of particles comprised in the composition of the present invention have a diameter of less than or equal to 500 nm, whereby said particles have a z-average diameter of between 60 nm and 130 nm and have a median diameter (D50%) between 75 and 150 nm.

In a preferred embodiment of the present invention, said composition is obtainable by lyophilisation of the aqueous compositions disclosed herein. Thus, the composition of the invention may be an aqueous or a lyophilised composition. Thus, the composition of the present invention (hereinafter BO-11X formulation, where X may be a whole number such that a BO-11X formulation encompasses, for example, a BO-111 and a BO-112 formulation) can be provided in a solid (as a lyophilized or other highly concentrated form of the particles), semi-solid (as a gel), or liquid form, but is preferable as a liquid composition (such as an aqueous composition or other type of particle suspension that can be injected or inhaled). The BO-11X formulations can be used, shipped, and stored as such, or can be used for obtaining a lyophilized form for specific uses, shipment, storage, administration with other compounds, and/or further technical requirements. With respect to the lyophilisation process and equipment, classical freeze-drying or more recent methods (such as electro-freezing, ultrasound-controlled or ice fog), may be adapted for handling and manufacturing of the BO-11X formulations, also by changing parameters such as pH, drying air speed, time, humidity, pressure, or temperature.

Thus, in one most preferred embodiment, the composition of the present invention comprises particles wherein:
(i) each of said particles comprises a complex of at least one double-stranded polyribonucleotide, or a salt or solvate thereof, and at least one polyalkyleneimine, or a salt and/or solvate thereof, wherein
  (a) said double-stranded polyribonucleotide is polyinosinic-polycytidylic acid [poly(I:C)] or polyadenylic-polyuridylic acid [poly(A: U)], wherein at least 60% of said double-stranded polyribonucleotides have at least 850 base pairs, at least 70% of said double-stranded polyribonucleotides have between 400 and 5000 base pairs, and between 20% and 45% of said double-stranded polyribonucleotides have between 400 and 850 base pairs; and (b) said polyalkyleneimine comprises at least 95% polyethyleneimines, wherein the average molecular weight of said polyalkyleneimine is between 17 and 23 kDa and the polydispersity index is <1.5, and wherein the ratio of the number of moles of nitrogen of said polyalkyleneimine to the number of moles of phosphorus of said double-stranded polyribonucleotide used in formation of said composition (i.e. the ratio of the number of moles of nitrogen of said polyalkyleneimine to the number of moles of phosphorus of said double-stranded polyribonucleotide used in formation of said particles) is between 2.5 and 5.5;

(ii) at least 99% of said particles has a diameter of less than or equal to 600 nm, preferably at least 95% of said particles has a diameter of less than or equal to 400 nm; and (iii) said particles have a z-average diameter of between 30 nm and 150 nm.

In another most preferred embodiment, the composition of the present invention is an aqueous composition which comprises particles wherein:

(i) each of said particles comprises a complex of at least one double-stranded polyribonucleotide, or a salt or solvate thereof, and at least one polyalkyleneimine, or a salt and/or solvate thereof, wherein
  (a) said double-stranded polyribonucleotide is polyinosinic-polycytidylic acid [poly(I:C)], wherein at least 60% of said poly(I:C) has at least 850 base pairs, at least 70% of said poly(I:C) has between 400 and 5000 base pairs, and between 20% and 45% of said poly(I:C) has between 400 and 850 base pairs; and
  (b) said polyalkyleneimine is polyethyleneimine (PEI), wherein the weight average molecular weight of said PEI is between 17.5 and 22.6 kDa and the polydispersity index is <1.5, and wherein the ratio of the number of moles of nitrogen of said polyalkyleneimine to the number of moles of phosphorus of said double-stranded polyribonucleotide used in formation of said composition (i.e. the ratio of the number of moles of nitrogen of said polyalkyleneimine to the number of moles of phosphorus of said double-stranded polyribonucleotide used in formation of said particles) is between 2.5 and 4.5;

(ii) at least 99% of said particles has a diameter of less than or equal to 500 nm, preferably at least 95% or 90% of said particles has a mono-modal diameter distribution below 300 nm;

(iii) said particles have a z-average diameter of between 60 nm and 130 nm; and (iv) said particles have a median diameter (D50%) between 75 and 150 nm.

The BO-11X formulations can, in a preferred embodiment of the present invention, be provided as compositions further comprising a pharmaceutically acceptable carrier, excipient, organic solvent, and/or adjuvant [such as glycerol, ethanol, glucose or mannitol, preferably glucose or mannitol, more preferably in a concentration of between 1 and 10% (weight/volume)] [i.e, wherein said composition is formed by additionally adding glucose or mannitol in a concentration of between 1 and 10% (weight/total volume of said composition)] that is best adapted to the preferred final form (such as liquid or lyophilised), uses, shipment, storage, administration with other compounds, and/or further technical requirements. In a more preferred embodiment, said composition further comprises at least one compound selected from an organic compound, an inorganic compound, a nucleic acid, an aptamer, a peptide or a protein.

In one aspect, the aqueous composition of the present invention has a zeta potential equal or superior to 30 mV, preferably between 35 and 50 mV or between 38 and 45 mV, still more preferably between 40 and 45 mV, according to ISO 13099.

In another embodiment of the composition of the present invention, said composition is an aqueous composition that has:
  (i) a pH of between 2 and 4;
  (ii) an osmolarity of between 200 and 600 mOsm/kg;
  (iii) a specific optical rotation of between +1500 and +3750 degrees·mL·g$^{-1}$·dm$^{-1}$ at a wavelength of 589 nm at 20° C. when said aqueous composition comprises 5% (weight/volume) D-glucose in water, referenced against water; and/or
  (iv) a zeta potential greater than or equal to 30 mV (for instance, comprised between 35 and 50 mV).

In an even more preferred embodiment of the present invention, said composition is an aqueous composition that has:
  (i) a pH of between 2 and 4;
  (ii) an osmolarity of between 200 and 600 mOsm/kg; and/or
  (iii) a zeta potential greater than or equal to 30 mV (for instance, comprised between 35 and 50 mV).

In one especially preferable embodiment said composition is an aqueous composition comprising glucose or mannitol that has:
  (i) a pH of between 2 and 4; and/or
  (ii) an osmolarity of between 200 and 600 mOsm/kg.

In one, furthermore preferable embodiment of the present invention, said composition is an aqueous composition comprising glucose that has:
  (i) a pH of between 2.7 and 3.4;
  (ii) an osmolarity of between 200 and 340 mOsm/kg; and/or
  (iii) a zeta potential comprised between 35 and 50 mV or between 38 and 45 mV, still more preferably between 40 and 45 mV.

In an alternative, furthermore preferable embodiment said composition is an aqueous composition comprising mannitol that has:
  (i) a pH of between 2.7 and 3.4;
  (ii) an osmolarity of between 200 and 600 mOsm/kg; and/or
  (iii) a zeta potential comprised between 35 and 50 mV or between 38 and 45 mV, still more preferably between 40 and 45 mV.

For the purposes of the present invention, the osmolarity values reported herein are strictly olmolality values, but since the density of water (the solvent in which the aqueous compositions of the present invention are made) approximates to 1.00 g/mL at 20° C. these terms are used interchangeably. For the purposes of the present invention, room temperature refers to a temperature between 2° and 25° C.

In the present invention, the zeta potential is measured according to ISO 13099, preferably 13099-2:2012.

The present invention also relates to a composition, as disclosed herein, for use as a medicament. Analogously, the present invention therefore also relates to use of the composition, as disclosed herein, for the manufacture of a medicament. This use may be achieved by providing the composition as liquid (aqueous) or lyophilised composition wherein poly(I:C) molecules and the particles comprising it are in a highly stable form and at high concentration {e.g, wherein said composition is formed by making a complex using at least 0.5 mg, 0.7 mg/mL, 0.9 mg/ml, up to 2.0 mg of polyinosinic-polycytidylic acid [poly(I:C)] or polyadenylic-polyuridylic acid [poly(A: U)] or more per mL of the total (i.e. final) volume of said composition.

These compostions are particularly adapted for direct administration to the cancer cells, for example by means of intratumoral or peritumoral injection into skin or an internal organ or tissue comprising such tumors and cancer cells. In a preferred embodiment of the present invention, said medicament is injectable. In a more preferred embodiment of the present invention, said medicament is an injectable, aqueous composition, optionally comprising a pharmaceutically acceptable carrier, excipient and/or adjuvant. This injectable, aqueous composition can be provided as such or after diluting a concentrated preparation of poly(I:C) or poly(A: U) molecules (at a respective concentration of at least 0.5 mg of poly(I:C) or poly(A: U)/mL of the total volume of composition to be made, or more, as established when preparing the particles in terms of the respective weight of poly(I:C) or poly(A: U) molecules that are added to a given volume of solution) or a lyophilised composition in order to make up a total volume of the composition of the invention. This means that said composition is provided in the foregoing concentrations determined in terms of the weight of poly(I:C) or poly(A: U) employed in making the complex per volume of the total aqueous composition, but may be concentrated where appropriate, especially for long-term storage and/or intratumoral administration. In particular, the BO-11X formulation with double-stranded poly(I:C) molecules at such high concentrations (i.e. that made from particles comprising a complex formed by complexing at least 0.5 mg up to 0.7 mg, preferably 0.9 mg, more preferably 2.0 mg or more, of poly(I:C) with linear PEI per mL of the total aqueous composition) is most appropriate for administration and use as a medicament. The intratumoral or peritumoral injection of such a composition (depending also on the actual accessibility and/or size of the tumor mass as evaluated by the practitioner) in one or more small or restricted locations where tumors and cancer cells are present, may provide a stronger and/or more timely therapeutic effect.

Moreover, the present invention additionally relates to a composition, as disclosed herein, for use in treatment of a cell growth disorder characterized by abnormal growth of human or animal cells. Such treatment may involve the combined administration of the composition of the present invention with another therapeutic treatment such as another cancer-specific drug (being an antibody targeting a cancer antigen or a cancer vaccine, for example) or a standard-of-care treatment (such as radio- or chemotherapy). The combined administration may provide not only an additive therapeutic effect but also other valuable effects such as reduce the dosage of the other drug necessary to achieve a similar therapeutic benefit, reduce side effects, or provide a longer-lasting and/or a synergistic effect on tumors and cancer cells. Analogously, the present invention therefore also relates to use of the composition, as disclosed herein, for the manufacture of a medicament for the treatment of a cell growth disorder characterized by abnormal growth of human or animal cells. For the purposes of the present invention, abnormal growth is characterized by uncontrolled cell division and/or differentiation.

In a more preferred embodiment, said cell growth disorder is cancer or a gynaecological disorder characterized by abnormal growth of cells of the female mammal reproductive organs. The cancer referred to in the present invention is preferably one or more of basal cell carcinoma; biliary tract cancer; bladder cancer; bone cancer; brain and central nervous system cancer; breast cancer; cancer of the peritoneum; choriocarcinoma; connective tissue cancer; cancer of the digestive system (including esophageal, stomach, colon, rectal or other gastrointestinal cancer); eye cancer; cancer of the head and neck; glioblastoma; hepatic carcinoma; hepatoma; intra-epithelial neoplasm; kidney, adrenal, or renal cancer; leukaemia; liver cancer; lung cancer (e.g., small-cell lung cancer, non-small cell lung cancer, lung adenocarcinoma, and lung squamous carcinoma); melanoma; myeloma; neuroblastoma; oral cavity cancer (e.g. lip, larynx, tongue, mouth or pharyngeal cancer); pancreatic cancer; prostate cancer; retinoblastoma; rhabdomyosarcoma; cancer of the respiratory system; salivary gland carcinoma; skin cancer; squamous cell cancer; testicular cancer; thyroid cancer; uterine, endometrial, cervical, vulval, ovarian or other gynaecological cancer; cancer of the urinary system; lymphoma including B-cell lymphoma, Hodgkin's and non-Hodgkin's lymphoma (NHL; including specific types such as low grade/follicular, small lymphocytic, intermediate grade/follicular, intermediate grade diffuse, high grade immunoblastic, high grade lymphoblastic, high grade small non-cleaved cell, or bulky disease NHL); mantle cell and AIDS-related lymphoma; chronic lymphocytic leukaemia; acute lymphoblastic leukaemia; Hairy cell leukaemia; chronic myeloblastic leukaemia; as well as other carcinomas and sarcomas; post-transplant lymphoproliferative disorder (PTLD), as well as abnormal vascular proliferation associated with phakomatoses or oedema (such as those that associated with brain tumors). More preferably, said cancer is selected from one or more of bladder cancer; bone cancer; brain and central nervous system cancer; breast cancer; cancer of the digestive system (including esophageal, stomach, colon, rectal or other gastrointestinal cancer); cancer of the head and neck; glioblastoma; hepatic carcinoma; hepatoma; kidney, adrenal, or renal cancer; leukaemia; liver cancer; lung cancer; melanoma; myeloma; neuroblastoma; pancreatic cancer; prostate cancer; cancer of the respiratory system; skin cancer; testicular cancer; thyroid cancer; uterine, endometrial, cervical, vulval, ovarian or other gynaecological cancer; cancer of the urinary system; lymphoma or leukaemia. Still more preferably, said cancer is selected from one or more of a carcinoma, glioma, melanoma or sarcoma, even more preferably melanoma, prostate cancer, colon cancer, breast cancer or pancreatic cancer, or alternatively melanoma or pancreatic cancer.

The female mammal reproductive organs referred to in the present invention are the female mammal sex organs located between the vagina and falliopian tubes, inclusive. Said reproductive organs of the present invention are the uterus, fallopian tubes (comprising the utero-tubal junction), ovaries, cervix and vagina, preferably the uterus, fallopian tubes, and cervix, more preferably the mammalian uterus. Therefore, the gynaecological disorder of the present invention is a disease which affects at least one cell of the female mammal reproductive tract located between the vagina and fallopian tubes, preferably the uterus, fallopian tubes and cervix. In the present invention, a gynaecological disorder is more preferably a disease which affects at least one cell in a tissue of the mammalian uterus. In a most preferred embodiment, the gynaecological disorder is selected from endometriosis or leiomyoma.

In the present invention, the mammal is preferably hominine, bovine, equine, canine, feline, ovine, porcine, camelline, caprine or cervine. Furthermore preferably, said mammal is a human, dog, cow, horse or camel, even more preferably a human or dog, and most preferably a human.

Thus, the BO-11X formulations can present a combination of components and other physico-chemical features that provide effects of medical interest (such as for treating of cancers such melanoma, or carcinomas) and that, preferably, can be obtained by applying a process compatible with regulatory and industrial requirements such as those applicable to drug manufacturing. In particular, BO-11X production stages are carried out in strict compliance with the requirements of Good Manufacturing Practices in force in Europe (specifically Annex 13), USA, Japan, and/or other countries, and/or with the requirements for the approval of Investigational Medicinal Product Dossier (IMPD). BO-11X formulations should pass tests for sterility, purity, stability and biosafety (absence or substantially free of endotoxins, virus, bacteria, chemicals, metals, or other contaminants that are incompatible with use in humans). For instance, endotoxin level should be no more than 1.0 EU/mg or 1 µg/mL, using officially approved detection kits . . .

Such components and features further characterizing BO-11X formulations, (as composition or particles comprised herein), may be one or more of the following ones:

(i) A composition comprising pharmaceutically acceptable carrier, excipient and/or adjuvant, with or without any further organic compound (such a solvent), inorganic compound, nucleic acid, aptamer, peptide or protein having medical interest that is comprised in the particles themselves (for example, during their manufacturing) or later added into the composition comprising these particles;

(ii) Particles formed by a polyalkyleneimine (such as linear PEI), in particular having a weight average molecular weight between 17 and 23 kDa, more preferably between 17.5 and 22.6 kDa;

(iii) A composition comprising particles formed by making a complex using double-stranded polyribonucleotides at a concentration of at least 0.5 mg/ml of the total (i.e. final) volume of said composition (for instance, from 0.5 mg/ml up to 0.7 mg/mL, 0.9 mg/ml, 2 mg/mL or more);

(iv) Particles comprising a polyalkyleneimine and double-stranded polyribonucleotides that are formed at a ratio of the number of moles of nitrogen of said polyalkyleneimine to the number of moles of phosphorus of said double-stranded polyribonucleotide (i.e. the ratio of the number of moles of nitrogen of said polyalkyleneimine to the number of moles of phosphorus of said double-stranded polyribonucleotide used in formation of said particles) is equal to or greater than 2.5, more preferably between 2.5 and 5.5, still more preferably between 2.5 and 4.5, furthermore preferably between 2.5 and 3.5.;

(v) Particles having a mono-modal diameter distribution with an Z-average diameter, as defined herein and measured according to ISO 22412, preferably below 200 nm, more preferably below 150 nm, and even more preferably in ranges comprised between 150 nm and 30 nm (such as between 150 nm and 50 nm, between 150 nm and 75 nm, between 100 nm and 50 nm, between 150 nm and 100 nm, or between 60 nm and 130 nm);

(vi) Particles having a mono-modal diameter distribution, determined from the diameter distribution according to ISO 22412, that is represented by D values D50% (the maximum particle diameter below which 50% of sample intensity falls, also known as the median diameter) between 75 and 150 nm and D90% (the maximum particle diameter below which 90% of sample intensity falls) between 140 and 250 nm;

(vii) At least 95% of particles have a diameter of 600 nm, preferably a diameter of 500 nm, more preferably a diameter of 400 nm, and even more preferably a diameter of 300 nm. Yet more preferably, at least 90% of particles have a mono-modal diameter distribution below 300 nm;

(viii) A composition presenting an osmolarity comprised between 200 and 600 mOsm/kg, preferably an aqueous composition comprising 5% (weight/volume) glucose presenting an osmolarity comprised between 200 and 400 mOsm/kg, more preferably between 260 and 340 mOsm/kg;

(ix) A composition presenting a pH comprised between 2.7 and 3.4;

(x) An aqueous composition comprising 5% (weight/volume) D-glucose presenting a specific optical rotation between +1500 and +3750 degrees·mL·g$^{-1}$·dm$^{-1}$ at a wavelength of 589 nm at 20° C. at a wavelength of 589 nm at 20° C. in water, referenced against water; and/or (xi) A composition presenting a zeta potential equal or superior to 30 mV, such as 38 mV, preferably comprised between 35 and 50 mV, or more preferably comprised between about 40 and 45 mV (e.g. 43 mV), as defined herein and measured according to ISO 13099.

In a preferred embodiment, the present invention may relate to compositions, in particular for pharmaceutical use, comprising particles wherein said particles comprise complexes of double-stranded polynucleotides with a water-soluble, polycationic homo- or hetero-polymer wherein said particles are characterized by a mono-modal diameter distribution that is defined by having a diameter of less than or equal to 600 nm, preferably less than or equal to 300 nm and a z-average diameter of less than or equal to 200 nm, preferably less than or equal to 150 nm.

In another preferred embodiment, the double-stranded polyribonucleotides are poly(I:C) molecules that are present in the BO-11X formulations result from the annealing of polyinosinic acid [poly(I)] molecules and polycytidylic acid [poly(C)] single-stranded molecules that have themselves specific ranges of percentages for sizes below 0.4 Kb, between 0.4 Kb and 0.85 Kb, between 0.85 Kb and 5.0 Kb, and above 5.0 Kb as indicated in the Examples which also provides means for generating an aqueous solution of poly (I:C) molecules (already containing or not an excipient such as glucose or mannitol) and have appropriate features for being mixed with aqueous solution of a polyalkyleneimine (such as polyethyleneimine) for producing the BO-11X formulations. The poly(I:C)-containing formulation resulting from mixing these two aqueous solutions is then maintained as a batch preparation (preferably still as a aqueous solution or in a lyophilized form) or can be directly prepared in aliquots, each contained in a single-use vials, syringes, or other appropriate container for storage, single use of such aliquots, and/or lyophilisation. BO-11X formulations (in a liquid or lyophilized form) can be stored at room temperature or a temperature below 0° C. or below −20° C.

In such preferred embodiment, further compounds (such as one or more antibody, hormone, peptide, excipient, carrier, inhibitor of an enzymatic activity, chemotherapeutic agent, antibiotic, stabilizing agent, labelling agent, organic solvent, preservatives, carriers, or other drug) can be either added in each of the two aqueous solutions (if not altering the correct formation of the particles or any other of the features listed above for BO-11X formulations) prior to their mixing or after that BO-11X formulation has been produced by mixing the two aqueous solutions (of double-stranded polyribonucleotide and polyalkyleneimine). Such additional components that are consequently administered at the same time with BO-11X components can provide a composition with improvements in the bioavailability, efficacy, pharmacokinetic/pharmacodynamic profiles, stability, metabolization, or other property of pharmaceutical interest that are not observed when each of initial BO-11X formulation or the additional component (another compound of pharmaceutical interest, for instance) is administered alone, or each of initial BO-11X formulation or the additional component are administered separately.

In a further preferred main embodiment, the BO-11X formulation is for use as a medicament, such as a pharmaceutical composition that is formulated (e.g. as an injectable, aqueous composition, optionally comprising a pharmaceutically acceptable carrier, excipient and/or adjuvant) and administered for the delivery of double-stranded polyribonucleotides to an organ or a tissue in a healthy state, presenting a disease related to a exogenous pathogenic agent (such a bacteria or a virus), or presenting an alteration due to a cell growth disorder characterized by abnormal growth of human or animal cells for instance, due to cancer (that is, involving tumorogenic transformation, metastasis, toxic compound), or a gynaecological disorder characterized by abnormal growth of cells of the female mammal reproductive organs). Thus, in a preferred embodiment, the present invention relates to a method of treatment of a disease comprising administering the composition of the present invention to a human or animal. In a further preferred embodiment, the present invention relates to a method of treatment of a cell growth disorder characterized by abnormal growth of human or animal cells, as defined herein, comprising administering the composition of the present invention to a human or animal.

Preferably, the BO-11X formulation is used in methods for inducing (directly or indirectly) the death of the tumor cell or suppress growth of the tumor cell, at scope of treating, reducing, ameliorating, or preventing cancer growth, survival, metastasis, epithelial-mesenchymal transition, immunologic escape or recurrence. More preferably, BO-11X formulations are used in methods for treating solid tumors, such as carcinomas, gliomas, melanomas, or sarcomas. In particular, the BO-11X formulation is administered either systemically or more directly within or in a location near to the tumor such as at the margin of the tumor mass, in the surrounding epithelial cells, lymphatic or blood vessels (e.g. by intratumoral or peritumoral injection), or the abnormally growing cells of female mammal reproductive organs.

In some embodiments, the BO-11X formulation is the one produced according to the manufacturing methods, and then defined structurally and functionally, as described in the Examples as BO-111 or BO-112 formulations. The BO-11X formulation can further exhibit the biological activities that were characterized for BO-110 as described in WO2011003883, namely activation of a family helicase MDA-5 or the level of NOXA expression, in combination with the induction of autophagy in cancer cells or in a cell line derived from cancer cells, preferably from a human origin, albeit to an improved degree. Examples of cell lines for validating BO-11X formulations are human SK-Mel-19, SK-Mel-28, SK-Mel-103 and SK-Mel-147 cells, and the murine B16 cells, said melanoma cell lines presenting an increased expression of molecules such as Interferon Beta when exposed to a BO-11X formulation. Additionally, the BO-11X formulation presents no toxicity against normal cells that are used as controls, such as melanocytes or other skin cells, as well as cells of the immune system, which usually represent sites of secondary toxicity in cancer treatment. The BO-11X formulation may also, following the autophagy and apoptosis of cancer cells (or any other effect of therapeutic interest that this formulation may induce in such cells), induce the release of cancer cell antigens that may act as inducers of a tumor-specific immunological response, in particular when BO-11X formulation is administered locally to cancerous cells or tumors (e.g. by peritumoral or intratumoral injection, administering BO-11X at the margin of tumor mass, in surrounding epithelial cells, lymphatic or blood vessels, or directly within the tumor mass), with or without the simultaneous or sequential administration of another drug or other treatment for same indication.

The present invention also relates to a process to manufacture the composition, as disclosed herein, which comprises:
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 500 nm to form sterilized solutions;
(iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and optionally
(iv) filtering the resulting aqueous composition through a filter having a pore diameter of less than or equal to 600 nm to form a filtrate, or centrifuging the resulting aqueous composition at greater than or equal to 22480 m/s$^2$ to form a supernatant; and/or
(v) lyophilising the resulting aqueous composition, filtrate or supernatant.

Thus, in one preferred embodiment, the present invention may relate to a process to manufacture the composition, as disclosed herein, which comprises:
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 500 nm to form sterilized solutions; and
(iiii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and (iv) optionally lyophilising the resulting aqueous composition.

In addition, in another preferred embodiment, the present invention may relate to a process to manufacture the composition, as disclosed herein, which comprises:
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 500 nm to form sterilized solutions;
(iii) mixing the resulting sterilized solutions in a mixing chamber to form an aqueous composition by addition of one of said solutions into the other solution in said mixing chamber, optionally by injection, at a rate of greater than or equal to 1 mL/min, or by simultaneous addition of each of said solutions into said mixing chamber, optionally by injection, at a rate of greater than or equal to 1 mL/min; and (iv) filtering the resulting aqueous composition through a filter having a pore diameter of less than or equal to 600 nm to form a filtrate, or centrifuging the resulting aqueous composition at greater than or equal to 22480 m/s$^2$ to form a supernatant; and
(v) optionally lyophilising the resulting filtrate or supernatant More preferably, the process of the present invention does not comprise a final step of lyophilisation. In the process of the present invention, said double-stranded polyribonucleotide, said polyalkyleneimine and said pharmaceutically acceptable carrier, organic solvent, excipient and/or adjuvant are as disclosed herein. Sterilizing each solution to form sterilized solutions takes place by independently filtering said solutions through a filter having a pore diameter of less than or equal to 500 nm, preferably by independently filtering said solutions through a filter having a pore diameter of less than or equal to 300 nm, more preferably by filtering said solutions through a filter having a pore diameter of less than or equal to 200 nm.

Preferably the mixing of the resulting filtrates takes place through the large-scale convective transport of eddies and subsequently through elimination of concentration differences through purely diffusive transport. The mixing chamber may be any chamber or vessel in which the mixing of said solutions begins, such as a flask, reactor or mixer. More preferably, said mixing chamber has a fixed volume of between 0.1 and 20 mL, furthermore preferably between 0.2 and 10 mL, much more preferably between 0.5 and 8 mL. More preferably, mixing takes place by addition, optionally by injection, at a rate of between 1 mL/min and 2000 mL/min, still more preferably at between 10 and 1000 mL/min, furthermore preferably at between 20 and 500 mL/min. Optional filtering of the resulting aqueous composition to form or collect a filtrate may subsequently be performed through a filter having a pore diameter of less than or equal to 600 nm, preferably not exceeding the diameter of 500 nm, more preferably not exceeding the diameter of 400 nm, yet more preferably not exceeding the diameter of 300 nm. Alternatively, optional centrifuging of the resulting aqueous composition to form or collect a supernatant may subsequently be performed at greater than 22480 m/s$^2$ (5000 rpm on a rotor having a radius of 0.082 m), preferably at greater than 27202 m/s$^2$ (5500 rpm on a rotor having a radius of 0.082 m), more preferably at greater than 32372 m/s$^2$ (6000 rpm on a rotor having a radius of 0.082 m), yet more preferably 44062 m/s$^2$ (7000 rpm on a rotor having a radius of 0.082 m). In one especially preferred embodiment step (iv) is obligatory when the composition of the present invention is not achieved by steps (i) to (iii) of the process of the present invention, namely when addition is carried out at such that a rate that less than 95% of the particles comprised in said aqueous composition has a diameter of less than or equal to 600 nm; and/or said particles have a z-average diameter of greater than 200 nm, more preferably when said particles do not have a monomodal diameter distribution. This may be the case when addition is performed at a rate of between 1 mL/min and 20 mL/min, particularly in a reaction chamber of between 0.5 and 20 mL. Finally, the resulting aqueous composition, filtrate or supernatant may be subjected to lyophilisation to afford the composition of the present invention as a particulate solid.

Thus, in one much more especially preferred embodiment of the process of the present invention, said process comprises
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 200 nm to form sterilized solutions;
(iii) mixing the resulting sterilized solutions in a mixing chamber to form an aqueous composition by addition of one of said solutions into the other solution in said mixing chamber, optionally by injection, at a rate between 20 mL/min and 100 mL/min, or by simultaneous addition of each of said solutions into said mixing chamber, optionally by injection, at a rate between 20 mL/min and 100 mL/min, wherein said mixing chamber has a volume of between 0.2 and 10 mL;
(iv) filtering the resulting aqueous composition through a filter having a pore diameter of less than or equal to 500 nm to form a filtrate, or centrifuging the resulting aqueous composition at greater than or equal to 32372 m/s$^2$ (6000 rpm on a rotor having a radius of 0.082 m) to form a supernatant; and
(v) optionally lyophilising the resulting filtrate or supernatant.

In another even much more especially preferred embodiment of the process of the present invention, said process comprises
(i) preparing an aqueous solution of at least one double-stranded polyribonucleotide, or a salt or solvate thereof, and an aqueous solution of at least one polyalkyleneimine, or a salt or solvate thereof, wherein either or both solutions optionally further comprise a pharmaceutically acceptable carrier, organic solvent, excipient and/or adjuvant;
(ii) independently filtering each solution through a filter having a pore diameter of less than or equal to 200 nm to form sterilized solutions;
(iii) mixing the resulting sterilized solutions in a mixing chamber to form an aqueous composition by addition of one of said solutions into the other solution in said mixing chamber, optionally by injection, at a rate between 30 mL/min and 100 mL/min, or by simultaneous addition of each of said solutions into said mixing chamber, optionally by injection, at a rate between 30 mL/min and 100 mL/min, wherein said mixing chamber has a volume of between 0.5 and 8 mL; and (vi) optionally lyophilising the resulting aqueous composition.

In a further embodiment, the BO-11X formulation is produced according to a manufacturing process that involves the mixing of two aqueous solutions, a first one comprising the double-stranded polyribonucleotides (or a salt or solvate thereof) and a second one comprising the polyalkyleneimine (or a salt or solvate thereof) so that the resulting particles present the features defined above, in particular with respect to the diameter and the mono-modal diameter distribution as well the appearance as an essentially clear colloidal solution.

As described with further details in the Examples, the BO-11X formulations can be provided by filtering and/or centrifuging pharmaceutical composition comprising particles formed by double-stranded polyribonucleotides and a water-soluble, polycationic homo- or hetero-polymer, providing the BO-11X formulations as bulk or single use liquid compositions without visible aggregates. Such a process to manufacture the composition comprises:

(i) preparing an aqueous solution of at least one double-stranded polyribonucleotide, or a salt or solvate thereof, and an aqueous solution of at least one polyalkyleneimine, or a salt or solvate thereof, optionally together with a pharmaceutically acceptable carrier, organic solvent, excipient and/or adjuvant present in either solution;

(ii) mixing said solutions; and (iii) filtering the resulting mixture through a filter having a pore diameter of less than or equal to 600 nm, or centrifuging at greater than 22480 m/s$^2$.

This process can be further adapted for the actual components of the composition (double-stranded polyribonucleotides, the polyalkyleneimine, and optional further components) as well the desired methods of using, storing, shipping, packaging, and/or administering the composition, in particular if the composition requires to be manufactured immediately prior to the use or, as is more common for pharmaceutical compositions, manufactured for long-term storage and/or in the form of multiple containers each one for a single-use (e.g. in sterile vials or syringes), and containing particles having the most uniform size, poly(I: C) content, stability, solubility, and, finally, biological effects when administered.

At this scope, the mixing and filtering steps (ii) and (iii) above can be adapted at the level of order of filtering and/or mixing, method of mixing, the mixing speed, and/or the amount of solutions that is mixed. In a further preferred embodiment, the process to manufacture BO-11X formulations comprises:

(i) preparing an aqueous solution of at least one double-stranded polyribonucleotide, or a salt or solvate thereof, and an aqueous solution of at least one polyalkyleneimine, or a salt or solvate thereof, optionally together with a pharmaceutically acceptable carrier, organic solvent, excipient and/or adjuvant present in either solution;

(ii) sterilizing each solution by filtering them independently;

(iii) mixing said solutions in the container for storing, lyophilising, and/or using the composition by adding either solution first and then adding the other solution at an injection speed superior to 50 rpm at a flow speed between 1 mL/min and 50 mL/min; and (iv) sealing the container.

Combinations

A composition according to the present invention can be used in combinations including other compounds or treatments with which it is known to be compatible, if not providing an additive or even synergistic effect. For instance, poly(I:C) molecules can be used in combination with different anti-cancer drugs, antibodies, radiotherapy, or chemotherapy (Le U et al., 2008; Le U et al., 2009; Taura M et al., 2010; Matijević T et al., 2011; Levitzki A, 2012; Yoshino H and Kashiwakura I, 2013; Hafner A et al., 2013) or different length of poly(I:C) molecules (Zhou Y et al., 2013). Poly(I:C) molecules have also been used as an adjuvant or synergically-acting agent when combined with other agents such as in vaccination with cancer antigens or cell lysates (Ammi R et al., 2015), agents blocking PD-1/PD-L1 pathway (Nagato T and Celis E, 2014), other TLR agonists, such as TLR9 agonist CpG ODN (Zhang Y et al., 2014), dichloroacetate (Ohashi T et al., 2013), IL27 (Chiba Y et al., 2013), kinase inihibitors such as sorafenib (Ho V et al.,2015), proapoptotic proteins such as NS1 (Gupta S et al. 2016), Zoledronic acid (Chen L et al., 2013), or all-trans retinoic acid (Szabo A et al., 2012). Other uses of BO-11X formulations may become apparent in view of activities of poly(I:C) molecules towards specific cell types recently demonstrated, at least using in vitro assays, such as on pre-adipocytes, inhibiting differentiation and differentiation in adipocytes (Yu L et al., 2016), mesenchymal stem cells, enhancing immunosuppressive effects (Cho K. et al., 2016; Vega-Letter A et al., 2016), or activation of NK cells (Perrot I et al., 2010).

In some aspects, the present invention relates to a pharmaceutical composition comprising an effective amount of a BO-11X formulation and an effective amount of one or more immune-modulating agents, in particular agents that target immune checkpoint molecules (such as PD-1, PD-L1, PD-L2, CTLA-4, CD134, CD134L, CD137, CD137L, CD80, CD86, B7-H3, B7-H4, B7RP1, LAG3, ICOS, TIM3, GAL9, CD28, AP2M1, SHP-2, PPP2R5A or OX-40), said compounds commonly named as checkpoint inhibitors (CPIs).

Accordingly, the present invention provides compositions and methods that are useful in combination therapies and regimens comprising the administration of BO-11X formulations and another therapeutic agent or treatment (including radiotherapy, chemotherapy, cryotherapy, tumor ablation, or photodynamic therapy). In particular, the present invention relates to a method for treating, ameliorating, or preventing cancer growth, metastasis, ulceration, immunologic escape or recurrence in a subject, comprising administering a BO-11X formulation and one or more anticancer drug, preferably an immune-modulating agent, wherein the administration is simultaneous (as separate formulations or in the context of a co-formulation) or sequential (in any order or in consecutive cycles of administration). In some aspects, the present invention relates to a method for treating cancer, comprising administering an effective amount of BO-11X formulation agent and an effective amount of one or more immune-modulating agents to a subject in need thereof, in particular wherein the subject is undergoing cancer therapy with one or more immune-modulating agents.

In various embodiments, the immune-modulating agent is preferably an antibody including a monoclonal antibody and other antibody formats, or any other pharmaceutically available agent that binds a cell surface protein that control immune response, thus acting as a CPI, This CPI can block, reduce and/or inhibit PD-1 and PD-L1 or PD-L2 and/or the binding of PD-1 with PD-L1 or PD-L2. Alternatively, this CPI can block, reduce and/or inhibit reduces and/or inhibits the activity of other immune checkpoint molecules such as CTLA-4, AP2M1, CD80, CD86, SHP-2, and/or PPP2R5A As a further alternative, the CPI increases and/or stimulates CD137 (4-1BB) and/or the binding of CD137 (4-1BB) with one or more of 4-1BB ligand and TRAF2.

In various embodiments, the methods involving combination therapies and regimens for the treatment of cancer comprising the administration of BO-11X formulations may further defined with respect to a specific administration method, wherein the BO-11X formulation is administered by a route different form the one of the other therapeutic compound, such as an immune-modulating agents, and preferably a CPI. This method may involve administering the BO-11X formulation by intratumoral or peritumoral injection (within the tumor, at the margin of the tumor mass, in the surrounding epithelial cells, lymphatic or blood vessels) or other means that allow administering the BO-11X formulation directly within or in proximity of cancer cells or organ comprising the cancer cells (and not indirectly, for instance through bloodstream) and the systemic administration of CPI or other immunostimulatory agent). The BO-11X formulation by intratumoral or peritumoral injection may be performed at the level of skin, i.e. into the skin (e.g. for treating melanoma or in connection to the combination with a vaccine) or of an internal organ or tissue, i.e. into said internal organ or tissue (e.g. by intrahepatic injection for treating liver cancer or intravesicular administration for bladder cancer). Such local administration of BO-11X formulation preferably follows or (preferably) is followed by the administration of the immunostimulatory agent.

Additional Effects and Uses

In a further embodiment, the present invention provides pharmaceutical uses and methods involving the administration of a BO-11X formulation for increasing immune response against a pathogen or undesirable biological agent and in particular for enhancing an anti-tumor immune response, potentially acting itself as an immune-modulating agent. Such an effect can be monitored by measuring tumor-related immune response into the tumor site and tumor microenvironment (or in the bloodstream, other biological fluids, and tissues) at the level of relevant cell types or subpopulations (e.g. dendritic cells, T regulatory cells, T cells and/or NK cells) and/or of immunological biomarkers (e.g. chemokines, growth factors, cytokines, and their receptors).

Pharmaceutical Compositions

Also provided are methods for making a pharmaceutical composition of BO-111 or BO-112 (and/or other BO-11X formulations) by mixing a BO-11X formulation and one or more pharmaceutically acceptable adjuvant, diluent, carrier, or excipient thereof. Such components can be adapted for the specific medical indication (e.g. a solid cancer or a hematological cancer) and/or the administration means e.g. by injection (peritumoral, intratumoral, intrahepatic, intrapancreatic, or subcutaneous injection), by inhalation, or orally.

BO-11X formulation-based combination treatments may involve the same or different administration routes for BO-11X formulation and the other compound. In particular, the BO-11X formulation can be administered, as for other immunostimulatory RNA agents, by intratumoral or peritumoral injections that may activate the immune system prior to the systemic administration of a therapeutic antibody acting as CPI such a PD-1/PD-L1 pathway inhibitors (Bald T et al., 2014) or activated T cells (Amos S M et al., 2011). Alternatively, the BO-11X formulation together with other therapeutic compounds being TLR agonist or ligands such as CpG molecules or Resiquimod for enhancing the effect of anticancer vaccination (Sajadian A et al., 2014) or Dendritic cells (Fujimura T et al., 2006).

Immune-Modulating Agents

The BO-11X formulation may be combined with one or more immune-modulating agents. In some embodiments, the immune-modulating agent is a co-stimulatory or co-inhibitory molecule (e.g. of one or more immune cells, such as, by way of non-limitation, T cells and NK cells). In some embodiments, the immune-modulating agent is an agent that modulates a CD4 and/or CD8 T cell, for instance by acting as agonist or antagonist with respect to CD3, CD4, CD8, PD-1, PD-L1, PD-L2, CTLA-4, CD137, CD96, CD73, CD90, CD47, CD69, CD26, TIM3, and LAG3. In other embodiments, the immune-modulating agent is an agent that modulates NK cells, for instance by acting as agonist or antagonist with respect to CD3, NKp46, CD16, NKG2D, NKp44, and NKp30. In other embodiments, the immune-modulating agent is an agent that modulates tumor stroma and endothelium biomarkers, for instance by acting as agonist or antagonist with respect to CD45, PD-L1, PD-L2, PTEN, and CD31.

The immune-modulating agent is provided as a further compound in form of a chemical organic or inorganic compound, a nucleic acid, an aptamer, a peptide, a protein, and more particularly an antibody that binds the relevant target in the biological fluids or on cell surface. The antibody may be polyclonal or monoclonal; intact or truncated (e.g., F(ab')$_2$, Fab, Fv); bispecific or multispecific; xenogeneic, allogeneic, syngeneic, or modified forms thereof (e.g., a chimeric antibody or a humanized antibody). When the immune-modulating agent is a monoclonal antibody, it may be a non-human mammal-derived monoclonal antibody, a recombinant chimeric monoclonal antibody, a recombinant humanized monoclonal antibody, or a human monoclonal antibody.

The antibody that acts as immune-modulating agent can further comprise the structural elements normally required for exerting the required biological activity, such as four polypeptide chains, two heavy (H) chains and two light (L) chains inter-connected by disulfide bonds that are capable of binding one or more antigens (e.g. bi-specific or multi-specific antibodies) and presenting an Fc region of an immunoglobulin (e.g. IgA, IgG, IgE, IgD or IgM) which may interact with Fc receptors and activate an immune response leading to depletion and/or cell death of immune cells or other cells. Each heavy chain is comprised of a heavy chain variable region (VA) and a heavy chain constant region. The heavy chain constant region is comprised of three domains, $CH_1$, $CH_2$ and $CH_3$. Each light chain is comprised of a light chain variable region ($V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each variable region ($V_H$ or $V_L$) contains 3 CDRs, designated CDR1, CDR2 and CDR3. Each variable region also contains 4 framework sub-regions, designated FR1, FR2, FR3 and FR4. The term antibody includes all types of antibodies, including, for example, IgA, IgG, IgD, IgE and IgM, and their respective subclasses (isotypes), e.g., IgG-1, IgG-2, IgG-3, and IgG-4; IgA-1 and IgA-2. An antibody, in some embodiments, also refers to antibody fragments and antigen-binding fragments.

Antibodies suitable for practicing the methods described herein can be of various antibody formats, for example, monoclonal, polyclonal, bispecific, multispecific, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain at least two antigens or target binding sites against at least two targets described herein. The immunoglobulin molecules described herein can be of any type (e.g. IgG, IgE, IgM, IgD, IgA and IgY), class (e.g. IgGI, IgG2, IgG3, IgG4, IgA1 and IgA2) or subclass of immunoglobulin molecule. In addition, antibodies (e.g. mono-, bi-, and/or multi-specific) suitable for practicing the invention described herein can be provided in any of the alternative formats that are disclosed in the literature, for example Diabodies; Flexibodies; Camelid Antibodies, Immunobodies; Triomabs, Pepbodies, Vaccibodies, minibodies, Fcabs, UniBodies, or DuoBodies (Storz U 2011).

PD-1 (also known as CD279 or Programmed cell death protein 1) is a member of the B7 family of receptors. In some embodiments, PD-1 refers to the human PD-1 sequence (see, e.g. NCBI Reference Sequence: NP_005009) and any naturally occurring allelic, splice variants, and processed forms thereof (Keir M et al., 2008; UniProt: Q15116). PD-1 binds PD-L1 (also known as CD274 or B7-H1) and PD-L2 (also known as CD273 or B7-DC), which are also members of the B7 family. In some embodiments, PD-L1 refers to human PD-L1 (see, e.g. GenBank: AF233516), PD-L2 refers to human PD-L2 (e.g. NCBI Reference Sequence: NM_025239), together with and any naturally occurring allelic, splice variants, and processed forms thereof.

In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO), pembrolizumab (KEYTRUDA), pidilizumab (CT-011), MK-3475, BMS 936559, MPDL328OA.

In some embodiments, the BO-11X formulation is combined with one or more of BMS-936559 and MEDI4736 for treatment of, for example, advanced solid tumors. In some embodiments, the BO-11X formulation is combined with one or more MPDL3280A (optionally with vemurafenib) and MEDI4736 (optionally with one or more of dabrafenib and trametinib) for the treatment of melanoma. In some embodiments, the BO-11X formulation is combined with one or more MPDL3280A (optionally with erlotinib) and MEDI4736 (optionally with tremelimumab) for the treatment of NSCLC. In some embodiments, the BO-11X formulation is combined with MPDL3280A (optionally with one or more of bevacizumab and sunitinib) for the treatment of RCC. In some embodiments, the BO-11X formulation is combined with MPDL3280A for the treatment of solid or hematological malignancies. In some embodiments, the BO-11X formulation is combined with one or more MPDL3280A (optionally with one or more of bevacizumab, chemotherapy and cobimetinib); MEDI4736 (optionally with tremelimumab) and MSB0010718C for the treatment of solid tumors. In some embodiments, the BO-11X formulation is combined with AMP-224 for the treatment of advanced cancer. In some embodiments, the BO-11X formulation is combined with nivolumab (optionally with iliolumbar (anti-KIR)) for the treatment of advanced solid tumors. In some embodiments, the BO-11X formulation is combined with nivolumab for the treatment of castration-resistant prostate cancer, melanoma, NSCLC, and RCC. In some embodiments, the BO-11X formulation is combined with pembrolizumab for the treatment of colon cancer. In some embodiments, the BO-11X formulation is combined with pembrolizumab for the treatment of gastric cancer, head and neck cancer, TNBC, and urothelial cancer. In some embodiments, the BO-11X formulation is combined with nivolumab (optionally with ipilimumab) for the treatment of gastric cancer, pancreatic cancer, small-cell lung cancer, and TNBC. In some embodiments, the BO-11X formulation is combined with nivolumab (optionally with ipilimumab) for the treatment of glioblastoma. In some embodiments, the BO-11X formulation is combined with nivolumab for the treatment of hepatocellular cancer. In some embodiments, the BO-11X formulation is combined with pembrolizumab for the treatment of Hodgkin lymphoma, myeloma, myelodysplastic syndrome, and non-Hodgkin lymphoma. In some embodiments, the BO-11X formulation is combined with pidilizumab for the treatment of malignant gliomas. In some embodiments, the BO-11X formulation is combined with one or more of nivolumab (optionally with one or more of ipilimumab, and multiple class 1 peptides and montanide ISA 51 VG; and optionally sequentially with ipilimumab) and pembrolizumab for the treatment of melanoma. In some embodiments, the BO-11X formulation is combined with pembrolizumab for the treatment of melanoma and NSCLC. In some embodiments, the BO-11X formulation is combined with one or more of nivolumab (optionally with one or more of gemcitabine/cisplatin, pemetrexed/cisplatin, carboplatin/paclitaxel, bevacizumab, erlotinib, and ipilimumab) and pembrolizumab for the treatment of NSCLC. In some embodiments, the BO-11X formulation is combined with pidilizumab (optionally with gemcitabine) for the treatment of pancreatic cancer. In some embodiments, the BO-11X formulation is combined with pidilizumab (optionally with one or more of sipuleucel-T and cyclophosphamide) for the treatment of prostate cancer. In some embodiments, the BO-11X formulation is combined with one or more of nivolumab (optionally with one or more of sunitinib, pazopanib, and ipilimumab), pembrolizumab (optionally with pazopanib), and pidilizumab (optionally with dendritic cell/RCC fusion cell vaccine) for the treatment of RCC. In some embodiments, the BO-11X formulation is combined with one or more of anti-LAG3 (BMS-986016, optionally with nivolumab), nivolumab (optionally with interleukin-21), and AMP-554 for the treatment of solid tumors. In some embodiments, the BO-11X formulation is combined with pembrolizumab for the treatment of solid tumors.

In various embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the BO-11X formulation is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an antibody such as, by way of non-limitation, ipilimumab (MDX-010, MDX-101, Yervoy, BMS) and/or tremelimumab (Pfizer). In some embodiments, the BO-11X formulation is combined with ipilimumab (optionally with bavituximab) for the treatment of one or more of melanoma, prostate cancer, and lung cancer.

In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab, obinutuzumab (GAZYVA), AME-133v, Ocrelizumab, TRU-015, and veltuzumab.

Validation of BO-11X Formulations

The pre-clinical validation of therapeutic efficacy of a BO-11X formulation (in accordance to the present invention and as exemplified by BO-111 and BO-112 in the Examples) can be performed in cell-based assays and, most interestingly, in animal models where different experimental criteria can be tested and compared to establish the most appropriate conditions to achieve therapeutic effects effectively, using the BO-11X formulation alone or in combination with a candidate or approved anti-cancer drug, These criteria include the doses, administration route, the order and/or the frequency of administration of either compound at the scope to identify which are the better conditions for therapeutic use of a BO-11X formulation (alone or synergically with a candidate or approved anti-cancer drug) in terms of efficacy, safety, and/or clinical use.

The effects of different dosage of a BO-11X formulation, number and/or site of administration (in particular, by injecting it in one or more sites), route of administration, frequency, and/or time point for administration can be associated to relevant end-points and physiological parameters that are measured in biological samples obtained from cells or (preferably) animals that are exposed to the tested compounds, alone or in combination with other drugs. A non-limiting list of such parameters includes regression of tumor size, block of tumor growth and/or proliferation of tumor cells, apoptosis, reduced tumor vascularization or metastasis, overcoming resistance to a common anti-cancer drug (or otherwise improving the response to such a drug in the treated population), reduced treatment related-adverse events on normal tissues and functions, modulation of immune response and/or of immune cells having specific activities and features, identification of biomarkers or specific cell populations in biological materials (e.g. present in cancer cell preparations, tumor biopsies or biological fluids) whose increase (or decrease) is known in the literature as being associated to anti-cancer effect in general, and in particular to survival of animal models and possibly of cancer patients. Whenever possible, such end-points are measured at intermediate and final time-points following the administration of each test compound, or a test combination of compounds at a given dose and/or regimen, by using a specific route of administration and/or pharmaceutical formulations.

The therapeutic, anti-cancer efficacy of a BO-11X formulation can be tested alone or in combination with standard-of-care, conventional treatments (such as radiotherapy, chemotherapy, inhibitors of cellular kinases, etc.) or treatments involving novel mechanisms and/or novel candidate anti-cancer drugs. Indeed, a category of novel anti-cancer compounds that can be tested in combination with a BO-11X formulation are those improving the anti-tumor immune responses within tumor microenvironment, by providing a systemic antitumor immunity that targets disseminated tumor cells are eliminated. This approach has been proven successful in animal models and patients and can improve the outcome of conventional therapies such as radiotherapy or chemotherapy (see, for example, Galluzzi L et al., 2014; Vacchelli E et al., 2013; Van der Jeught K et al., 2015).

This growing panel of new cancer drugs targets the mechanisms by which cancer cells escape from immune detection and destruction by human body. Cancer-specific immunotherapies may provide a series of advantages when compared to other cancer therapies (e.g. tumor cell specificity). Indeed, the identification of a series of molecular targets for cancer immunotherapies is allowing major advances in defining the mechanisms and compounds that can provide the appropriate co-stimulatory (or co-inhibitory) effect on immune responses against tumors with respect to their plasticity, heterogeneity, resistance, or microenvironment.

A non-limiting list of cancer passive or active immunotherapies, each acting on different molecular targets and/or mechanisms, includes tumor-targeting or other immunomodulatory monoclonal antibodies, oncolytic viruses, immunostimulatory cytokines, adoptive cell transfer and other cell-based therapies, DNA-or peptide-based vaccines, inhibitors of immunosuppressive metabolism, or agonists of pattern recognition receptors. Among these mechanisms, molecular targets against which antibodies or other compounds having either agonistic or antagonistic activity (depending on their role in immune response or cancer escape from immune response) include a series of cell membrane proteins such as PD-1, PD-L1, PD-L2, CTLA-4, CD137, CD38, OX-40, CD26, TIM3, and LAG3 that are checkpoints for tumor development and against which different agonistic or antagonistic antibodies are available commercially or in scientific repositories for characterizing their specificity and/or level of anti-cancer effect against the human antigen or (when dealing with animal models) the corresponding rodent antigen.

Despite impressive patient responses to agents targeting these co-stimulatory or co-inhibitory molecules (e.g. therapies that are based on an anti-PD-1 or anti-PD-L1 antibody) the clinical response to immune checkpoint inhibitors is still incompletely or inefficiently achieving the desired therapeutic effect in too many cancer patients. A BO-11X formulation in an appropriate combination with a compound such as an anti-PD-1 or anti-CD137 antibody may enhance the reduction of tumor growth and metastasis (or increase the number of subjects presenting such reduction), when compared to the effect of the administration of one of those two anti-cancer agents alone, possibly beyond the additive effects that may be expected.

The therapeutic effects of a BO-11X formulation can be evaluated in one of the several cell-based models that are based on isolated or mixed cell culture including primary cancer cells or established cancer cell lines, preferably from a human origin. Examples of cancer cell lines for validating BO-11X formulations can be defined according to cancer type such as melanoma (human SK-Mel-19, SK-Mel-103 and UACC62 cells; murine B16 cells), carcinoma (mouse Hepa 1-6 cells; rat FAO cells), breast cancer (human BT483, HCC1143, HCC1937, MDA-MB-231, MDA-MB-415, MDA-MB-468, and BT549 cells), pancreatic cancer (human MiaPaCa2, IMIM-PC2, Panc1, Panc0203, Panc 3.27, or BxPc3 cells), or other relevant cell lines that are available through ATCC, other official or academic repositories, or commercial providers. The anticancer effects of BO-11X formulations can be evaluated at the level of period of time, frequency, and/or dose that is required to have a block of proliferation, the death, the expression of biomarkers, and/or the release of signaling molecules (such as chemokines or Interferon Beta) that indicate a potentially relevant effect of the BO-11X formulation to be confirmed in more physiological conditions.

Then, the effects of a BO-11X formulation can be evaluated in tumor animal models in which the anti-tumor response due to the administration of an exemplary formulation such as BO-112 is assessed in different protocols for both monotherapy and combination treatment (e.g. together with a CPI such as an anti-PD-1 antibody) throughout a shorter or longer period of time after administration. The study may be pursued by administering BO-112 and/or anti-PD-1 antibody in animals at a given time of tumor development due to proliferation of injected cells, that is after a specific number of days following the injection of cancer cells or (preferably) that present the desired tumor size (e.g. an average size of 80-100 mm3), or even following its disappearance (for evaluate any effect of each drug or drug combination on tumor relapse). The study would also involve control compounds that are either negative (e.g. vehicle alone) or positive controls, such as chemotherapeutic or other anti-cancer drugs that are indicated in the literature as standard for drug effectiveness for a specific tumor and/or in a given animal model. These activities of validation in animal models and animal cell may also lead to the development of BO-11X formuation for veterinary use.

The animal model is typically a mouse model in which the cancer is consequent to either the transfer and engraftment of human cancer cells (coming from an immortalized cell line or a cancer biopsy that is obtained by a patient) or the induction (or transfer) of mouse tumor cells in the animals. Cells can be originated by different type of tumors (e.g. lung carcinoma, melanoma, lymphoma) and can be injected subcutaneously in the flank of the mice to simply the detection of tumor and the analysis of its size and/or composition during the study. Mice are then treated by randomizing them into groups each of a size allowing statistical analysis of results (e.g. 3, 5, 10, 12, 15, 20 or more animals for each control or treatment group).

Features that a BO-11X formulation such as BO-112 and a checkpoint inhibitor such as an anti-PD-1 antibody may improve in cancer animal models (in particular when appropriately combined in terms of amount, order, or other administration criteria), may include animal survival after treatment and/or tumor disappearance, reduced tumor relapse, limited or delayed toxicity and/or resistance effects, and response to re-challenge of tumor inoculation after termination of the treatment with BO-112 and/or anti-PD-1 antibody.

The exemplary BO-11X formulation that is identified structurally and functionally above as BO-112 and anti-PD-1 antibody can be administered (alone or in combination, in single or multiple doses) at different locations with respect to tumor cells and/or in different amount. Typically, BO-112 and the monoclonal antibody specific for mouse PD-1 (e.g. clone RMP1-14 from BioLegend or similar ones available by other providers) are injected sub-cutaneously, intravesicularly, intraperitoneally, peritumorally or intratumorally (depending on the model and tumor molecular and pathological features) at a concentration that is determined with respect to animal weight (e.g. between 0.01 and 2.5 mg/kg), concentration in the injected volume (e.g. between 0.01 and 0.5 mL, and/or content in each dose (e.g. between 0.01 and 250 μg per dose). In particular, the dose-response of BO-112 in different concentrations, combined with a fixed anti-PD-1 antibody dose (or vice versa), may allow determining any advantageous effect that is consequent to the significant reduction in the amount of either compound that is administered due to the combination with the other compound (e.g. unaffected or even improved efficacy and/or safety profile; abscopal effects in tumors that are in different, untreated locations).

BO-112 can be injected in one or multiple cycles (e.g. 2, 3, 4, or more) that are separated by given number of days (1, 2, 3, 5, 7, or more). Alternatively, when BO-112 is co-administered with the anti-PD1 antibody, BO-112 can be injected immediately before (or after) the antibody (or in a single injectable preparation), again in one or multiple cycles (that are separated by given number of days. Still alternatively, the two agents may be formulated, or administered in any sequential order, but separated by variable period of time (e.g. 1 hour, 3 hours, 6 hours, 12 hours, 18 hours, 24 hours, 36 hours, 2 days or more). In particular, when BO-112 is administered after anti-PD-1 antibody, its later administration (alone or further in combination with the anti-PD-1 antibody) may provide an anti-tumor rescue effect in animals in which anti-PD-1 antibody was ineffective against tumor cells, overcoming any specific tumor resistance or escape mechanism. At the end of treatment, all surviving animals can be left untreated for 1, 2, 3, or more consecutive weeks to monitor if and how tumor cells reappear, with or without re-challenging all animals that had a complete regression of tumor with a further subcutaneous injection of cancer cells.

The effects of BO-112, alone or in combination with the anti-PD1 antibody as listed above, can be assessed as interim results that are reported during the study without sacrificing the animals (e.g. by measuring tumor size, percentage of mice still alive, bodyweight, or behavioural criteria) or after sacrificing the animal (or in already dead mice) for determining molecular features of tumor and/or normal cells (including total number and/or specific sub-populations of NK cells, tumor-infiltrated lymphocytes, splenocytes, incorporation of radiolabeled precursors, and other cells that may be involved in the anti-tumor local or systemic immune responses, such as. Myeloid-derived suppressor cells (MDSCs), regulatory T cells (Tregs); tumor associated neutrophils (TANs), M2 macrophages, and tumor associated macrophages (TAMs). I parallel, the presence/absence of relevant biomarkers can be determined by PCR amplification of relevant RNAs, or at protein level on the surface of cells within tissues or circulating in blood, such as cytokines or chemokines by using standard immunological assays and kits.

This global phenotype analysis can be performed by using cells isolated from tumors, blood, spleen, lymph nodes, or other relevant tissues and locations, for detecting any statistically and/or therapeutically relevant change in the number of cells expressing cell surface markers that are detected by flow cytometry and described in the literature such as CD3, CD4, CD25, FoxP3, CD8, PD-1, PD-L1, PD-L2, PTEN, CTLA-4, CD137, CD96, CD73, CD90, CD47, CD69, CD26, TIM3, LAG3, Gr1, CD11b, Ly6C, Ly6G, NKp46, CD16, NKG2D, NKp44, NKp30, CD45, and CD31. Such cells can be also evaluated at the level of tumor antigen-specific immune response, expression of relevant transcription factors, cytokines or chemokines (e.g. IFN-gamma, IFN-beta, TNFalpha, HIF1a, HIF2a, p53), or by using other cell-based assays.

Additionally, macroscopic examination of organs and skin and microscopic, pathological analysis in either immune-deficient fully immune competent animal models can further provide indication about the efficacy of the study compounds (alone or in the combination) or of their toxicity, such as organ inflammation and necropsy. The quantitative data that are generated in similar studies can be compared among the different experimental groups by using the appropriate statistical tests, with and without corrections for multiple testing, at the scope to evaluate which therapeutic (in particular anti-tumor) effects are provided by the administration of a BO-11X formulation, alone or in combination with another anti-cancer agent.

Methods of Treatment and Patient Selections

In some embodiments, the present invention relates to a method for treating, reducing, ameliorating, or preventing cancer growth, survival, metastasis, epithelial-mesenchymal transition, immunologic escape or recurrence, comprising administering by administering a BO-11X formulation and one or more immune-modulating agents. The cancer may be an oncological disease. The cancer may be a dormant tumor, which may result from the metastasis of a cancer. The dormant tumor may also be left over from surgical removal of a tumor. The cancer recurrence may, for example, be tumor regrowth, a lung metastasis, or a liver metastasis.

In various embodiments, the cancer is one or more of basal cell carcinoma, biliary tract cancer; bladder cancer; bone cancer; brain and central nervous system cancer; breast cancer; cancer of the peritoneum; choriocarcinoma; connective tissue cancer; cancer of the digestive system (including esophageal, stomach, colon, rectal or other gastrointestinal cancer); eye cancer; cancer of the head and neck; glioblastoma; hepatic carcinoma; hepatoma; intra-epithelial neoplasm; kidney, adrenal, or renal cancer; leukemia; liver cancer; lung cancer (e.g. small-cell lung cancer, non-small cell lung cancer, lung adenocarcinoma, and lung squamous carcinoma); melanoma; myeloma; neuroblastoma; oral cavity cancer (lip, larynx, tongue, mouth, and pharynx); pancreatic cancer; prostate cancer; retinoblastoma; rhabdomyosarcoma; cancer of the respiratory system; salivary gland carcinoma; skin cancer; squamous cell cancer; testicular cancer; thyroid cancer; uterine, endometrial, cervical, vulval, ovarian or other gynecological cancer; cancer of the urinary system; lymphoma including B-cell lymphoma, Hodgkin's and non-Hodgkin's lymphoma (NHL; including specific types such as low grade/follicular, small lymphocytic, intermediate grade/follicular, intermediate grade diffuse, high grade immunoblastic, high grade lymphoblastic, high grade small non-cleaved cell, or bulky disease NHL), mantle cell and AIDS-related lymphoma; chronic lymphocytic leukemia; acute lymphoblastic leukemia; Hairy cell leukemia; chronic myeloblastic leukemia; as well as other carcinomas and sarcomas; post-transplant lymphoproliferative disorder (PTLD), as well as abnormal vascular proliferation associated with phakomatoses or edema (such as those that associated with brain tumors).

In various embodiments, the cancer is a biliary tract cancer. In some embodiments, the biliary tract cancer is selected from pancreatic cancer, gallbladder cancer, bile duct cancer, and cancer of the ampulla of Vater. In various embodiments, the cancer is liver cancer. In various embodiments, the cancer is colon cancer. In some embodiments, the biliary tract cancer is cholangiocarcinoma and/or an adenocarcinoma.

In some embodiments the BO-11X formulation and/or immune-modulating agent is used to treat cancers of various stages (e.g. Stage I, or II, or III, or IV). By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In some embodiments, the BO-11X formulation (and/or the immune-modulating agent) reduces side effects of the therapies that a patient may experiences. For example, the combination therapy of an BO-11X formulation and one or more immune-modulating agent may allow for a lower dose of the BO-11X formulation and/or one or more immune-modulating agent (e.g. as compared to monotherapy) and thereby increase the therapeutic window of either agent. In some embodiments, the lowered dose mitigates one or more side effects without (or minimal) loss of efficacy. In some embodiments, the BO-11X formulation and/or immune-modulating agent is used to treat a subject that has a treatment-refractory cancer. In some embodiments, the BO-11X formulation is used to treat a subject that is refractory to one or more immune-modulating agents, in particular the one that is actually combined with the BO-11X formulation.

For instance, in some embodiments, the subject is refractory to a PD-1 and/or PD-L1 and/or PD-L2 agent, including, for example, nivolumab (ONO-4538/BMS-936558, MDX1106, OPDIVO), pembrolizumab (KEYTRUDA), pidilizumab (CT-011), MK-3475, BMS-936559, Ibrutinib, and/or MPDL328OA-refractory patients. For instance, in some embodiments, the subject is refractory to an anti-CTLA-4 agent, e.g. ipilimumab (Yervoy)-refractory patients (e.g. melanoma patients). In some embodiments, the subject is refractory to a BO-11X formulation. Accordingly, in various embodiments the present invention provides methods of cancer treatment that rescue patients that are non-responsive to various therapies, including monotherapy of an BO-11X formulation or one or more immune-modulating agents.

In various embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey (e.g. baboon) or chimpanzee.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient or a subject. In some embodiments, the human is a female. In some embodiments, the human is a male.

Treatment Regimens and Combination Therapies

In some embodiments, present invention provides for specific cancer treatment regimens with BO-11X formulations and immune-modulating agents (and optionally one or more additional therapeutic agent). For example, in some embodiments, the BO-11X formulation, e.g. BO-111 OR BO-112, is administered to a patient first to normalize tumor vascularization, optionally by reducing or ablating hypoxia. Such first administration of the BO-11X formulation, e.g. BO-111 OR BO-112, may stimulate and/or increase T lymphocytes (e.g. CD4+ and CD8+ T cells) and/or NK cells tumor and/or inhibit and/or decrease recruitment of immunosuppressive cells (e.g. myeloid-derived suppressor cells (MDSCs), regulatory T cells (Tregs); tumor associated neutrophils (TANs), M2 macrophages, and tumor associated macrophages (TAMs)) to the tumor. In some embodiments, the present therapies may alter the ratio of M1 versus M2 macrophages in the tumor site to favor M1 macrophages. Notably, unlike for example, anti-angiogenic molecules, the BO-11X formulations, in some embodiments, induce a long lasting (i.e. greater than transient) vascular normalization. For example, BO-11X formulation-vascular normalization may last greater than 1, or 2, or 3, or 4, or 5, or, or 6, or 7, or 14 days, or 21 days. Accordingly, in some embodiments, this long-lasting BO-11X formulation-vascular normalization allows for a sustainable permissive tumor microenvironment that is more likely to be responsive to one or more immune-modulating agents. That is, in some embodiments, the BO-11X formulation potentiates immune-modulating agent therapy.

Alternatively, the BO-11X formulation, e.g. BO-111 OR BO-112, is administered to a patient after treatment with one or more immune-modulating agents. For instance, in some embodiments, the immune-modulatory agent targets one or more co-inhibitory molecules and reduces or eliminates immunosuppression. In this favorable context, i.e. upon removal of suppression, the BO-11X formulation, e.g. BO-111 OR BO-112, is administered is administered to stimulate the immune system. Or the immune-modulatory agent targets one or more co-stimulatory molecules first and the BO-11X formulation, e.g. BO-111 OR BO-112, is administered is administered second to bolster this effect, for example, synergistically.

Further, as described herein, the BO-11X formulation and/or immune-modulating agent can be combined with an additional therapeutic agent in the context of, for example, co-administration, a treatment regimen or a co-formulation.

In some embodiments, the BO-11X formulation and/or immune-modulating agent, optionally with an additional therapeutic agent, can be administered sequentially. The term "sequentially" as used herein means that the additional therapeutic agent and the BO-11X formulation and/or immune-modulating agent are administered with a time separation of more than about 60 minutes. For example, the time between the sequential administration of the additional therapeutic agent and the BO-11X formulation and/or immune-modulating agent can be more than about 60 minutes, more than about 2 hours, more than about 5 hours, more than about 10 hours, more than about 1 day, more than about 2 days, more than about 3 days, or more than about 1 week apart. The optimal administration times may depend on the rates of metabolism, excretion, and/or the pharmacodynamic activity of the additional therapeutic agent and the BO-11X formulation and/or immune-modulating agent being administered. Either the additional therapeutic agent or the present agents may be administered first.

In some embodiments, the BO-11X formulation and/or immune-modulating agent, optionally with an additional therapeutic agent, can be administered simultaneously. The term "simultaneously" as used herein, means that the additional therapeutic agent and the BO-11X formulation and/or immune-modulating agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and BO-11X formulation and/or immune-modulating agent can be by simultaneous administration of a single formulation (e.g. a formulation comprising the additional therapeutic agent and the BO-11X formulation and/or immune-modulating agent) or of separate formulations (e.g., a first formulation including the additional therapeutic agent and a second formulation including the BO-11X formulation and/or immune-modulating agent).

Co-administration also does not require the additional therapeutic agents to be administered to the subject by the same route of administration. Rather, each therapeutic agent can be administered by any appropriate route, for example, parenterally or non-parenterally.

Such a combination may lead to synergism and/or additive and/or potent effects at a lower dose of the BO-11X formulation and/or immune-modulating agent. For example, when the BO-11X formulation is combined with one or more immune-modulating agents the effective amount of the BO-11X formulation may be lower than what it would be in a monotherapy. In some embodiments, the BO-11X formulation is combined with an immune-modulating agent and the effective amount of the BO-11X formulation is a sub-therapeutic dose, for example, when the immune-modulating agent is combined with a BO-11X formulation the effective amount of the immune-modulating agent may be lower than what it would be in a monotherapy. In some embodiments, the immune-modulating agent is combined with a BO-11X formulation and the effective amount of the immune-modulating agent is a sub-therapeutic dose. In various embodiments, the immune-modulating agent is combined with a BO-11X formulation and an additional therapeutic agent and the effective amount of the additional therapeutic agent is a sub-therapeutic dose. The term "sub-therapeutic dose or amount" means that a dose or amount of a pharmacologically active substance is below the dose or amount of that substance that is administered, as the sole substance, to achieve a therapeutic effect. The sub-therapeutic dose of such a substance may vary depending upon the subject and disease condition being treated, the weight and age of the subject, the severity of the disease condition, the manner of administration and the like, which can readily be determined by one of ordinary skill in the art. In one embodiment, the sub-therapeutic dose or amount of the chemotherapeutic agent is less than 90% of the approved full dose of the chemotherapeutic agent, such as that provided in the U.S. Food & Drug Administration-approved label information for the chemotherapeutic agent. In other embodiments, the sub-therapeutic dose or amount of the chemotherapeutic agent is less than 80%, 70%, 60%, 50%, 40%, 30%, 20% or even 10% of the approved full dose, such as from 20% to 90%, 30% to 80%, 40% to 70% or another range within the values provided herein.

In some embodiments, the effective amount of the immune-modulating agent is less than an effective amount used in monotherapy for the same cancer and/or a combination therapy with an agent besides a BO-11X formulation for the same cancer. In some embodiments, the effective amount of the BO-11X formulation is less than an effective amount used in monotherapy for the same cancer or clinical status, and/or a combination therapy with an agent (such as an immune-modulating agent) for the same cancer or clinical status.

In various embodiments, the BO-11X formulation is combined with one or more immune-modulating agents (e.g. 1, or 2, or 3, or 4, or 5 immune-modulating agents) and, optionally, one or more additional therapeutic agents (e.g. 1, or 2, or 3, or 4, or 5 additional therapeutic agents). Such combinations may lead to synergism and/or additive and/or potent effects at a lower dose of the BO-11X formulation and/or immune-modulating agent and/or the one or more additional therapeutic agents. Co-administration may be simultaneous or sequential. Further the pharmaceutical compositions including the BO-11X formulation and/or immune-modulating agent may comprise the additional therapeutic agent (e.g. via co-formulation). That is, in some embodiments, two or more of any of the agents disclosed herein may be co-formulated. Further, in some embodiments, the BO-11X formulation and/or immune-modulating agent may be administered to a patient that is undergoing treatment with one or more additional therapeutic agent. Further, in some embodiments, the BO-11X formulation and/or immune-modulating agent may supplant a patient's current treatment with one or more additional therapeutic agent.

Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the agents described herein are used as an adjuvant therapy in the treatment of a cancer. In some embodiments the therapeutic agents described herein are administered as a neo-adjuvant therapy prior to resection. In certain embodiments, neo-adjuvant therapy refers to therapy to shrink and/or downgrade the tumor prior to any surgery. In some embodiments, neo-adjuvant therapy means a therapeutic agent described herein is administered to cancer patients prior to surgery or other technique allowing tumor ablation.

In some embodiments the therapeutic agents described herein are useful as a maintenance therapy after an initial treatment with a first-line therapy, including without limitation any of the additional therapeutic agents of the present disclosure.

In various embodiments, the present invention provides a treatment regimen or a method for treating cancer or tumors in a subject that includes administering simultaneously or sequentially a therapeutically effective amount of a BO-11X formulation and/or an immune-modulating agent and one or more of the additional therapeutic agents described herein. In various embodiments, the present invention provides a treatment regimen or a method for treating cancer or tumors in a subject that includes administering simultaneously or sequentially a therapeutically effective amount of a BO-11X formulation and/or an immune-modulating agent and one or more of the anti-cancer agents described herein, including but not limited to chemotherapeutic agents. Suitable chemotherapeutic agents to be used in the methods of the present invention may include those described herein. In certain embodiments, the chemotherapeutic agent is one or more of 5-fluorouracil (5-FU), doxorubicin, gemcitabine, paclitaxel, and cisplatin. By way of example, in some embodiments, the present invention provides combining a BO-11X formulation and/or an immune-modulating agent with one or more common cancer treatment regimens (by way of non-limiting illustration, FOLFOX, FOLFIRI, IFL, FL (Mayo), QUASAR, Machover schedule, CAF, CMF, ECF, and FEC).

In various embodiments, the additional therapeutic agent is an antihyperproliferative agent. Antihyperproliferative agents include, but are not limited to, doxorubicin, daunorubicin, mitomycin, actinomycin D, bleomycin, cisplatin, VP16, enedyine, taxol, vincristine, vinblastine, carmustine, melphalan, cyclophsophamide, chlorambucil, busulfan, lomustine, 5-fluorouracil, gemcitabin, BCNU, or camptothecin.

In addition, the additional therapeutic agent can further include the use of radiation. In addition, the methods of treatment can further include the use of photodynamic therapy.

Salts, Pharmaceutical Compositions and Doses

In some embodiments, the present invention provides for the agents described herein and pharmaceutically acceptable esters, pro-drugs, salts, solvates, enantiomers, stereoisomers, active metabolites, co-crystals, and other physiologically functional derivatives thereof.

In one aspect, the present invention provides agents described herein, and a pharmaceutically acceptable carrier or excipient. The pharmaceutical composition can be in any suitable form appropriate for the desired use and route of administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol mono-stearate, talc, sodium chloride, dried skim milk, glycerol, propylene, glycol, water, ethanol and the like. Other examples of suitable pharmaceutical excipients are described in Remington's Pharmaceutical Sciences (edited by Allen, Loyd V., Jr; $22^{nd}$ edition, 2012).

Additionally, the pharmaceutical compositions of the present invention may contain adjuvants such as preservatives, wetting agents, emulsifying agents, pH buffering agents, and dispersing agents. Further, auxiliary, stabilizing, thickening, lubricating, and coloring agents can be included. Prevention of the action of microorganisms may be ensured by the inclusion of various antibacterial and antifungal agents, for example, paraben, chlorobutanol, phenol sorbic acid, and the like. The pharmaceutical compositions may also include isotonic agents such as sugars, sodium chloride, and the like.

Where necessary, the pharmaceutical compositions can also include a solubilizing agent. Also, the agents can be delivered with a suitable vehicle or delivery device as known in the art. Compositions for administration can optionally include a local anesthetic such as, for example, lidocaine to lessen pain at the site of the injection.

The pharmaceutical compositions of the present invention can take the form of solutions, suspensions, emulsions, drops, tablets, pills, pellets, capsules, capsules containing liquids, powders, sustained-release formulations, suppositories, emulsions, aerosols, sprays, suspensions, or any other form suitable for use. Thus, the composition described herein may be comprised in a capsule, tablet, pill, caplet, bottle, ampoule, sachet, syringe, cartridge, nebulizer or other container. In one embodiment, the pharmaceutical composition is in the form of a capsule. In another embodiment, the pharmaceutical composition is in the form of a tablet.

In some embodiments, the administration of any of the described agents and compositions is any one of oral, intravenous, and parenteral. In various embodiments, routes of administration include, for example: oral, intradermal, intramuscular, intraperitoneal, intravenous, subcutaneous, intranasal, epidural, sublingual, intranasal, intracerebral, intrahepatic, intrapancreatic, intravesicular, intravaginal, transdermal, rectally, by inhalation, or topically, for example, to the ears, nose, eyes, or skin. In some embodiments, the administering is effected orally or by parenteral injection. The mode of administration can be left to the discretion of the practitioner, and depends in part upon the site of the medical condition and/or concurrent treatments (being, for instance, chemotherapy, radiotherapy, or in combination with antibodies, vaccines and other cancer-targeting drugs). In various embodiments, administration results in the release of any agent described herein into the bloodstream.

Any agent and/or pharmaceutical composition described herein can be administered orally. Such agents and/or pharmaceutical compositions can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local. Various delivery systems are known, e.g., encapsulation in liposomes, microparticles, microcapsules, capsules, etc., and can be used. In specific embodiments, it may be desirable to administer locally to the area in need of treatment.

In one embodiment, an agent described herein and/or pharmaceutical composition described herein is formulated in accordance with routine procedures as a composition adapted for oral administration to humans. Solid dosage forms for oral administration include, for example, capsules, tablets, pills, powders, and granules. In such dosage forms, the active agent is mixed with at least one inert, pharmaceutically acceptable excipient or carrier such as sodium citrate, di-calcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinyl-pyrrolidone, etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium agents, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glycerylbehenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

Liquid dosage forms for oral administration include pharmaceutically acceptable emulsions, solutions, suspensions, syrups and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Dosage forms suitable for parenteral administration (e.g. intravenous, intramuscular, intrahepatic, intrapancreatic, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Pharmaceutical compositions of this invention for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions, and by the use of surfactants.

Any agent described herein and/or pharmaceutical composition described herein can be administered by controlled-release or sustained-release means or by delivery devices that are known to those of ordinary skill in the art. Such dosage forms can be useful for providing controlled- or sustained-release of one or more active ingredients using, for example, hydropropyl cellulose, hydropropylmethyl cellulose, polyvinylpyrrolidone, Eudragit, other polymer matrices, gels, permeable membranes, osmotic systems, multi-layer coatings, microparticles, liposomes, microspheres, or a combination thereof to provide the desired release profile in varying proportions. Suitable controlled- or sustained-release formulations can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Formulations comprising the agents described herein and/or pharmaceutical compositions of the present invention may conveniently be presented in unit dosage forms and may be prepared by any of the methods known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g. wet or dry granulation, powder blends, etc., followed by tableting using conventional methods known in the art).

It will be appreciated that the actual dose of the agents described herein and/or pharmaceutical compositions of the present invention to be administered according to the present invention may vary according to the particular agent, the particular dosage form, and the mode of administration. Many factors that may modify the action of the BO-11X formulations (e.g. body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the agents described herein and/or pharmaceutical compositions of the present invention can be administered in unit dosage forms (e.g., tablets or capsules) containing, for example, from about 0.01 mg to about 1,000 mg of poly(I:C) molecules within the BO-11X formulation [e.g, wherein said individual BO-11X formulation is formed by making a complex from about 0.01 mg to about 1000 mg of poly(I:C)], inclusive of all values and ranges there between. In some embodiments, the agents described herein and/or pharmaceutical compositions of the present invention are administered at an amount of from about 0.01 mg to about 1000 mg of poly(I:C) molecules within the BO-11X formulation daily, or from about 0.1 mg to about 10 mg daily [e.g, wherein said individual daily BO-11X formulation is formed by making a complex from about 0.01 mg to about 1000 mg, preferably about 0.01 mg to 10 mg of poly(I:C)], inclusive of all values and ranges there between.

In some embodiments, a suitable dosage of the agents and/or pharmaceutical compositions of the present invention is in a range of about 0.001 to about 10 mg of poly(I:C) molecules within the BO-11X formulation/kg of body weight of the subject, preferably 0.003 to about 10 mg of poly(I:C) molecules within the BO-11X formulation/kg of body weight of the subject, more preferably 0.005 to about 10 mg of poly(I:C) molecules within the BO-11X formulation/kg of body weight of the subject and even more preferably 0.01 to about 10 mg of poly(I:C) molecules within the BO-11X formulation per kg of body weight of the subject [e.g, wherein said individual BO-11X formulation administered is formed by making a complex from about 0.005 mg to about 10 mg of poly(I:C)] per kg of body weight of the subject, preferably about 0.003 mg to about 10 mg of poly(I:C)] per kg of body weight of the subject, more preferably about 0.001 mg to about 10 mg of poly(I:C)] per kg of body weight of the subject, inclusive of all values and ranges there between. In other embodiments, a suitable dosage of the BO-11X formulation and/or immune-modulating agent and/or additional therapeutic agent is in a range of about 0.01 mg/kg to about 10 mg/kg of body weight, or in a range of about 0.05 mg/kg to about 1 mg/kg of body weight.

In accordance with certain embodiments of the invention, the agents and/or pharmaceutical compositions described herein may be administered, for example, more than once daily, about once per day, about every other day, about every third day, about once a week, about once every two weeks, about once every month, about once every two months, about once every three months, about once every six months, or about once every year.

Kits

The invention also provides kits that can simplify the administration of the agents and/or pharmaceutical compositions described herein. The kit is an assemblage of materials or components, including at least one of the agents described herein. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat, for example, cancer, diabetes, or obesity. Optionally, the kit also contains other useful components, such as, diluents, buffers, pharmaceutically acceptable carriers, syringes, catheters, applicators, filters, (micro) needles, pipetting or measuring tools, bandaging materials or other useful paraphernalia as may be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

EXAMPLES

Example 1: Effects of Complex-Size on Anticancer Effects of Distinct jetPEI-Based Poly(I:C) Preparations (BO-111 Formulations)

Materials &Methods
BO-111 Formulations (2-Vial Process)

The single-stranded polyinosinic acid [poly(I)] and polycytidylic acid [poly(C)] molecules that were used for generating double-stranded polyinosinic-polycytidylic acid [poly(I:C)] molecules were obtained from commercial providers such as Tide Group, Carbogen or Invivogen. Depending from the provider and the batch, the size distribution for poly(C) molecules is defined as being: <400 bases, 20-82% (with further tests performed using preparations presenting, for instance, 33%, 43%, or 50%); 400-850 bases, 15~40% (with further tests performed using preparations presenting, for instance, 27%, 30% or 37%); 850-5000 bases, 3~50% (with further tests performed using preparations presenting, for instance, 13%, 30% or 34%); >5000 bases, 1% or less (generally absent). Depending from the provider and the batch, the size distribution for poly(I) molecules is defined as being: <400 bases, 80-95% (with further tests performed using preparations presenting, for instance, 86% and 91%); 400-850 bases, 5-20% (with further tests performed using preparations presenting, for instance, 8% or 12%); 850-5000 bases, 0~5% (with further tests performed using preparations presenting, for instance, 1% or below); >5000 bases, 1% or less (generally absent). Acceptance criteria for manufacturing BO-111 formulations that apply to poly(I) and poly(C) powder or solutions also include maximum absorption (at wavelength of 248+1 nm and of 268+1 nm for poly(I) and poly(C), respectively), endotoxin content (≤10 EU/mg), pH (6.0-8.0), and sedimentation coefficient (≥4S).

Batch poly(I) preparations were obtained by dissolving powder poly(I) (1.0 eq., 23.99 g) at 50° C. in PBS 1×(2.4 L) with continuous stirring into a 6-liter flask. Batch poly(C) preparations were obtained separately using powder poly(C) in the same manner and at the same concentration. Additional steps of filtration could be implemented to further improve quality of starting solutions using membranes with a 300 kDa cut-off or a 500 kDa cut-off (Pellicon 2 cassette, Millipore). The permeates of these filtration steps are concentrated and freed from small size impurities, such as monomers, over a 30 kDa membrane (Pellicon 2 cassette, Millipore). The resulting retentate for each solution is mixed with a concentrated buffer solution (such as PBS 10X). For both solutions, the optical density was determined to calculate the concentration as a basis for a 1:1 stoichiometry for the following annealing step, adjusting consequently the total volume before annealing step. Poly(I) solution is mixed and stirred with poly(C) solution molecules at 55-62° C. for 30 minutes. The resulting solution is slowly cooled down at room temperature for approx. 3 hours for annealing single-stranded molecules and generating poly(I:C) molecules, and finally filtered over a G3 glass pore filter (pore size of approx. 15-40 µm).

This annealing process generates a solution containing a pool of different double-stranded poly(I:C) molecules that is then applied on a chromatographic GPC column. The chromatography is performed with Omnifit glass column of 5 cm diameter that was filled with a slurry of 700 mL Toyopearl HW-65F in 40 mM sodium phosphate buffer. The slurry was allowed to settle slowly, followed by washing with 40 mM sodium phosphate buffer (pH=6.9) at increasing flow rate from 10 mL/min to 60 mL/min. The column was installed in a preparative HPLC device consisting of two feed pumps, a UV detector, sampling valves and a computer. The reaction mixture from the annealing was loaded on the column and eluted with 40 mM sodium phosphate buffer (flow=50 mL/min, pH=6.9). Target fractions were taken when the UV signal was between 100 mV and 1250 mV, and pooled for further work-up using four desalting cycles of dilution and concentration using a tangential flow device (TFF, Millipore Pellicon 2, regenerated cellulose, equipped with three membrane cassettes of 0.1 m² each, 300 kDa cut-off). Inlet and outlet were connected to the first glass bottle with the pooled chromatography fractions. Final retentate and washing solution were filtered over a membrane to give a clear, colorless solution that was desalted using isopropanol, freeze-dried, and lyophilized at room temperature (at 1 mbar for approx. 5 days).

Different commercial In vivo-JetPEI [having an average molecular weight comprised between 8.3 and 22.5 kDa, and a polydispersity index <1.5, as determined from that of PEOX (polyethyleneoxide, precursor to PEI) by Gel Permeation Chromatography (GPC: SOP GPC-0044) and sterile filtered through a 0.2 µm filter] was obtained from PolyPlus (catalog no. 201-50G). The 2-vial process involves mixing the content of a Vial 1 containing poly(I:C) molecules (volume of 1.0 mL or less, when fast pipetting the solutions, or up to 5.5 mL, when using a syringe) with a Vial 2 containing PEI solution (volume of 1.0 or less mL, when fast pipetting the solutions, or up to 5.5 mL, when using a syringe). Alternatively, the content of Vial 1 is aspirated with a syringe (10 mL) and needle (G20-0.9 µm) and quickly shot over the surface of the liquid in Vial 2. Resulting BO-111 preparation is then filtered through a membrane having a pore size in the 1-5 µm range, ensuring elimination of larger, visible particles. Glucose (or mannitol) was included as an excipient in Vial 1 to reach 5% (w/v) concentration in the final BO-111 preparation [i.e. said composition is formed by additionally adding glucose (or mannitol) in a concentration of 5% (weight/total volume of said composition)]. Glucose has been extensively used as an excipient that promotes an acceptable osmolality of BO-111 (302 mOsm/Kg) without compromising functional or physico-chemical features and avoiding potential undesired side effects due to the administration of mannitol at high concentrations.

Distinct BO-111 preparations were produced by filtering once or twice the initial BO-111 solution through cellulose acetate membrane of different pore size (Minisart® NML Syringe Filters; Sartorius) according to manufacturer's instructions. Alternatively, the initial BO-111 preparation was centrifuged for 15 minutes at the indicated speed using a fixed-angle rotor FA-45-24-11 for Centrifuges 5415 D/5415 R (Eppendorf). The flow through of membrane filtration and the centrifugation supernatant, respectively, were stored until use at 4° C. at a poly(I:C) concentration of 0.5-0.8 mg/mL as determined by UV. Poly(I:C) concentration is then re-calculated before each experiment, generating sample with the same dose for every condition.

The size of poly(I:C) molecules within BO-111 preparations was determined using agarose gels and unlabeled or [$^{32}$P] labeled poly(I) and poly(I:C) preparations. Briefly, 1 µg of poly(I) and poly(I:C) (PBS) are loaded into the agarose gel and electrophoresis was performed for 1 hour at 80 volt in TBE buffer. Depending from the size distribution of initial poly(C) and poly(I) molecules, the size distribution of poly(I:C) molecules that are present in BO-111 preparations was determined as being: <400 bases, 7-57% (with further tests performed using preparations presenting, for instance, 15% or 21%); 400-850 bases, 20-45% (with further tests performed using preparations presenting, for instance, 25% or 27%); 850-5000 bases, 20~70% (with further tests performed using preparations presenting, for instance, 52% or 53%); >5000 bases, 0-9% (with further tests performed using preparations presenting, for instance, 1% or 0%).

Analytical Technologies

The value for zeta average (z-average) diameter and polydispersity index of JetPEI/poly(I:C) particles in distinct BO-111 preparations (between 0.5-0.8 mg/mL, to be diluted for cell-based and other assays at a poly(I:C) concentration of 1.0 µg/mL) were determined using Zetasizer Nano ZS according to the manufacturer's instructions and in accordance with ISO 22412, based on the assumption that said particles are spherical. In general, dynamic light scattering (Nanosizer technology) is applied using v7.11 software.

Functional Characterization of BO-111 Preparations

The different BO-111 preparations were tested using human melanoma cells, human pancreatic cells, or human melanocytes according to the literature describing the properties of BO-110 complexes (Pozuelo-Rubio M et al., 2014; Tormo D et al., 2009; WO2011003883). Briefly, cell viability assays were performed on adherent cells at least 12 hours before treatment. The percentage of cell death at the indicated times and treatment concentrations was estimated by standard trypan blue exclusion assays on floating and adherent cells that were pooled, stained with a 0.4% trypan blue solution (Gibco Laboratories, Grand Island, NY, USA) and scored under a light microscope (a minimum of 100-500 cells per treatment were counted). Each preparation was tested for a period comprised between 12 hours and 48 hours and at concentrations poly(I:C) molecules in the different preparations that were comprised between 0.1 and 2.5 g/mL.

Results

Existing process for the preparation of BO-110 complexes as described in the literature (Pozuelo-Rubio Met al., 2014;

Tormo D et al., 2009; WO2011003883) have been established on a laboratory scale and have some important limitations with respect to requirements for generating materials that can be tested on larger pre-clinical scale, and then for clinical evaluation: limited concentration (not beyond 0.05 mg/mL) and limited possibility for up-scaling and, at the same time, making the manufacturing process GMP-compliant. In particular, the manufacturing process should allow producing batches of formulation comprising poly(I: C)-containing particles having physico-chemical features (such as sterility, particle size distribution, stability, lack of visible and sub-visible particles, and concentration of at least 0.5 mg/ml) as uniform as possible among distinct preparations for correctly evaluating their biological effects and medical use in relevant pre-clinical models and pharmaco-toxicological assays.

A first step in reaching these objectives was to substitute the step of adding drop-by-drop poly(I:C) solution to JetPEI solution (or other way around, as in initial BO-110 preparations; WO2011003883) and incubating the mixture at room temperature. The speed of mixing was identified as a potentially important, yet not evaluated, factor for solving the manufacturing problem. At this scope, a new type of poly(I:C)-PEI formulation, named as BO-111, was established by substituting the approach of bulk mixing of solutions to be lyophilized and packaged into vials, with the approach of producing two vials, each containing the desired amount of JetPEI and poly(I:C) molecules. The content of the two vials are rapidly mixed by injecting (or by other means for rapidly mixing liquids, such as fast pipetting), the two solutions having similar volume. The resulting solution has a volume compatible with later assays and uses (e.g. a 1.2 mL BO-111 preparation at 0.5 mg/mL, resulting from mixing 2 solutions, each having a volume of 0.6 mL).

The syringe and needle used for the mixture generate enough turbulence for promoting fast mixture and rapid formation of particles in BO-111 preparations, with limited (or absent) visible particulate. Specific technical details of BO-111 manufacturing process may be adapted in order to provide a further increased level of activity, reproducibility, stability, and/or homogeneity of BO-111 preparations, for instance by extracting salts, eliminating production residues, filtering the solutions with filters with large pore sizes (e.g. in the range between 1 and 5 µm), fast pipetting or vortexing the two solutions, selecting syringe size/diameter, quickly adding poly(I: C) solution to JetPEI solution and not the opposite, or lyophilizing preparations using compounds like glucose or mannitol as excipient.

However, such details can hardly be transferred from small volumes for single or immediate use to a larger scale preparations of GMP-compliant, pharmaceutical formulations that are based on JetPEI as carrier and contain poly(I: C) molecules at the sufficiently high concentration (at least 0.5 mg/mL) and uniform concentrations that are required for testing high doses during pharmaco-toxicological or other pre-clinical evaluation. Moreover, the step of mixing components of BO-111 just before administration leaves in the technician's hands the good quality of the final material, in particular with respect to formation of clear, not turbid solutions that contain BO-111 particles having larger, and not fully controlled, diameter (size) range.

In this context, the aim in the next step was to evaluate different means and effects of standardizing the diameter of BO-111 particles mixture. The initial BO-111 preparation that was obtained by the 2-vial, fast pipetting process was used for generating and comparing alternative preparations in which concentration and/or size of the solute, such as BO-111 complexes, are altered within the solution by using common technologies such as centrifugation at high speed (e.g. beyond 5000 rpm) and filtration (e.g. with pore size in the 1-5 µm range or in a sub-micromolar range).

Figure 1B:
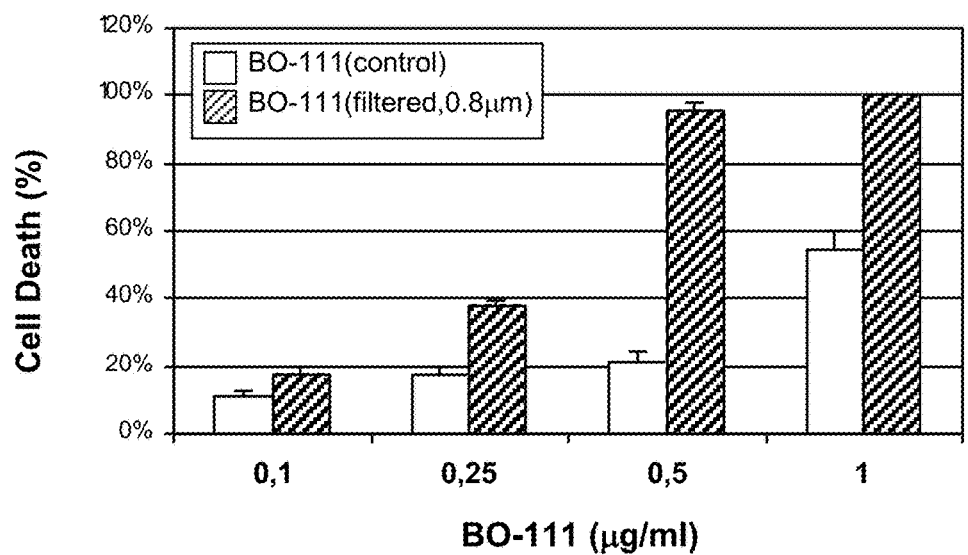

This initial analysis shows that, by applying either technologies, the resulting BO-111 preparations not only presents a reduction in average BO-111 particle diameter, but also a surprisingly increase of cytotoxicity of such preparations against cancer cells that is proportional to the decreased average diameter of BO-111 complexes (FIG. 1A). Such increased anticancer effect was also confirmed in a dose response study showing that the flow-through BO-111 solution, being obtained by filtering the initial BO-111 solution with the larger sub-micromolar pore size, presents an already important increase of the anticancer effects of BO-111 complexes, especially at lower BO-111 concentrations (FIG. 1B). A similar increase in cytotoxicity is also confirmed by using BO-110 preparations that are filtered through a filter having a 0.8 µm pore size.

Figure 2A:
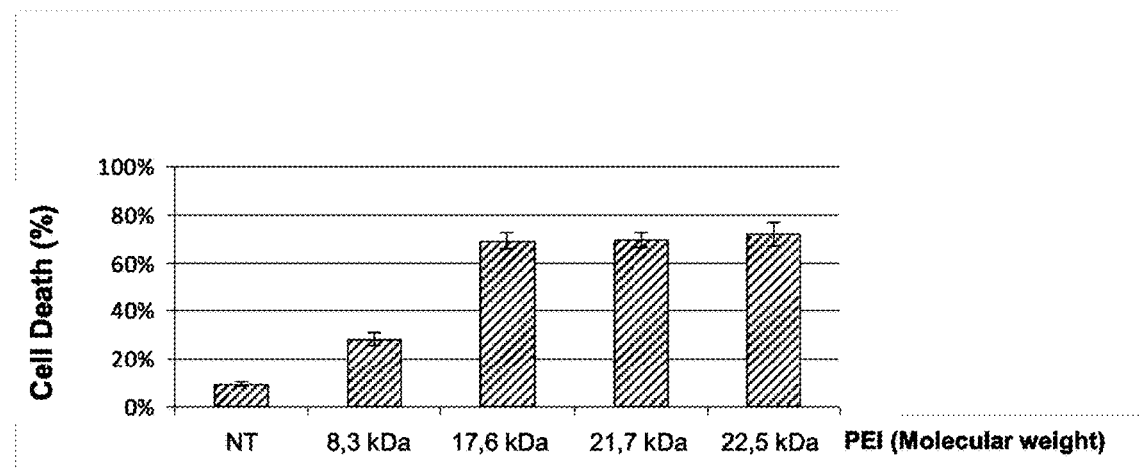
FIG. 2A and FIG. 2B show the effects of PEI features on BO-111 functional activity, as determined using the same cell-based assay and BO-111 concentration of FIG. 1A and FIG. 1B.

Further criteria that can be evaluated are those related to JetPEI features and ratio with respect to poly(I:C) molecules. At the structural level, JetPEI preparations including linear PEI within a range of average molecular weight were tested using the 2-vial process. The comparison of the cytotoxicity of such BO-111 preparations (FIG. 2A) showed that linear PEI of higher molecular weight (e.g. between 17 and 23 kDa) provide anticancer BO-111 preparations that are more effective than those including linear PEI having lower molecular weight (e.g. 8.3 kDa).

Figure 2B:
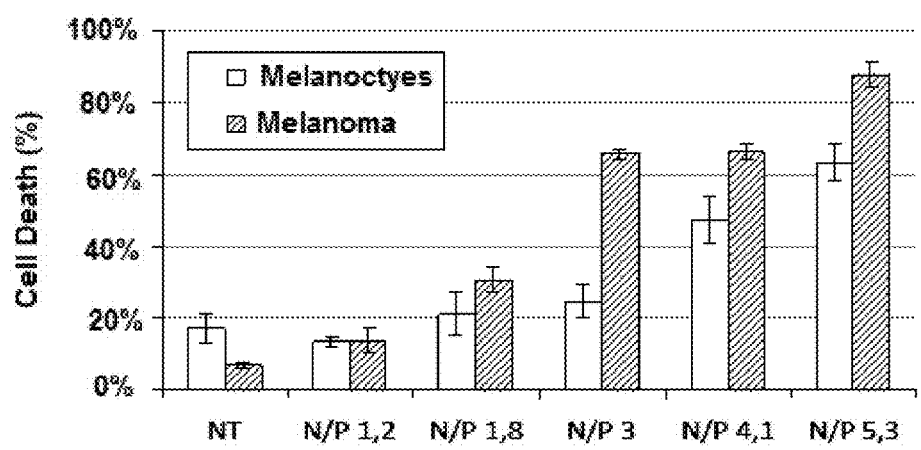

In addition to defining a range of linear PEI sizes that are suitable for manufacturing BO-111 having the desired anticancer properties, the effect of different concentration ratio between amines of PEI and anionic phosphate of poly(I:C) molecules was tested in the context of BO-111 manufacturing. The ionic balance between JetPEI and poly(I:C) molecules may provide complexes that present different level of interactions with cellular components (e.g. for effective cell entry). This balance is calculated as the N/P ratio, defining the number of nitrogen residues of JetPEI per polyribonucleotide phosphate, a value that, for in vivo polyribonucleotide delivery experiments, is recommended as being between 6 and 8 (avoiding the toxicity problems beyond 8, that is 0.16 µL JetPEI per µg double-stranded poly(I:C) molecules). Distinct BO-111 preparations showed a dose-response cytotoxic effect on both melanoma cells and normal melanocytes when increasing such ratio N/P from 1.8 to 5.2. Indeed, only at an intermediate range (around the ratio N/P of 3) cytotoxicity against melanoma cells is well superior to the one against normal melanocytes, viability of latter cells being only marginally affected by this specific BO-111 preparation when compared to untreated cells (FIG. 2B).

The BO-111 preparations have also been analyzed for the content of poly(I:C) molecules using labeled or unlabeled poly(I:C) batches. The initial poly(I:C) batch preparation comprises double stranded poly(I:C) molecules that, consequently to their manufacturing and their annealing, have a size distribution up to 5 kilobases of length (or more), with at least 40% or 50% of such double-stranded with a size higher than 0.85 Kb and at least 70% of such double-stranded polyribonucleotides with a size comprised between 0.4 and 5 Kb (in a representative preparation, <400 basepairs (bp): 21%, 400-850 bp: 27%, 850-5000 bp 52%). When poly(I:C) molecules are associated to JetPEI in complexes within BO-111 preparations using the 2-vial process, the totality of poly(I:C) molecules is associated with JetPEI, as shown by agarose gel analysis with unlabeled or labeled poly(I:C) preparations (FIGS. 3A and 3B). By electrophoresis it has also been determined that, in BO-111 preparations at N/P ratio below 3, poly(I:C) molecules are not fully associated with JetPEI, as it can be observed with higher N/P ratio (3 or above; FIG. 3C). Thus, an appropriate manufacturing process allows incorporating efficiently poly(I:C) molecules with a wide size distribution into biologically functional BO-111 preparations, without adding a specific procedure for removing uncomplexed poly(I:C) molecules or JetPEI.

Figure 4A:
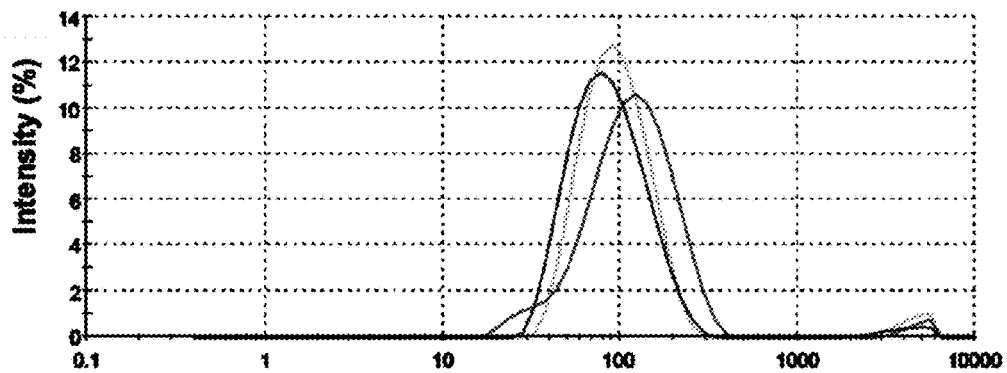
FIG. 4A to FIG. 4D show the size distribution of BO-111 complexes in preparations that are obtained using the 2-vial production process, as determined by comparing signal intensity using Dynamic Light Scattering by zeta sizer nano ZS technology.
Figure 4B:
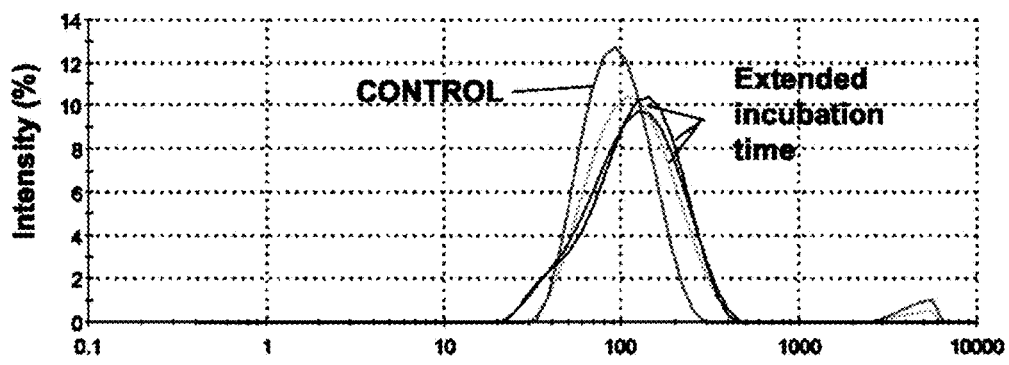
Figure 4C:
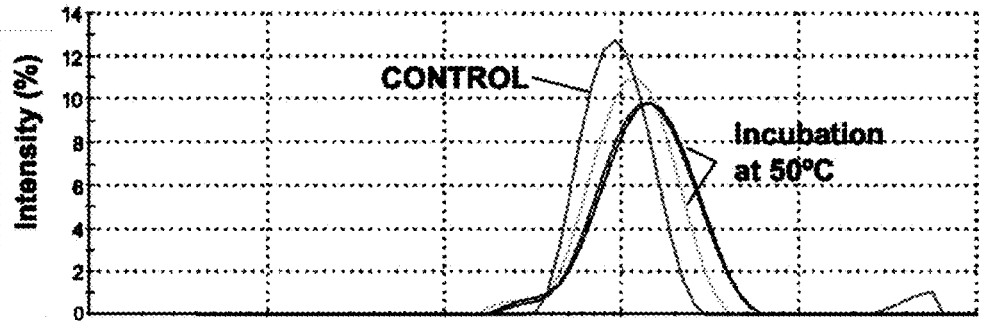
Figure 4D:
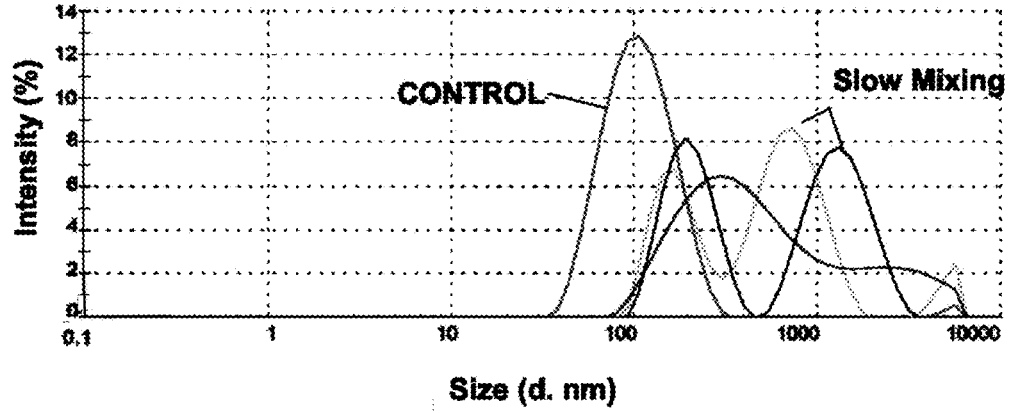

Structural BO-111 features were evaluated also by using technologies for establishing the size distribution of particles in the sub-micrometer range when the manufacturing process is repeated or modified, or when BO-111 preparations are tested for their stability. The reproducibility of this manufacturing process is demonstrated given that distinct BO-111 preparations are always presenting a mono-modal distribution of particle size, with diameters that are mostly concentratedaround 100 nm, most often between 50 and 90 nm (average diameter (d. nm) of 85-90 nm), with a large majority of particles having a size below 100 nm, or 200 nm, but not exceeding 400 nm, but commonly even not exceeding 300 nm (FIG. 4A). When this reference BO-111 preparation is exposed to variations in temperature or incubation time, the diameter distribution can change, but it is still mono-modal, peaking between 100 and 150 nm (average diameter (d. nm) of 105-110 nm), with a large majority of particles still having a diameter below 300 nm and not exceeding 600 nm (FIGS. 4B and 4C). The corresponding BO-111 preparations still present a similar cytotoxicity level when tested as described for FIG. 1A, FIG. 1B and FIG. 2A, FIG. 2B, demonstrating that this mixing procedure can provide formulations consistent with requirements for pharmaceutical development. However, modifications of the process, such as reducing the mixing speed or not introducing filtering procedures may alter the size distribution of BO-111 complexes, becoming bi-modal, with a poorly controlled and higher average size (d. nm) and a large majority of particles exceeding 500 nm (FIG. 4D).

These experiments show that the manufacturing and formulation process of the complex named BO-110 can be improved by applying a fast and controlled mixing of components at small scale prior to their use, leading to a more uniform, concentrated, and effective poly(I:C)-based preparation named as BO-111. However, further improvements are needed to generate preparations presenting fully GMP-compliant preparations for the highest stability and efficacy features independently from a procedure to be established just before medical use. In particular, the "fast pipetting" method or other variations of the 2-vial process may still provide a considerable amount of particles having a diameter above 200 nm (up to 1 μm or several micrometres). The additional (and possibly only partially efficient) filtration step that would be required in order to provide the desired sterile and concentrated BO-111 preparations (presenting functional complexes of smaller, more narrowly distributed, uniform diameter around 100 nm) can have the consequence of losing a large amount of material that is retained in the membrane filter. Thus, even though the initial approach has allowed establishing small scale BO-111 preparations with an inverse relationship between BO-111 complex diameter and its therapeutic activity, further technical improvements are required for establishing and mixing poly(I:C) molecules and JetPEI solutions in a manner that is convenient for the bulk manufacturing of GMP-compliant, stable pharmaceutical formulations that comprise poly(I:C)-based complexes with a narrow and controlled size distribution and that can be then used for producing several vials each having controlled and comparable features [such as poly(I:C) content, complex stability, and biological activities of the formulations].

Example 2:1-Vial Process for Production of BO-11X Preparations Under GMP-Conditions (BO-112 Formulation)

Materials & Methods
Manufacturing BO-112 Preparations (1-Vial Process)

Poly(I:C) preparations are produced as solutions having concentration, molecule size distribution, and in accordance to the protocol as described in Example 1. However, in one batch, poly(I:C) was itself obtained by the following exemplary process: poly(C) solution was heated at 61 to 66° C. for 1.5 h before mixing this with the poly(I) solution and stirring at 55 to 58° C. for 70 minutes, after which the mixture was cooled and filtered over a 0.2 μm membrane. Some conditions applicable to the chromatography and/or filtration step, absence or presence of a freezing step, together with buffer and annealing time, were adapted for further reducing solution viscosity or precipitation of complexes. Either Mannitol or Glucose is used as excipient in the final formulation. Solution 1 containing JetPEI is obtained by either using JetPEI in a concentrated liquid preparation or solubilizing solid bulk preparations of JetPEI (having a molecular weight comprised between 17 and 23 kDa) in an amount of sterile water for injection to reach 150 mM, and mixing for obtaining a homogeneous solution. A further dilution step is performed to reach a concentration of 11.25 mM, before the final dilution to 5.62 mM in the final vial. Solution 2 contains poly(I:C) molecules and glucose monohydrate in an amount that, after mixing with JetPEI, provides a solution formed by adding 5% glucose (weight/total volume of said composition) and poly(I:C) at 0.5-0.7 mg/ml of the total volume of said composition, whereby said poly(I:C) complexes with said JetPEI, thus resulting in a BO-112 composition having from 108 to 1010 particles in solution per vial.

Solution 1 and 2 are independently sterilized using a double filtration through 0.2 μm filters (Sartopore® 2 150 0.2 μm, fully validated as sterilizing grade filters (according to ASTM F-838-05 guidelines) using a pump Watson Marlon (speed 30 rpm). The automated mixing of the two solutions is performed in each vial using a sequential process: (i) Solution 1 is added to the vial using a Watson-Marlow pump to dose 5.95-6.05 g (6 mL; density: 1 g/mL), (ii) Solution 2 is added over the solution 1 using a 1.8 mm internal diameter tube connected to a G20-0.9 μm needle using Flexicon pump at 550 rpm speed to dose 6.08-6.40 g (6 mL). Results can be improved by using a T-piece mixer. In case of aggregates of particles (e.g. with a size in the range of 1-100 μm or larger) that may be still present by visual inspection at the end of the manufacturing process (or during its storage) due to electrostatic interactions, the product can be filtered over a 0.8 μm filter prior to use (for instance, before its injection), therewith altering neither biological properties nor mono-modal diameter distribution of the particles within the composition. For example, the BO-112 formulation can be filtered through a Minisart Syringe Filter (Sartorious) with an exclusion size of 0.8 μm. Vials are sealed with sterile pyrogen-free rubber stoppers and crimp with aluminum capsules and individually labelled.

Commercially Available Poly(I:C)-Containing Formulations

Poly-ICLC is a poly(I:C) preparation that is stabilized with polylysine and carboxymethyl-cellulose (Ewel C et al., 1992; WO2005102278). LyoVec-HMW (Cat. No. tlrl-piclv) and LyoVec-LMW (Cat. No. tlrl-picwlv), and corresponding poly(I:C) preparations having high molecular weight (HMW; Cat. Name tlrl-pic) and low molecular weight (LMW; Cat. Name tlrl-picw) are available from Invivogen.

Analytical Tests

The diameter and distribution analysis of BO-112 was performed according to Example 1 using standard Dynamic Light Scattering equipment.

Results

The definition of BO-11X preparation applies to the pharmaceutical compositions that are obtained by appropriately mixing a solution containing a polymer like PEI with a solution containing poly(I:C) molecules in order to generate complexes having small, narrowly distributed particle diameter range (as defined by z-average diameter peaking between 50 and 100 nm and not exceeding 300 nm, or even 200 nm, as shown in Example 1). If BO-111 preparations result from a mixing step that is performed manually just before further use (i.e. the "2-vial process"), GMP-related and other industrial requirements (e.g. for automating the process) have been taken into account for establishing a "1-vial process" that provides a BO-11X formulation complying with the required pharmaceutical specifications and ready to be injected. At this scope, the two solutions are separately prepared (and, in the case of poly(I:C) solution, including also one or more excipient) and sterilized by filtration before being mixed in automated system wherein speed and time of mixing are controlled and maintained for each vial.

Figure 5A:
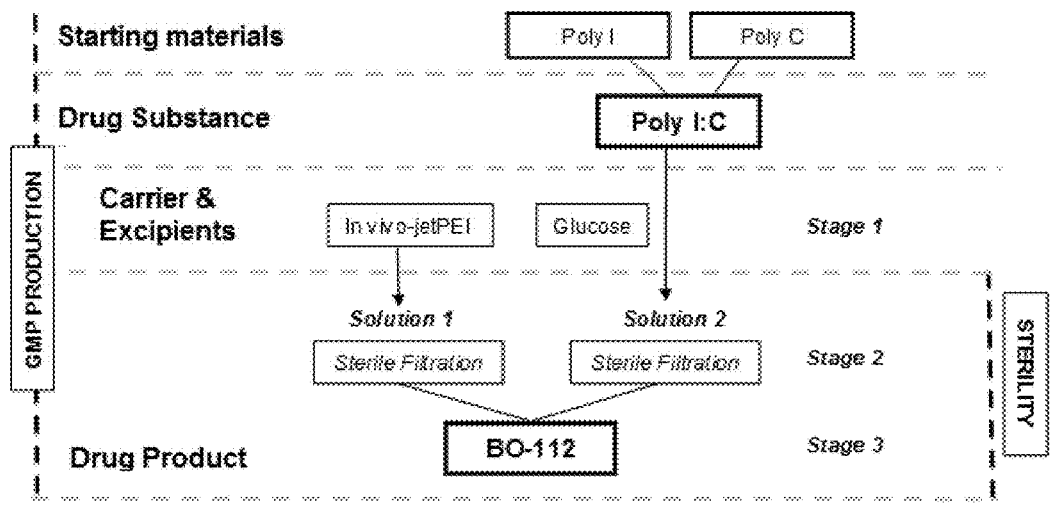
FIG. 5A and FIG. 5B show a scheme of GMP manufacturing of BO-11X compounds, as exemplified by BO-112.
Figure 5B:
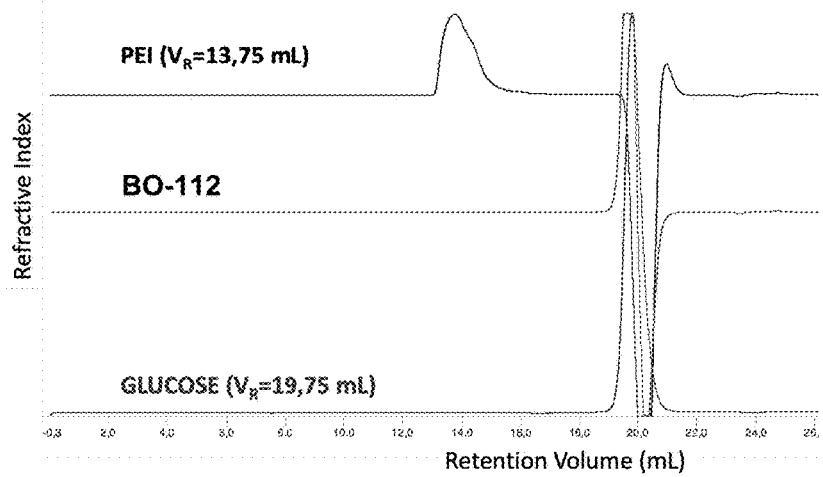

FIG. 5A and FIG. 5B provide an overview of such process for generating a first type of BO-11X preparations that is named BO-112 formulations wherein the drug substance (i.e. double stranded poly(I:C) molecules that are generated by annealing of poly(I) and poly(C) single-stranded molecules) is first mixed with an excipient like glucose in a solution that is sterilized by filtration, separately from the solution containing a polymer having the function of carrier (i.e. JetPEI). Then, these two bulk preparations are appropriately mixed into each vial to generate a large number of structurally and functionally comparable pharmaceutical formulations that are required for pharmaco-toxicological studies and clinical applications.

Figure 5C:
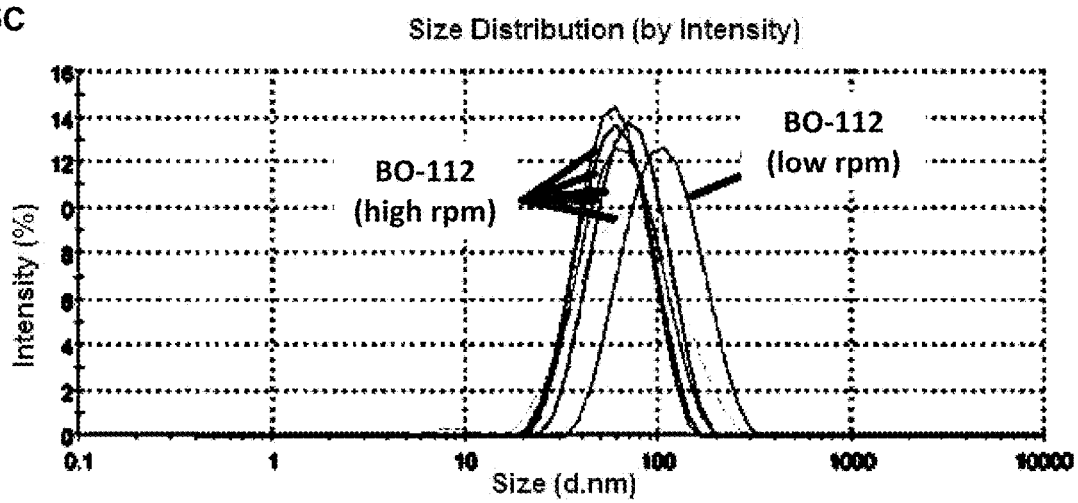
FIG. 5C Modification of BO-112 compound distribution due to increased speed of mixing during manufacture process at low (below 100 rpm) or at high (beyond 100 rpm, up to 550 rpm) injection speed, where 550 rpm is the reference speed for mixing solutions in the BO-112 manufacturing process, that is for obtaining particles with Z-average diameter (d. nm) going from around 100 nm down to 73 nm, 54 nm or less (functional BO-112 preparations present an average diameter between 30 nm and 150 nm; particle diameter is defined as in previous figures in d. nm).

This approach takes advantage of the findings described in Example 1, and it can be automated for providing BO-112 preparations with even more uniform features. This mixing procedure allows not only to incorporate all available Glucose, JetPEI, and poly(I:C) molecules into complexes within BO-112 preparations (FIG. 5B) but also to modulate average diameter and the mono-modal diameter distribution of the complexes within BO-112 preparations, so that the Z-average can be modulated between 30 and 150 nm (FIG. 5C). The resulting BO-112 preparations present BO-112 complexes having a mono-modal diameter distribution, without visible particles even if the final solution is not filtered through 5 µm after mixing the bulk solutions 1 and 2. The mixing conditions can be adapted, in particular by modifying the mixing speed between 50 rpm and 600 rpm and/or the flow speed for either poly(I:C) or JetPEI Solution between 1 mL/min and 50 mL/min.

In general, BO-11X preparations (and in particular BO-112 preparations) present the following main features: colorless, no visible particles an osmolarity comprised between 260 and 340mOsm/kg, a pH comprised between 2.7 and 3.4, an optical rotation between +1500 and +3750, a zeta potential equal or superior to 30 mV, a mono-modal diameter distribution of particle with Z-average diameter (nm) between 30 and 150 nm, but preferably between 60 nm and 130 nm, and comprising poly(I:C) molecules, wherein at least 40% or 50% of such double-stranded polyribonucleotides with a size higher than 0.85 Kb and at least 70% of such double-stranded polyribonucleotides have a size comprised between 0.4 and 5 Kb. Features such as diameter distribution of the particles can be modified by using T-piece mixer in combination with different flow speed for both Solution 1 and Solution 2. When such speed is above 20 mL/min (e.g. 30 mL/min), the turbidity of the resulting BO-112 preparation is reduced in parallel with the reduction of Z-average particle diameter and diameter distribution around this value, while maintaining mono-modality, possibly due to the change in the flow regime.

The exemplary BO-112 preparation presents a composition similar to BO-111 (formed with 6.924 mg of poly(I:C), 5.625 mM JetPEI, 5% glucose), but each vial comprises particles having a Z-average diameter of between 45+/−5 nm and 81+/−5 nm (e.g. 73+/−5 nm), with at least 50% of particle smaller than 85+/−20 nm, the zeta potential of 38 mV, and pH 3.1. These structural properties that are maintained after freeze/thaw cycle at −20° C. or extensive exposure at room temperature can be modified in distinct batches, maintaining the acceptance criteria within specific ranges of values (for instance, BO-112 formulations can present an Z-average diameter of 100+/−50 nm (e.g. 89 nm), with a potential z comprised between about 40 and 45 mV (e.g. 43 mV) These values may be modified following cryopreservation but they can still be remain within these ranges.

Figure 6A:
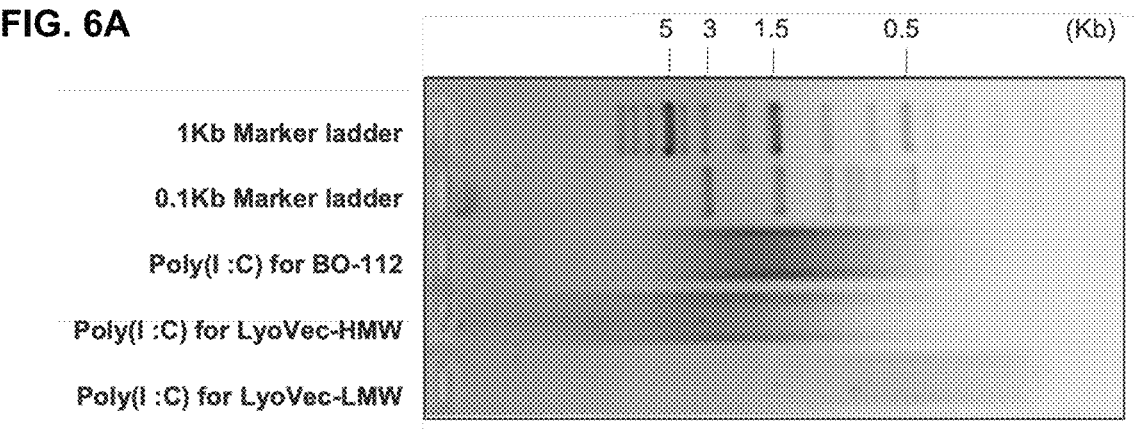
FIG. 6A and FIG. 6B show a structural analysis of different poly(I:C) formulations.
Figure 6B:
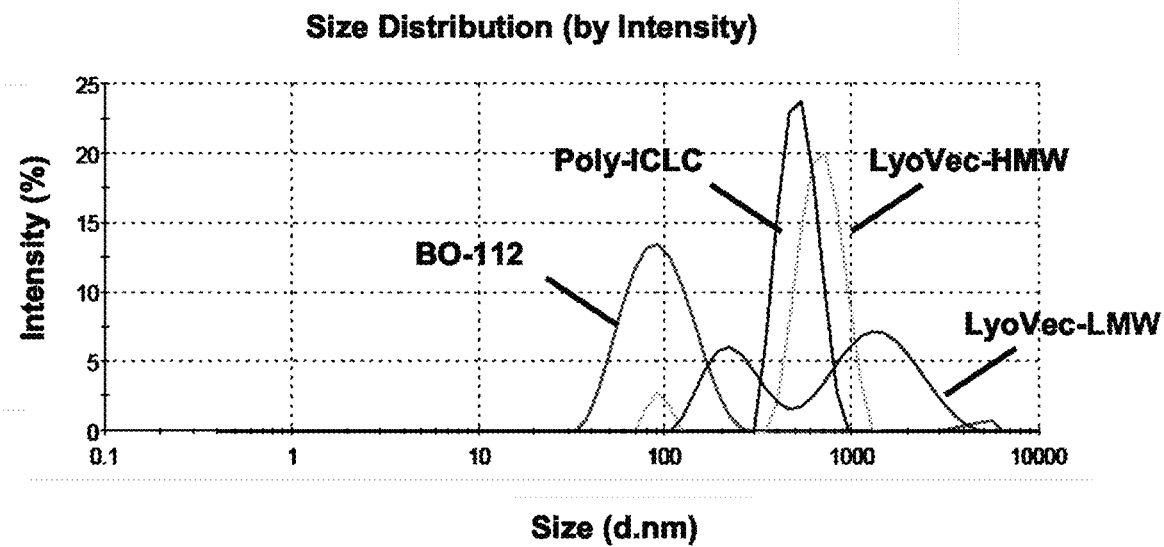
Figure 7A:
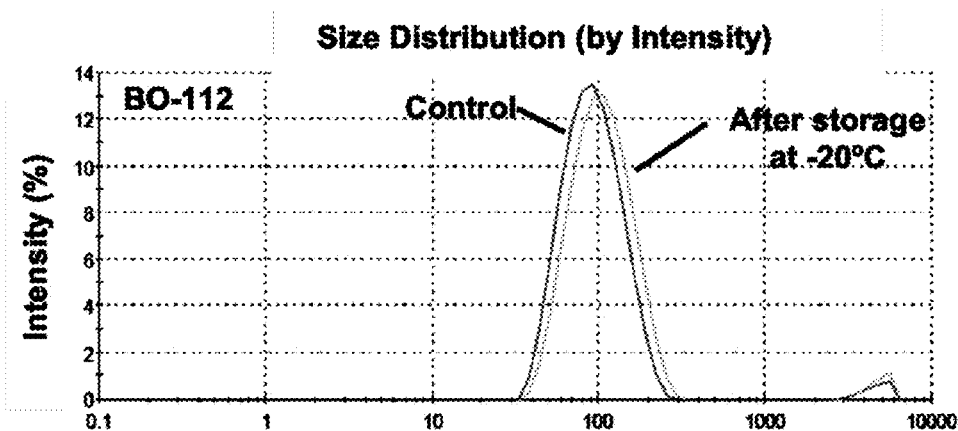
FIG. 7A to FIG. 7D show changes in the size distribution following storage at −20° C. is determined for BO-112 (FIG. 7A), Poly-ICLC (FIG. 7B), LyoVec-HMW (FIG. 7C), and LyoVec-LMW (FIG. 7D), as determined by comparing signal intensity using Nanosizer technology (particle diameter is defined as in previous figures in nm).
Figure 7B:
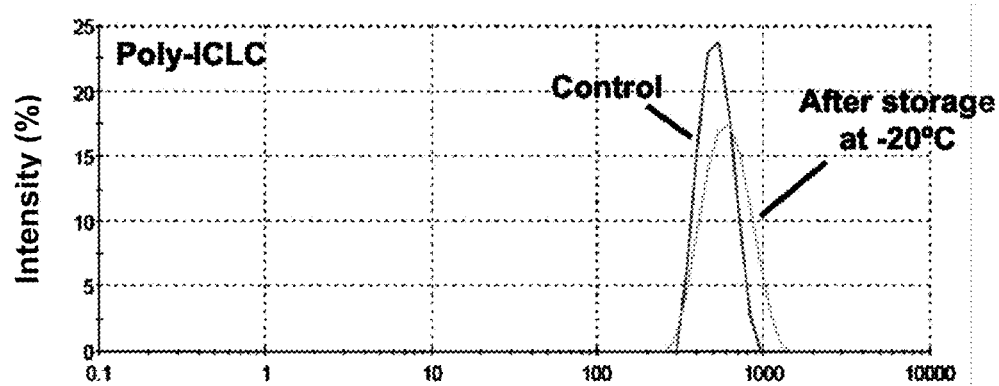
Figure 7C:
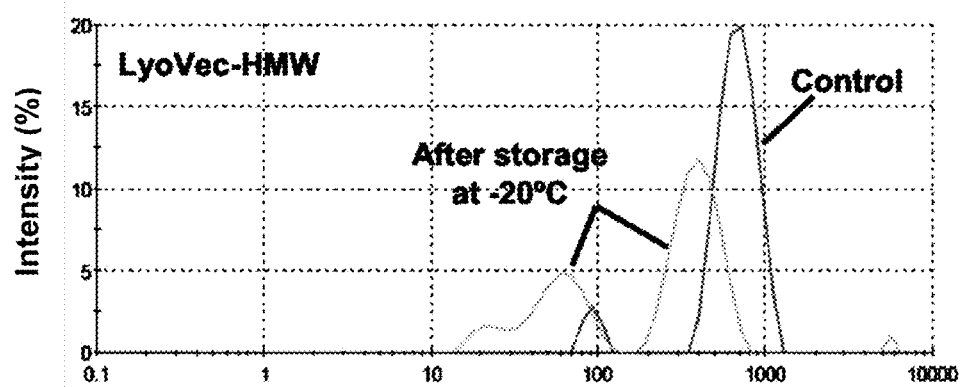
Figure 7D:
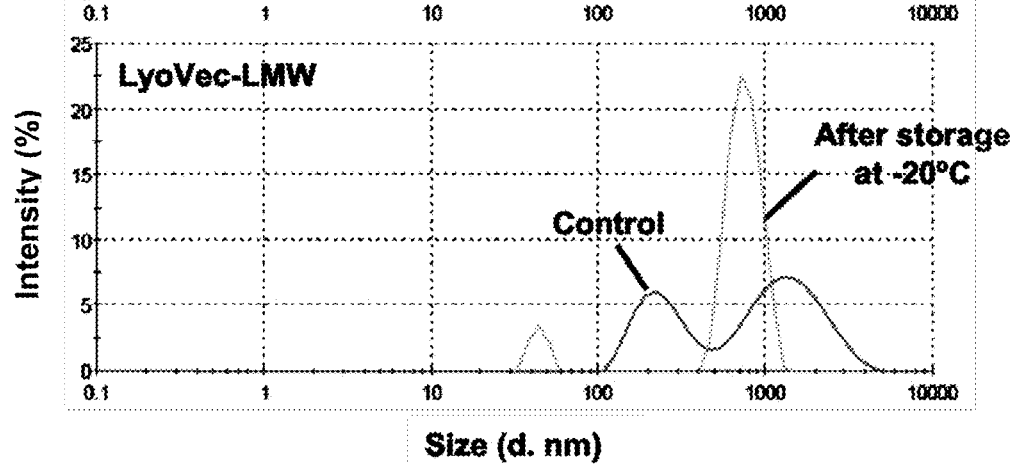

At least some of such reproducibility and acceptance criteria can be compared to the ones of other poly(I:C)-containing formulations for which anticancer activity are known. At the level of poly(I:C) molecules size, the poly(I:C) molecules that are included in the commercial Lyovec-HMW and Lyovec-LMW are covering size ranges that are clearly distinct from those for BO-11X manufacturing process actually makes use of (with HMW almost entirely above 0.85 kb and LMW almost entirely below 0.85 kb; FIG. 6A). This size difference in poly(I:C) molecules may be dependent from the different manufacturing process and/or carrier that are associated in the complexes with poly(I:C) molecules. The Z-average values of complexes within poly (I:C)-based complexes within poly-ICLC (comprising polylysine and carboxymethylcellulose) and LyoVec-HMW/LyoVec-LMW (according to the manufacturer, comprising the cationic lipid-based transfection reagents Di-tetradecylphoshoryl-N, N, N-trimethylmethanaminium chloride, or DTCPTAand the neutral lipid 1,2-Diphytanoyl-sn-Glycero-3-Phosphoethanolamine, or DiPPE) were compared to the one of BO-112 formulations, showing that these commercial formulations contain complexes that are much bigger (in large majority larger than 200 nm) and, at least for Lyovec-LMW, with a bi-modal distribution (FIG. 6B).

If this analysis is performed after a freeze/thaw cycle, these commercial preparations appear also as less stable, with a variability not observed for BO-112 (FIG. 7A-FIG. 7DD). Indeed, if BO-112 formulation a Z-average diameter (d. nm) of 100+/−50 nm (e.g. 82.5 nm), and without exceeding 400 nm, as in BO-111 formulations (see FIG. 4A to FIG. 4D and FIG. 6B), LyoVec-based and Poly-ICLC formulations having a Z-average value well above 300 nm, thus confirming that commercially available poly(I:C) are provided as preparations that are either heterogeneous in composition or include large particles that are poorly characterized functionally and whose size is modified during a freeze/thaw cycle.

Hyperchromicity can be also used to evaluate BO-112 formulation, and in particular the stability of double-stranded poly(I:C) molecules within the particles as a consequence of changes in temperature (or other condition) determining the separation between poly(I) strands and poly(C) strands. BO-112 formulation shown a very low hyperchromatic effect with differences in transmittance at 260 nm lower than 0.2 or 0.1. Stability of frozen BO-11X vials at −20° C. for different time has been also assessed and confirmed.

Filtration, lyophilisation and freezing of BO-112 formulation prior to administration does not promote substantial modifications to the cytotoxic properties, stability, or the structural features on the particles within the composition with respect to the original BO-112 formulation. For instance, compositions maintain D90% below 250 nm, zeta potential between 40 mV and 50 mV, hydrodynamic diameter with a Z-average between 30 and 150 nm, compatibility with the use of glucose as excipient, polydispersity values comprised between 0.1 and 0.6, and other applicable criteria from European Pharmacopoeia).

Thus, BO-11X preparations, such as BO-112 preparations, are formulations that present the high level of stability and reproducibility for particles formed by poly(I:C)-JetPEI complexes having Z-average diameter (d.nm) below 200 nm (when not below 100 nm) that are not observed for commercial poly(I:C) formulations that are based on other carriers and manufacturing methods.

Example 3: Functional Characterization of BO-11X Preparations in Cell-Based Models Materials &Methods
Poly(I:C) Formulations
The poly(I:C) preparations have been obtained as described in Example 2.
Analysis of Cell Viability
The human melanoma cell line SK-MEL-103 and human pancreatic cancer cell line PANC 02.03 have been used as described in Example 1 and the literature that is cited herein, using the poly(I:C) formulations at concentrations that contain poly(I:C) molecules in a range between 0.3 and 2.5 µg/mL (0.85 µg/mL being the most relevant reference value) and exposing cells for a period comprised between 12 and 48 hours.

The death-inducing activity of BO-112 was tested in normal melanocytes and cell lines from melanoma and glioblastoma and compared to isolated components, i.e. poly(I:C) molecules and linear PEI (Jet PEI; Polyplus). Normal melanocytes were isolated from foreskins of asymptomatic donors. Melanoma cells SK-Mel-28, SK-Mel-103, and UACC62 (with mutations in p53, NRAS and BRAF respectively) were obtained from established collections at the ATCC or Memorial Sloan Kettering Cancer Centre (USA) and were subject to short tandem repeat (STR) profiling (GenePrint® 10 System) for cell line authentication. Cells were plated on 96 well plates (6000 cells/well). In triplicate per experiment, with. Poly(I:C) only, BO-110 or BO-112 formulations at 0.5 or 1 µg/ml for a 24h or 40h treatment.
Results
Examples 1 and 2 show experimental data about the initial development and characterization of BO-11X formulations, leading to increased cytotoxicity of BO-11X formulations against cancer cells as compared to BO-110. These data can be further integrated by comparing the BO-11X manufacturing process and resulting poly(I:C)-containing preparations with the processes and preparations that are disclosed in the literature.

Figure 8A:
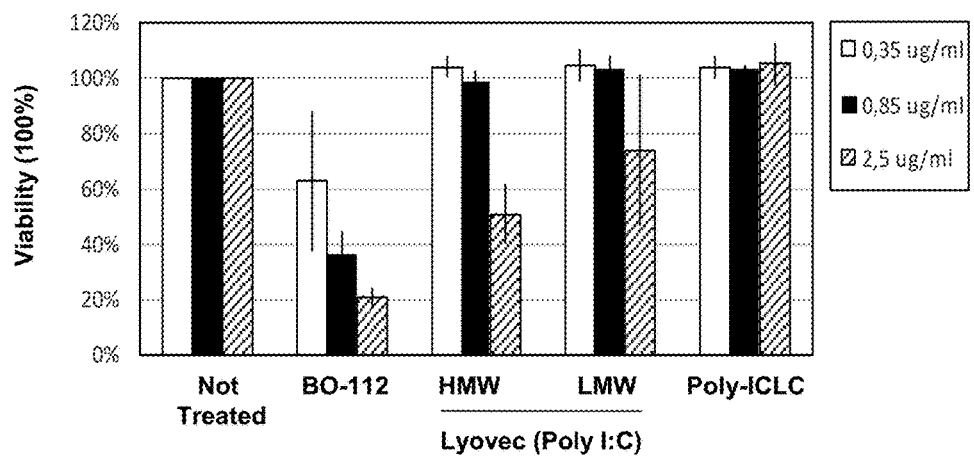
FIG. 8A to FIG. 8C show the effect of different poly(I:C) formulations on cell viability in two distinct cancer cell models. BO-112 is compared to untreated cells and to cells treated with Poly-ICLC, LyoVec-LMW, or LyoVec-HMW, each formulation being tested at the indicated concentrations that were determined according to complex weight but with a similar content of poly(I:C) molecules in either a melanoma (FIG. 8A) or pancreatic cancer (FIG. 8B) cell model. The cell viability data were generated using crystal violet assay method after 24 hours.
Figure 8B:
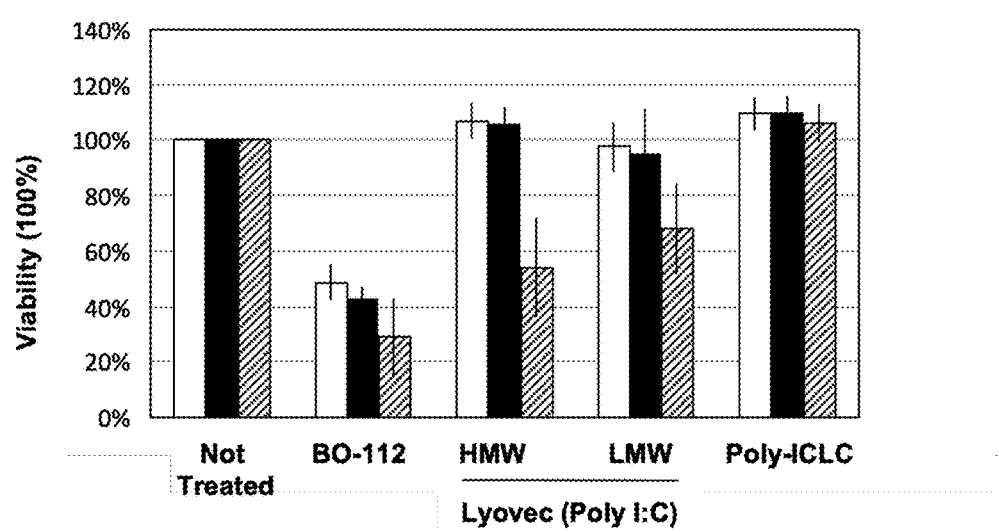
Figure 8C:
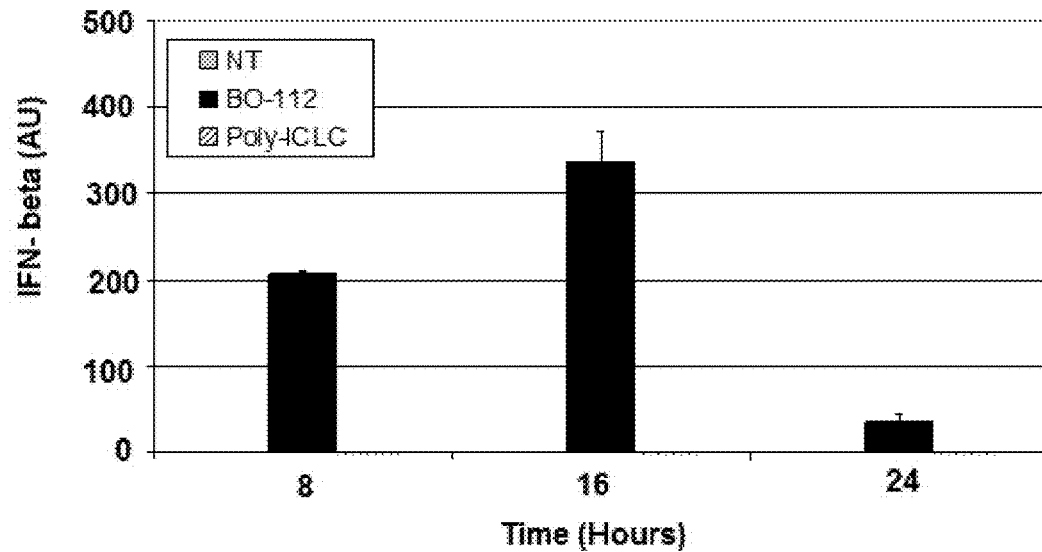

Example 2 has shown that commercial Lyovec-HMW and Lyovec-LMW have a substantially different distribution. However, it can be evaluated to which extent the different size of poly(I:C) molecules in the corresponding poly(I:C) HMW and LMW preparations may also affect the activity of complexes generated using BO-11X manufacturing process and poly(I:C) HMW and LMW. If the cytotoxic activity of BO-112 formulation is compared with commercial formulations, the latter ones appear much less effective in killing cancer cells in at least two in vitro models (FIG. 8A and FIG. 8B). The cytotoxic activity of BO-11X can be measured in different types of cancer cell lines, representative of different clinical cancer indications, to evaluate which cancer indications are more efficiently treated by BO-11X. These effects may be also studied by measuring the expression and/or secretion of proteins that are known to modify, and possibly improve, the cellular response against cancer cells. For instance, a BO-112 formulation induces, much more efficiently that Poly-ICLC, Interferon-beta expression in a melanoma cell line over a period of at least 24 hours (FIG. 8C). This in vitro evidence can be used for evaluating not only which types of cancer can be more efficiently treated by administering a BO-11X formulation but also for evaluating which other cancer treatments (such as vaccines, adjuvants, antibodies, chemotherapeutic drugs, radiotherapy, immunotherapy, or inhibitors of enzymatic activities such as kinases) may act in a more effective manner when administered in combination with a BO-11X formulation (e.g. by reducing the dosage, the frequency, and/or the period of treatment with this other approach).

Figure 9:
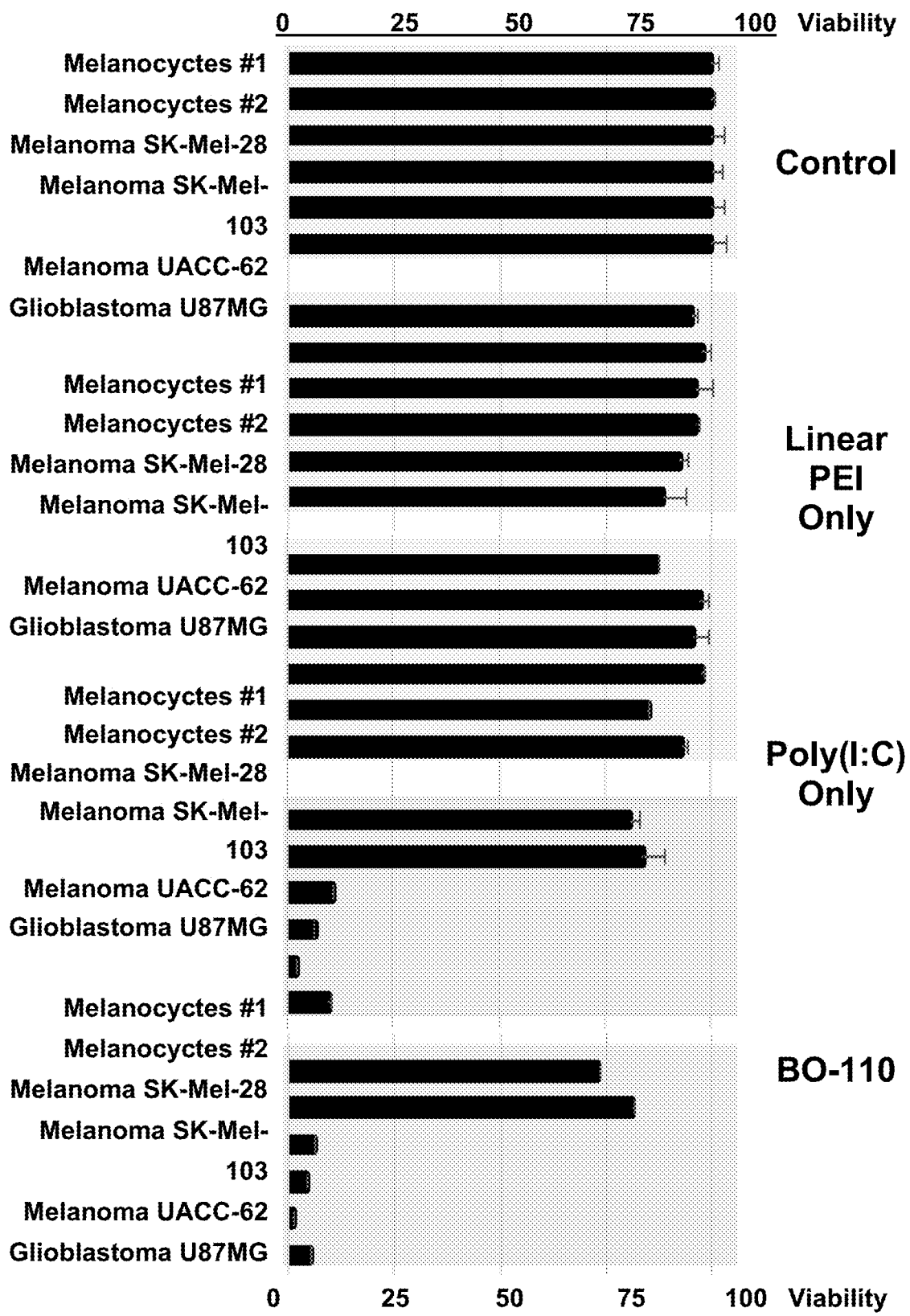
FIG. 9: Effect of linear PEI alone, poly(I:C), and two different PEI/poly(I:C) formulations (BO-110 and BO-112;) on the viability of normal, primary melanocytes (preparations #1 and #2) and four cancer cell lines, demonstrating the specific cytotoxicity of such PEI/poly(I:C) formulations against cancer cell lines. Poly(I:C) content used in preparation of the Poly(I:C) only, BO-110, and BO-112 treatments administered is identical (1 µg/mL per 40 hours of treatment).

Indeed, the specificity of such cytotoxic effects against cancer cell lines, and not against normal primary cells, by BO-11X formulations (as previously described for lab-scale BO-110 formulations; Tormo D et al., 2009) was confirmed in vitro by comparing the activities with appropriate compounds and cell controls (FIG. 9). Neither linear PEIL nor poly(I:C) molecules alone affect in a significant manner the viability of tumor cells (melanoma or glioma. Only when linear PEI and poly(I:C) molecules are complexed, a significant killing of tumor cells, without affecting viability of normal melanocytes, is observed. Similar cell-based approaches have been used for validating BO-11X, and BO-112 formulation in particular, that have been exposed to filtration, lyophilisation, and/or freezing, confirming that the cytotoxic effects are qualitatively and quantitatively maintained in BO-112 preparations after such processes. More in depth analysis of these in vitro data for guiding clinical development can be performed using different pre-clinical models involving the production and the comparison of different BO-11X formulations, different administration regimens, and/or conditions associated to a disease such as cancer.

Example 4: Functional Characterization of BO-11X Preparations in Animal Models

Materials &Methods
BO-11X Formulations and Other Compounds
BO-112 formulations have been obtained as described in Example 2, and diluted with a 5% glucose PBS solution (vehicle; ref: BE14-516F, Lonza, France) into three different concentrations in accordance with a dosing amount per kilo bodyweight of the animal of respectively 0.05 mg/Kg, 0.5 mg/Kg and 2.5 mg/Kg.

Murine anti-PD-L1 antibody (InVivoPlus, clone 10F.9G2) was chosen as combination immunotherapy compound. Each day of injection to mice, anti-PD-1 antibody was diluted with vehicle at final concentrations of 1.5 mg/mL.

Results

Figure 10A:
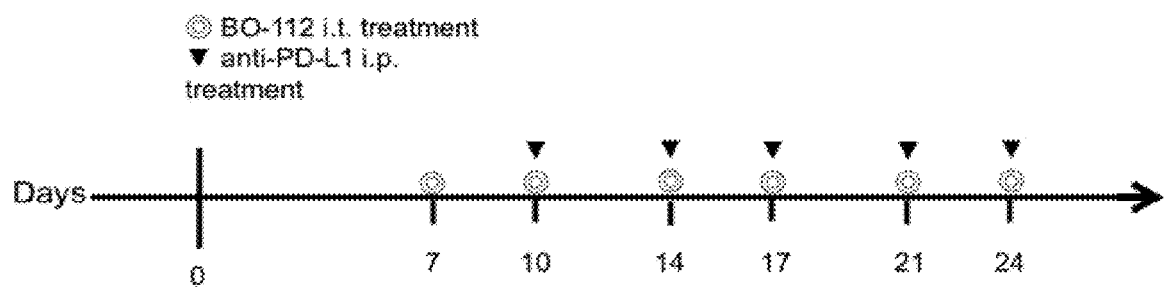
FIG. 10A and FIG. 10B show an effect on BO-112 administration in an animal model for human cancer.
Figure 10B:
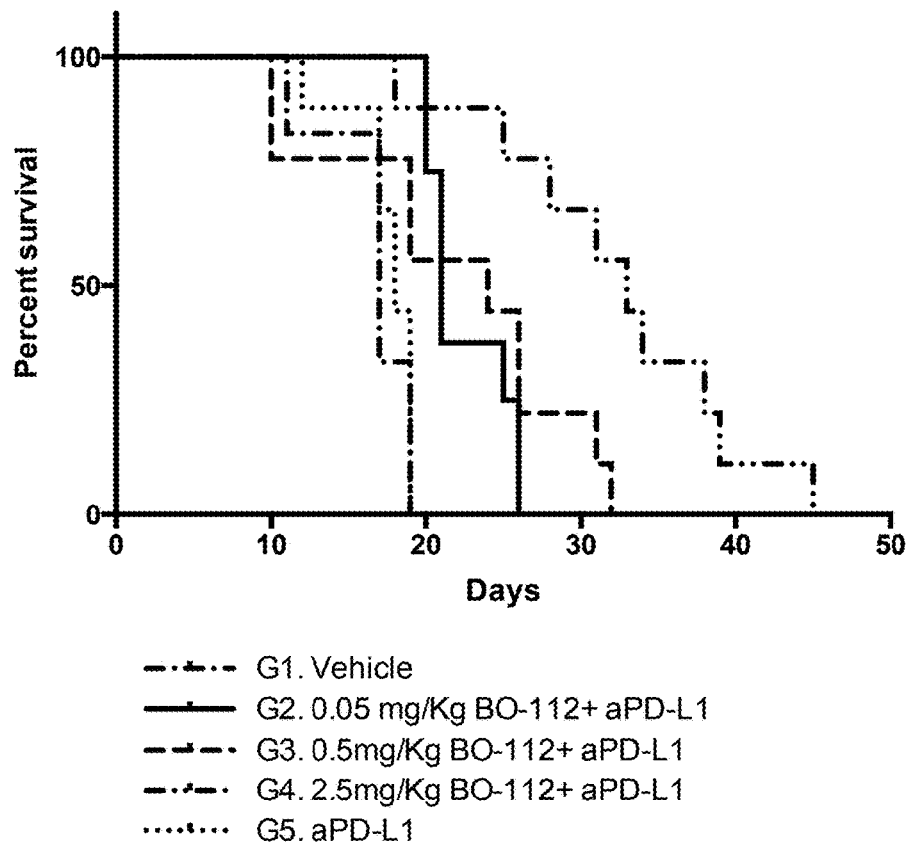

The anti-cancer, in vivo efficacy of BO-112 formulation was investigated for in vivo in an immune competent mouse strain, implanted with mouse melanoma cells. Mice were treated either with a PBS solution or a BO-112 formulation at three different concentrations (0.05, 0.5, or 2.5 mg/kg, preferably administered intratumorally), in combination with a murine anti-PD-L1 antibody (preferably administered intravenously) and compared to the vehicle alone throughout 3 weeks (FIG. 10A). The anti-PD-L1 antibody in combination with the vehicle did not significantly increase survival when compared to vehicle alone. All three BO-112 formulations combinations tested with anti-PD-L1 (and possibly independently form such antibody) significantly increased survival of the mice compared to vehicle or anti-PD-L1 alone. Moreover, survival significantly increased in the combination of 2.5 mg/kg BO-112 formulation+anti-PD-L1 compared to the lower doses of BO-112 formulation. These results correlated with measured tumor sizes in these groups.

Anti-PD-L1 antibody is an important and validated anti-cancer drug, and mediator of an effective immune response against the cancer cells. Our experiment demonstrates that BO-11X complexes can be used in combination with other anti-cancer agents, and that the combination of BO-11X compounds with other anti-cancer agents such as anti-PD1 has superior potency to the anti-cancer agent alone, leading to significant increases in survival and anti-tumor efficacy. Moreover, the improvement in survival correlates with an increase in dose of BO-11X formulation to the combination, supporting that the added benefit in survival is mediated through the BO-11X formulation.

Thus, BO-11X formulations can be used (alone or in combination with other anti-cancer agents, such as antibodies, immunotherapy, or chemotherapy, that can be administered using the same or a different route) in treating melanoma and other cancer indications, in particular those allowing peritumoral or intratumoral injection such as in pancreatic, endometrial, ovarian, or colorectal cancer. At this scope, the identification of specific biological pathways and mechanisms of action may guide the most appropriate dosages, regimens, combination with other drugs or therapies, and indications for BO-11X formulations, as shown for combined effects of immunomodulatory monoclonal antibodies targeting PD-1 or CD137 and poly(I:C) that enhance the activities of dendritic cells (Sanchez-Paulete A R et al., 2015). To this end, Duewell P et al., 2015 discloses an alternative animal model of disease that may be used for testing the composition of the present invention.

BO11X therapeutic effect on tumor growth (locally and/or in distal locations) and the anti-tumor immune response can be measured by performing In vivo studies on Intratumoral (i.t.) administration across at a range of concentration for poly(I:C) molecules (such as 0.5, 1, 2, 2.5, or 5 mg/kg) to evaluate how such treatment improves mouse survival in a relevant model, such as a mouse melanoma model, with or without co-administering a further drug or a vaccine. At the same time, dose-response studies about specific biological activities induced by BO-11X treatment can be evaluated in parallel ex vivo, using human or animal samples at the level of apoptosis induction (by Caspase-related Glow), chemokine/cytokine secretion in biological fluid (for example, secretion of IL-6 and IP-10), in vitro cellular activation and/or proliferation (for example, associated to CD40, CD86, CD69 upregulation on relevant cell types). These studies can be performed using cells that are directly involved in disease (e.g. tumor cell, epithelial cell, endothelial or epithelial cells) or indirectly involved since performing some immune or immunoregulatory activities (e.g. human peripheral blood mononuclear cells, NK cells, B cells, CD4+/CD8+ T cells, dendritic cells). These studies can be further associated to the identification to molecules that may be used as biomarker to predict response to BO-11X (or lack thereof) in order to stratify disease stages and/or patients' populations for BO-11X treatment.

REFERENCES

Ammi R et al., 2015. Pharmacol. Ther.; 146:1 20-31.
Amos S M et al., 2011. Cancer Immunol. Immunother.; 60:671-83.
Bald T et al., 2014. Cancer Discov.; 4:674-87.
Bhoopathi P et al., 2014. Cancer Res.; 74:6224-35.
Bilensoy E, 2010. Expert Opin. Drug Deliv.; 7:795-809.
Chen L et al., 2013. Int. J. Nanomed.; 8:137-145.
Chiba Y et al., 2013. PLOSOne.; 8: e76159.
Cho K. et al., 2016, Immunobiology. pii: S0171-2985 (16) 30359-X. doi: 10.1016/j.imbio.2016.08.012.
Cobaleda-Siles M et al., 2014. Small.; 10:5054-67.
Duewell P et al., 2015., OncoImmunol.; 4 (10): e1029698.
Ewel C et al., 1992. Cancer Res.; 52:3005-10.
Fujimura T et al., 2006. Eur. J. Immunol.; 36:3371-80.
Galluzzi L et al., 2014. Oncotarget; 5:12472-508.
Garcia-Pascual C and Gomez R, 2013. J. Endometr.; 5 (suppl.1): S13 (SP-04).
Germershaus O and Nultsch K, 2015. Asi J Pharm Sci. 10:159-175.
Gupta S et al. 2016. Tumor Biol. 37:12089-12102.
Hafner A et al., 2013. Advanced Drug Delivery Rev.; 65 (10): 1386-1399.
Ho V et al.,2015. Oncotarget. 6:27252-27266).
Islam M et al., 2014. Journal of Controlled Release; 193:74-89.
Kabilova T et al., 2014. BMC Cancer.; 14:338.
Keir M et al., 2008. Annu. Rev. Immunol.; 26:677-704.
Kübler K et al., 2011. Eur. J. Immunol.; 41:3028-39.
Kurosaki T et al., 2009. Biomaterials, 30:2846-2853.
Le U et al., 2008. Canc. Biol. Ther.; 7:440-447.
Le U et al., 2009. Radiother. Oncol.; 90:273-279.
Levitzki A, 2012. Front. Oncol.; 2:4.
Matijević T et al., 2011. Chemotherapy; 57:460-7.
McBain S et al., 2007. J. Mater. Chem.; 17:2561-2565.
Nagato T and Celis E, 2014. Oncoimmunology; 3: e28440.
Ohashi T et al., 2013. Int. J. Cancer; 133:1107-18.
Palchetti S et al., 2013. RSC Adv.; 3:24597-24604.
Perrot I et al., 2010. J. Immunol. 185:2080-2088.
Pozuelo-Rubio M et al., 2014. Nano-Oncologicals in Adv. Del. Sci. Tech., Springer, pp. 453-470.
Saheki A et al., 2011. Int. J. Pharm.; 406:117-21.
Sajadian A et al., 2014. Arch. Virol.; 159:1951-1960.
Sanchez-Paulete A R et al., 2015. Cancer Discov.; pii: CD-15-0510.
Schaffert D et al., 2011. Pharm. Res., 28:731-741.
Shabani M et al., 2010. Avicenna J. Med. Biotech.; 2:123-130.
Storz U, 2011. MAbs.; 3:310-7.
Szabo A et al., 2012. Melanoma Res.; 22:351-361.
Taura M et al., 2010. Cancer Sci.; 101:1610-7.
Tormo D et al., 2009.Cancer Cell; 16:103-114.

Tutin-Moeavin I et al., 2015.org & Biomol Chem. 13:9005-9011.
Vacchelli E et al., 2013. Oncoimmunology; 2: e25396, e23510, e25595.
Van der Jeught K et al., 2015. Oncotarget; 6:1359-81.
Vega-Letter A et al., 2016. Stem Cell Res. & Ther. 7:150
Yoshino H and Kashiwakura I, 2013.Blood; 122:4721.
Yu L et al., 2016. Immunol Cell Biol. 94:875-885.
Zhang Y et al., 2014.Cancer Lett. 355:76-84.
Zhou Y et al., 2013. Innate Immun.; 19:184-192.
WO2004045491.
WO2005102278.
WO2011003883.
*Remington's Pharmaceutical Sciences* (edited by Allen, Lloyd V., Jr; $22^{nd}$ edition, 2012.

The invention claimed is:

1. Polyinosinic-polycytidylic acid [poly(I:C)] molecules, or a salt and/or solvate thereof, comprising double-stranded polynucleotides formed by annealing together respective single-stranded poly(I) and poly(C) molecules, wherein
    (a) at least 40% of the double-stranded polyribonucleotides comprise at least 850 base pairs, and
    (b) at least 50% of the double-stranded polyribonucleotides comprise between 400 and 5000 base pairs.

2. The poly(I:C) molecules of claim 1, wherein
    (a) at least 60% of the double-stranded polyribonucleotides have at least 850 base pairs;
    (b) at least 70% of the double-stranded polyribonucleotides have between 400 and 5000 base pairs; and
    (c) between 20% and 45% of the double-stranded polyribonucleotides have between 400 and 850 base pairs.

3. The poly(I:C) molecules of claim 1, wherein
    (a) between 5% and 60%, preferably between 10% and 30%, of the double-stranded polyribonucleotides have less than 400 base pairs;
    (b) between 20% and 45% or between 15% and 30%, preferably between 20% and 30%, of the double-stranded polyribonucleotides, have between 400 and 850 base pairs;
    (c) between 20% and 70%, preferably between 50% and 60%, of the double-stranded polyribonucleotides have between 850 and 5000 base pairs; and
    (d) between 0% and 10%, preferably 1% or less, of the double-stranded polyribonucleotides have more than 5000 base pairs.

4. The poly(I:C) molecules of claim 1, wherein
    (a) between 7% and 57% of the double-stranded polyribonucleotides have less than 400 base pairs;
    (b) between 20% and 45% of the double-stranded polyribonucleotides have between 400 and 850 base pairs;
    (c) between 20% and 70% of the double-stranded polyribonucleotides have between 850 and 5000 base pairs; and
    (d) between 0% and 9% of the double-stranded polyribonucleotides have more than 5000 base pairs.

5. A method for producing the poly(I:C) molecules of claim 1, comprising:
    (a) dissolving the poly(I) molecules in PBS to form a first solution;
    (b) separately dissolving the poly(C) molecules in PBS to form a second solution;
    (c) filtering each respective solution obtained from step (a) and step (b) using a membrane;
    (d) concentrating each respective permeate obtained for each respective filtration obtained in step (c) for each respective solution over a membrane to form a respective retentate for each respective solution;
    (e) mixing each respective retentate obtained for each respective solution (a) and (b) with a PBS solution;
    (f) determining the optical density of each respective retentate obtained in step (e) for each respective solution (a) and (b) and adjusting the total volume to a 1:1 stoichiometry;
    (g) combining the respective poly(I) solution with the poly(C) solution obtained at step (e) using heat;
    (h) cooling the resulting combined solution to room temperature;
    (i) filtering the solution obtained from step (h); and
    (j) purifying and desalting the resulting solution.

6. The method of claim 5, wherein at step (a) and step (b), the poly(I) molecules and the poly(C) molecules are respectively provided as a powder.

7. The method of claim 5, wherein at step (a) and step (b), the poly(I) molecules and the poly(C) molecules are respectively dissolved at 50° C.

8. The method of claim 5, wherein at step (c), the filtering membrane comprises a 300 kDa cut-off or a 500 kDa cut-off.

9. The method of claim 5, wherein the membrane of step (d) is a 30 kDa membrane.

10. The method of claim 5, wherein the mixing in step (e) is performed using a 10X PBS solution.

11. The method of claim 5, wherein the combining step (g) is performed at 55-62° C.

12. The method of claim 5, wherein the filtering step (i) is performed using a G3 glass filter, optionally having a pore size of about 15 µm to 40 µm.

13. The method of claim 5, wherein the desalting of step (j) is performed using isopropanol.

14. The method of claim 5, wherein the solution in step (j) is freeze-dried and/or lyophilized at room temperature.

15. The method of claim 5, wherein
    (a) the poly(C) solution of step (b) is heated to a temperature of between 61° C. to 66° C. prior to mixing with the poly(I) solution of step (a); and
    (b) the combining of step (g) is performed at a temperature of 55° C. to 58° C., after which the combined mixture is filtered over a 0.2 µm membrane.

16. The composition according to claim 1, wherein
    (a) the single-stranded poly(I) molecules comprise:
        (i) <400 bases consist of 80-95% poly(I) molecules,
        (ii) 400-850 bases consist of 5-20% poly(I) molecules,
        (iii) 850-5000 bases consist of 0-5% poly(I) molecules, and
        (iv) >5000 bases consist of 1% or less poly(I) molecules; and
    (b) the single-stranded poly(C) molecules comprise:
        (i) <400 bases consist of 20-82% poly(C) molecules,
        (ii) 400-850 bases consist of 15-40% poly(C) molecules,
        (iii) 850-5000 bases consist of 3-50% poly(C) molecules, and
        (iv) >5000 bases, consist of 1% or less of poly(C) molecules.

* * * * *